US010202373B2

(12) United States Patent
Bharathan et al.

(10) Patent No.: US 10,202,373 B2
(45) Date of Patent: Feb. 12, 2019

(54) HETEROARYLS AND USES THEREOF

(71) Applicant: MILLENNIUM PHARMACEUTICALS, INC., Cambridge, MA (US)

(72) Inventors: Indu T. Bharathan, Cambridge, MA (US); Chris Blackburn, Natick, MA (US); Jeffrey P. Ciavarri, Reading, MA (US); Jouhara Chouitar, Stoughton, MA (US); Courtney A. Cullis, Bedford, MA (US); Natalie D'Amore, Lynnfield, MA (US); Paul E. Fleming, Natick, MA (US); Kenneth M. Gigstad, Westford, MA (US); Krista E. Gipson, Medford, MA (US); Mario Girard, Quincy, MA (US); Yongbo Hu, Winchester, MA (US); Janice Lee, Cambridge, MA (US); Gang Li, Westborough, MA (US); Mansoureh Rezaei, Quincy, MA (US); Michael D. Sintchak, Winchester, MA (US); Francois Soucy, Stoneham, MA (US); Stephen G. Stroud, Medford, MA (US); Tricia J. Vos, Boston, MA (US); He Xu, Needham, MA (US); Yingchun Ye, Belmont, MA (US)

(73) Assignee: MILLENNIUM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/111,429

(22) PCT Filed: Jan. 13, 2015

(86) PCT No.: PCT/US2015/011250
§ 371 (c)(1),
(2) Date: Jul. 13, 2016

(87) PCT Pub. No.: WO2015/108881
PCT Pub. Date: Jul. 23, 2015

(65) Prior Publication Data
US 2016/0333007 A1 Nov. 17, 2016

Related U.S. Application Data

(60) Provisional application No. 62/054,757, filed on Sep. 24, 2014, provisional application No. 61/927,064, filed on Jan. 14, 2014.

(51) Int. Cl.
C07D 471/04 (2006.01)
A61K 45/06 (2006.01)
A61K 31/444 (2006.01)
A61K 31/506 (2006.01)

(52) U.S. Cl.
CPC .......... *C07D 471/04* (2013.01); *A61K 31/444* (2013.01); *A61K 31/506* (2013.01); *A61K 45/06* (2013.01)

(58) Field of Classification Search
CPC .......................... C07D 441/04; C07D 471/04
USPC .......................................... 546/113; 514/300
See application file for complete search history.

(56) References Cited

U.S. PATENT DOCUMENTS

| 7,601,716 | B2 | 10/2009 | Dorsey et al. |
| 9,751,854 | B2 | 9/2017 | Bharathan et al. |
| 9,802,960 | B2 | 10/2017 | Bharathan et al. |
| 2008/0280891 | A1 | 11/2008 | Kelly et al. |
| 2009/0163489 | A1 | 6/2009 | Booker et al. |

(Continued)

FOREIGN PATENT DOCUMENTS

| WO | WO 2004/041789 A1 | 5/2004 |
| WO | WO 2004/070050 A2 | 8/2004 |

(Continued)

OTHER PUBLICATIONS

May et al., "Structure-Activity, etc.," J. Med. Chem., 2007, 50, 65-73 and Supporting information, pp. S1-S11.*
National Cancer Institute, "A to Z List of Cancers," cancer.gov, accessed at http://www.cancer.gov/cancertopics/types/alphalist, accessed on May 29, 2014, 22 pages.
O'Brien C.J., "Current Management of Benign Parotid Tumors—The Role of Limited Superficial Parotidectomy," *Head & Neck*, vol. 25(11): 946-952, Wiley Periodicals, Inc., United States (2003).

(Continued)

*Primary Examiner* — Patricia L Morris
(74) *Attorney, Agent, or Firm* — Sterne Kessler Goldstein & Fox P.L.L.C.

(57) ABSTRACT

The present invention provides a compound of formula I:

wherein $R^1$, $X^1$, $X^2$, $R^2$, $R^3$, $R^4$, $R^5$, n, and m are as described in the specification. Such compounds are inhibitors of VPS34 and thus useful for treating proliferative, inflammatory, or cardiovascular disorders.

15 Claims, No Drawings

(56) References Cited

U.S. PATENT DOCUMENTS

| | | |
|---|---|---|
| 2010/0099684 A1 | 4/2010 | Cook, II et al. |
| 2011/0015173 A1 | 1/2011 | Florjancic et al. |
| 2011/0130380 A1 | 6/2011 | Barsanti et al. |
| 2012/0028979 A1 | 2/2012 | Basarab et al. |
| 2012/0142732 A1 | 6/2012 | Cullis et al. |
| 2013/0004859 A1 | 1/2013 | Yu et al. |
| 2013/0102608 A1 | 4/2013 | Hoelzemann et al. |
| 2013/0165483 A1 | 6/2013 | Chau et al. |
| 2015/0225422 A1 | 8/2015 | Bharathan et al. |
| 2015/0274708 A1 | 10/2015 | Seganish et al. |
| 2015/0322063 A1 | 11/2015 | Furuyama et al. |
| 2017/0073326 A1 | 3/2017 | Bharathan et al. |

FOREIGN PATENT DOCUMENTS

| | | |
|---|---|---|
| WO | WO 2006/051270 A1 | 5/2006 |
| WO | WO 2006/051311 A1 | 5/2006 |
| WO | WO 2006/065946 A1 | 6/2006 |
| WO | WO 2007/130468 A2 | 11/2007 |
| WO | WO 2007/135398 A1 | 11/2007 |
| WO | WO 2008/008059 A1 | 1/2008 |
| WO | WO 2008/025821 A1 | 3/2008 |
| WO | WO 2008/068470 A1 | 6/2008 |
| WO | WO 2008/079933 A2 | 7/2008 |
| WO | WO 2008/157191 A1 | 12/2008 |
| WO | WO 2009/013348 A2 | 1/2009 |
| WO | WO 2009/017822 A2 | 2/2009 |
| WO | WO 2009/039140 A1 | 3/2009 |
| WO | WO 2009/055418 A1 | 4/2009 |
| WO | WO 2009/087212 A2 | 7/2009 |
| WO | WO 2009/115517 A2 | 9/2009 |
| WO | WO 2009/147187 A1 | 12/2009 |
| WO | WO 2009/155121 A2 | 12/2009 |
| WO | WO 2010/007100 A1 | 1/2010 |
| WO | WO 2010/008847 A2 | 1/2010 |
| WO | WO 2010/017179 A1 | 2/2010 |
| WO | WO 2010/056574 A1 | 5/2010 |
| WO | WO 2010/057877 A1 | 5/2010 |
| WO | WO 2010/135524 A1 | 11/2010 |
| WO | WO 2011/026911 A1 | 3/2011 |
| WO | WO 2011/095196 A1 | 8/2011 |
| WO | WO 2012/009227 A1 | 1/2012 |
| WO | WO 2012/015723 A1 | 2/2012 |
| WO | WO 2012/021655 A2 | 2/2012 |
| WO | WO 2012/021696 A1 | 2/2012 |
| WO | WO 2012/037108 A1 | 3/2012 |
| WO | WO 2012/066065 A1 | 5/2012 |
| WO | WO 2012/066070 A1 | 5/2012 |
| WO | WO 2012/085244 A1 | 6/2012 |
| WO | WO 2012/085815 A1 | 6/2012 |
| WO | WO 2012/101062 A1 | 8/2012 |
| WO | WO 2012/101064 A1 | 8/2012 |
| WO | WO 2012/101066 A1 | 8/2012 |
| WO | WO 2012/168084 A1 | 12/2012 |
| WO | WO 2013/053983 A1 | 4/2013 |
| WO | WO 2013/126608 A1 | 8/2013 |
| WO | WO 2013/152063 A1 | 10/2013 |
| WO | WO 2013/190510 A2 | 12/2013 |
| WO | WO 2014/083327 A1 | 6/2014 |
| WO | WO 2014/096388 A2 | 6/2014 |
| WO | WO 2014/151616 A1 | 9/2014 |
| WO | WO 2015/108861 A1 | 7/2015 |
| WO | WO 2015/108881 A1 | 7/2015 |

OTHER PUBLICATIONS

Soussi, T., "p53 Antibodies in the Sera of Patients with Various Types of Cancer: A Review," *Cancer Research*, vol. 60(7): 1777-1788, American Association for Cancer Research, United States (2000).

Sun, Y-M., et al., "Recent Advances in Understanding the Biochemical and Molecular Mechanism of Diabetic Nephropathy," *Biochemical and Biophysical Research Communications*, vol. 433(4): 359-361, Elsevier Inc., United States (2013).

Yamada, S., et al.,"Alpha-1 Adrenoceptors in Human Prostate: Characterization and Alteration in Benign Prostatic Hypertrophy," *The Journal of Pharmacology and Experimental Therapeutics*, vol. 242(1): 326-330, The American Society for Pharmacology and Experimental Therapeutics, United States (1987).

Yamamoto, T., et al., "Expression of Transforming Growth Factor β is Elevated in Human and Experimental Diabetic Nephropathy," *Proceedings of the National Academy of Sciences USA*, vol. 90(5): 1814-1818, National Academy of Sciences, United States (1993).

Backer, J.M., "The regulation and function of Class III pl3Ks: novel roles for Vps34," *Biochem. J.*, vol. 410(1 ):1-17 (2008).

Bago, R. et al., "Characterization of VPS34-IN1, a selective inhibitor of Vps34, reveals that the phosphatidylinositol 3-phosphate-binding SGK3 protein kinase is a downstream target of class III phosphoinositide 3-kinase," *Biochem. J.*, vol. 463: 413-427 (2014).

Berenbaum, M.C., "The Expected Effect of a Combination of Agents: the General Solution," *Journal of Theoretical Biology*, vol. 114(3): 413-431 (1985).

Berge, S.M., et al., "Pharmaceutical Salts," *Journal of Pharmaceutical Sciences*, vol. 66(1 ): 1-19 (1977).

Bilanges, B., et al., "Cinderella finds her shoe: the first Vps34 inhibitor uncovers a new PI3K-AGC protein kinase connection," *Biochem. J.*, vol. 464: e7-e10 (2014).

Bliss, C.I., "The Toxicity of Poisons Applied Jointly," *Annals of Applied Biology*, vol. 26: 585-615 (1939).

Bruno, N.C., et al., "Design and Preparation of New Palladium Precatalysts for C—C and C—N Cross-Coupling Reactions," *Chemical Science*, vol. 4: 916-920 (2013).

Charrier, J.D., et al., "Discovery and Structure-Activity Relationship of 3-Aminopyrid-2-ones as Potent and Selective Interleukin-2 Inducible T-Cell Kinase (Itk) Inhibitors," *Journal of Medicinal Chemistry*, vol. 54: 2:341-2350 (2011 ).

Chou, T., et al., "Quantitative Analysis of Dose-Effect Relationships: The Combined Effects of Multiple Drugs or Enzyme Inhibitors," *Advances in Enzyme Regulation*, vol. 22: 27-55 (1984).

Delgado, M., et al,, "Autophagy and Pattern Recognition Receptors in Innate Immunity," *Immunol Rev.*, vol. 227( 1): 189-202 (2009).

Dowdle, W., "Selective VPS34 inhibitor blocks autophagy and uncovers a role for NCOA4 in ferritin degradation and iron homeostasis in vivo," *Nature Cell Biology*, vol. 16(11 ): 1069-1079, and Methods and Supplementary Information (12 pages, 23 pages total) (2014).

Driver, M., et al., A Second-Generation Catalyst for Alyl Halide, Amination: Mixed Secondary Amines from Aryl Halides and Primary Amines Catalyzed by (DPPF)PdCl$_2$, *J. Am. Chem. Soc.*, vol. 118: 7217-7218 (1996).

Dzierba, C., et al., Synthesis and structure-activity relationships of pyrido[3,2-b]pyrazin-3(4H)-ones and pteridin-7(8H)-ones as corticotropin-releasing factor-1 receptor antagonists, *Biorganic & Medicinal Chemistry Letters*, vol. 22: 4986-4989 (2012).

Engelman, J., et al., "The evolution of phosphatidylinositol 3-kinases as regulators of growth and metabolism," *Nature Reviews Genetics*, vol. 7(8): 606-619 (2006).

Funderburk, S.F., et al., "The Beclin 1-VPS34 complex—at the crossroads of autophagy and beyond," *Trends in Cell Biology*, vol. 20(6): 355-362 (2010).

Goh, L. K., et al., "Endocytosis of Receptor Tyrosine Kinases," *Cold Spring Harb Perspect Biol*, vol. 5: a017459, 18 pages (2013).

International Search Report for PCT/US2015/011191, 3 pages (dated Apr. 9, 2015).

International Search Report for PCT/US2015/011250, 3 pages (dated Apr. 6, 2015).

Jaber, N., et al., "Class III PI3K Vps34 plays an essential role in autophagy and in heart and liver function," *PNAS*, vol. 109(6): 2003-2008 (2012).

Jovic, M., et al., "The early endosome: a busy sorting station for proteins at the corssroads," *Histol Histopathol*, vol. 25(1 ): 99-112 (2010).

Knegtel, R., et al., "A Role for Hydration in Interleukin-2 Inducible T Cell Kinase (Itk) Selectivity," *Molecular Informatics*, vol. 30: 950-959 (2011 ).

(56) References Cited

OTHER PUBLICATIONS

Knight, S.D., et al., "Discovery of GSK2126458, a Highly Potent Inhibitor of PI3K and the Mammalian Target of Rapamycin," *ACS Med. Chem. Lett.*, vol. 1: 39-43 (2010).
Kondo, Y. et al., "The Role of Autophagy in Cancer Development and Response to Therapy," *Nature Reviews Cancer*, vol. 5(9): 726-34 (2005).
Lebegue, N., et al., "Novel Benzopyridothiadiazepines as Potential Active Antitumor Agents," *J. Med. Chem.*, vol. 48(23): 7363-7373 (2005).
Liu, J., et al., "Discovery of AMG 853, a CRTH2 and DP Dual Antagonist," *ACS Med. Chem. Lett.*, vol. 2: 326-330 (2011).
Mellman, I., et al., "Endocytosis and Cancer," *Cold Spring Harb Perspect Biol*, vol. 5: a016949, 25 pages (2013).
Miller, S., et al., "Shaping development of autophagy inhibitors with the structure of the lipid kinase Vps34," *Science*, vol. 327(5973): 1638-1642 (2010).
Pandarus, V., et al., "Efficient Screening and Library Generation in Parallel C—C Coupling Reactions Mediated by Organosilica SiliaCat Palladium Catalysts," *Org. Process Res. Dev.*, vol. 16: 117-122 (2012).
Pasquier, B., et al., "Discovery of (2,S)-8-[(3R)-Methylmorpholin-4-yl]-1-(3-methyl-2-oxobutyl)-2-(trifluoromethyl)-3,4-dihydro-2H-pyrimido[1,2a]pyrimidin-6-one: A Novel Potent and Selective Inhibitor of Vps34 for the Treatment of Solid Tumors," *J. Med. Chem.*, vol. 58(1): 376-400 (2015).
Peterson, J.J., et al., "Nonlinear Blending: A Useful General Concept for the Assessment of Combination Drug Synergy," *Journal of Receptors and Signal Transduction Research*, vol. 27(2-3): 125-146 (2007).
PuhChem Substance summary for CID 10468190, (2-methylpyrrolidin-1-yl)-(5-pyridin-4-ylpyridin-3-yl)methanon, CAS Registry No. 613661-01-1; Record created Oct. 25, 2006.
PubChem Substance summary for CID 11566395, 4-chloro-N-(5-pyridin-4-ylpyrictin-3-yl)benzensulfonantide, CAS Registry No. 887374-50-7; Record created Oct. 26, 2006.
PuhChem Substance summary for CID 13066345, N-(1-methyl-5-pyridin-4- ylpyrazolo[3,4-b]pyridin-3-yl)formamide; Record created Feb. 8, 2007.
PubChem Substance summary for CID 46315357, 2-chloro-4-methyl-5-pyridin-4-ylpyridine; Record created Jul. 21, 2010.
PubChem Substance summary for CID 4636058, 2-[benzenesulfonyl-[(4-methylphenyl)methyl]amino]-N-phenylacetamid; Record created Jul. 21, 2010.
Ronan, B., et al., "A highly potent and selective Vps34 inhibitor alters vesicle trafficking and autophagy," *Nature Chemical Biology*, vol. 10: 1013-1019 (2014).
Shintani, T., et al., "Autophagy in Health and Disease: A Double-Edged Sword," *Science*, vol. 306(5698): 990-995 (2004).
Stec, M. M., et al., "Structure-Activity Relationships of Phosphoinositide 3-Kinase (PI3K)/Mammalian Target of Rapamycin (mTOR) Dual Inhibitors: Investigations of Various 6,5-heterocycles to Improve Metabolic Stability," *J. Med. Chem.*, vol. 54(14): 5174-84 (2011).
Sunose, M., et al., "Discovery of 5-(2-amino-[1,2,4]triazolo[1,5-a]pyridin-7-yl)-N-(tert-butyl)pyridine-3-sulfonamide (CZC24758), as a potent, orally bioavailable and selective inhibitor of PI3K for the treatment of inflammatory disease," *Bioorganic & Medicinal Chemistry Letters*, vol. 22: 4613-4618 (2012).
Suzuki, A., "Recent advances in cross-coupling reactions of organoboron derivatives with organic electrophiles, 1995-1998," *Journal of Organometallic Chemistry*, vol. 576: 147-168 (1999).
Tallarida, R. J., "An Overview of Drug Combination Analysis with Isobolograms," *Perspectives of Pharmacology and Experimental Therapeutics*, vol. 319(1): 1-7 (2006).
Thoresen, S. B., et al., "A phosphatidylinositol 3-kinase class III sub-complex containing VPS15, VPS34, Beclin 1, UVRAG and BIF-1 regulates cytokinesis and degradative endocytic traffic," *Experimental Cell Research*, vol. 316:3 368-3378 (2010).
Triola, G., "Chemical tools for modulating autophagy," *Tetrahedron*, vol. 71(3): 387-406 (2015).
Written Opinion for PCT/US2015/011191, 7 pages (dated Apr. 9, 2015).
Written Opinion for PCT/US2015/011250, 15 pages (dated Apr. 6, 2015).
Wurz, R.P. et al., Synthesis and structure-activity relationships of dual PI3K/mTOR inhibitors based on a 4-amino-6-methyl-1,3,5-triazine sulfonamide scaffold, Bioorganic & Medicinal Chemistry Letters, 22:5714-5720 (2012).
Yan, Y., et al., "Regulation of Class III (Vps34) PI3Ks," *Biochemical Society Transactions*, vol. 35(2): 239-241 (2007).
Yin, J., et al., "Pd-catalyzed N-Arylation of Heteroarylamines," *Organic Letters*, vol. 4(20): 3481-3484 (2002).
International Preliminary Report on Patentability for International Application No. PCT/US2015/011191, The International Bureau of WIPO, Geneva, Switzerland, dated Jul. 19, 2016, 8 pages.
Honda, A., et al., "Potent, Selective, and Orally Bioavailable Inhibitors of VPS34 Provide Chemical Tools to Modulate Autophagy in Vivo," *ACS Med Chem Lett.*, vol. 7(1): 72-76, American Chemical Society, United States (Nov. 2015).
International Preliminary Report on Patentability for International Application No. PCT/US2015/011250, The International Bureau of WIPO, Geneva, Switzerland, dated Jul. 19, 2016, 7 pages.
Rostislavleva, K., et al., "Structure and flexibility of the endosomal Vps34 complex reveals the basis of its function on membranes," *Science*, vol. 350(6257): aac7365, American Association for the Advancement of Science, United States, 13 pages (Oct. 2015).
Uchida, Y., et al., "Endosomal Phosphatidylinositol 3-Kinase is Essential for Canonical GPCR Signaling," *Molecular Pharmacology*, vol. 91(5): 65-73, The American Society for Pharmacology and Experimental Therapeutics, United States (Jan. 2017).
Bunz, F., "The Genetic Basis of Cancer," *Principles of Cancer Genetics*, 1st Edition, Chapter 1, pp. 1-47, Springer Science+Business Media B.V, Netherlands (2008).
Cashman, J.D., et al., "Fucoidan Film Safely Inhibits Surgical Adhesions in a Rat Model," *The Journal of Surgical Research*, vol. 171(2): 495-503, Elsevier Inc., United States (2011).
Chen, N., et al. "Autophagy and tumorigenesis," *FEBS Letters*, vol. 584(7): 1427-1435, Elsevier B. V., England (2010).
Fabbro, D., et al., "Targeting Cancer with Small-Molecular Weight Kinase Inhibitors," *Kinase Inhibitors: Methods and Protocols, Methods in Molecular Biology*, vol. 795, Chapter 1, Kuster, B., ed., pp. 1-34, Springer Science+Business Media, LLC, United States (2012).
Furuya, T., et al., "Negative Regulation of Vps34 by Cdk Mediated Phosphorylation," *Molecular Cell*, vol. 38(4): 500-511, Elsevier Inc., United States (2010).
Gaestel, M., et al., "Small-Molecule Protein and Lipid Kinase Inhibitors in Inflammation and Specific Models for Their Evaluation," *Kinase Inhibitors: Methods and Protocols, Methods in Molecular Biology*, vol. 795, Chapter 1, Kuster, B., ed., pp. 35-44, Springer Science+Business Media, LLC, United States (2012).
Ghiassi-Nejad, Z., et al. "Advances in Antifibrofic Therapy," *Expert Review of Gastroenterology & Hepatology*, vol. 2(6): 803-816, Expert Reviews Ltd., England (2008).
Km, J., et al., "A Signaling Network in Phenylephrine-induced Benign Prostatic Hyperplasia," *Endocrinology*, vol. 150(8): 3576-3583, Oxford University Press, United States (2009).
Kok, R.J., "Targets in Fibrotic Disorders," *Pharmaceutical Research*, vol. 25(10): 2413-2415, Springer Science+ Business media, LLC, United States (2008).
Kong, D. and Yamori, T., "Phosphatidylinositol 3-kinase Inhibitors: Promising Drug Candidates for Cancer Therapy," Cancer Science 99(9):1734-1740, Wiley Publishing on behalf of the Japanese Cancer Association, England (2008).
Kuppen, P.J.K., et al., "Tumor Structure and Extracellular Matrix as a Possible Barrier for Therapeutic Approaches Using Immune Cells or Adenoviruses in Colorectal Cancer," *Histochemistty and Cell Biology*, vol. 115(1): 67-72, Springer-Verlag, Germany (2001).
Lim, A. K.H., "Diabetic Nephropathy—Complications and Treatment," *International Journal of Nephrology and Renovascular Disease*, vol. 7: 361-381, Dove Medical Press Limited, England (2014).

(56) References Cited

OTHER PUBLICATIONS

Lissoni, P., et al., "Biotherapy with the Pineal Hormone Melatonin Plus Aloe and Myrrh Tincture in Untreatable Metastatic Cancer Patients as an Essence Therapy of Cancer," *Cancer Therapy*, vol. 7: 397-401 (2009).

Luo, J., et al., "Principles of Cancer Therapy: Oncogene and Non-oncogene Addiction," Cell 136(5):823-837, Elsevier Inc., United States (2009).

Nandeesha, H., et al., "Hyperinsulinernia and Dyslipidernia in Non-diabetic Benign Prostatic Hyperplasia," *Clinica Chimica Acta*, vol. 370(1-2): 89-93, Elsevier B.V., Netherlands (2006).

\* cited by examiner

HETEROARYLS AND USES THEREOF

CROSS-REFERENCE TO RELATED APPLICATIONS

This application claims benefit of U.S. Provisional Application No. 62/054,757, filed Sep. 24, 2014, and U.S. Provisional Application No. 61/927,064, filed Jan. 14, 2014, each of which is incorporated by reference in its entirety.

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR. TRRAP and SMG1.

Vacuolar Protein Sorting 34 (VPS34) is the sole Class III PI3K family member. VPS34 functions in the formation and trafficking of multiple intracellular vesicles, including vacuoles, endosomes, multivessicular bodies, lysosomes and autophagosomes (reviewed in Backer Biochem J 2008; Yan and Backer Biochem J 2007). VPS34 carries out these activities by phosphorylating PtdIns forming PtdIns3P, resulting in the recruitment and localization of a variety of FYVE and PX domain containing effector proteins that facilitate vesicular formation, elongation and movement. At a cellular level, inhibition of VPS34 results in defects in protein sorting and autophagy. Broadly defined, autophagy is a regulated process whereby cells catabolize subcellular components targeted for degradation by enclosing them in double-membrane vesicles which then fuse with lysosomes. Autophagy has been best characterized as occurring during times of nutrient deprivation, but also plays a role in normal cellular and tissue homeostasis and functions, including the development of multiple tissue types, the immune response, clearance of neuronal aggregates and tumor suppression. In addition to functioning in vesicle formation and movement, VPS34 may also participate in several signal transduction pathways (reviewed in Backer Biochem J 2008). Given that VPS34 plays an important role in many critical cellular processes including autophagy, inhibitors of VPS34 may have therapeutic application in a number of diseases, including but not limited to cancer, muscular disorders, neurodegeneration, inflammatory disease, infectious disease and other age related illnesses (reviewed in Shintani and Klionsky Science 2004; Kondo et al Nat Rev Cancer 2005; Delgato et al Immunol Rev 2009). Therefore, it would be beneficial to provide novel VPS34 inhibitors that possess good therapeutic properties, especially for the treatment of proliferative, inflammatory, or cardiovascular disorders.

DETAILED DESCRIPTION OF THE INVENTION

1. General Description of Certain Embodiments of the Invention:

This invention provides compounds that are inhibitors of VPS34, and accordingly can be useful for the treatment of proliferative, inflammatory, or cardiovascular disorders.

In some embodiments, the present invention provides a compound of formula I:

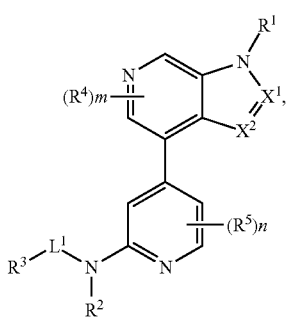

I or a pharmaceutically acceptable salt thereof, wherein:
each of $X^1$ and $X^2$, independently, is N, CH, or $CR^4$;
$L^1$ is a bond, —C(O)—, —C(O)—O—, —S(O)$_2$—, —C(O)N($R^a$)—, or —S(O)$_2$N($R^a$)—; wherein each $R^a$, independently, is hydrogen or $C_{1-4}$ alkyl;
wherein when $L^1$ is a bond and $R^3$ is phenyl, naphthyl, or heteroaryl, $R^2$ optionally joins with $R^7$ to form an optionally substituted 5-7-membered heterocyclyl or an optionally substituted 5-6-membered heteroaryl;
$R^1$ is hydrogen or -$L^2$-$R^6$ wherein:
  $L^2$ is $C_{1-4}$ alkylene, —C(O)—, —C(O)—O—, —S(O)—, —S(O)$_2$—, —C(O)N($R^b$)—, or —S(O)$_2$N($R^b$)—; wherein each $R^b$, independently, is hydrogen or $C_{1-4}$ alkyl; and
  $R^6$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur; each of which being optionally substituted with 1-5 $R^7$; or $R^b$ and $R^6$ combine to form a 3-10-membered heterocyclyl having 1-4 heteroatoms independently selected from nitrogen, oxygen, or sulfur wherein said heterocyclyl is optionally substituted with 1-5 $R^7$;
$R^2$ is hydrogen or $C_{1-4}$ alkyl;
$R^3$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur; provided that if $R^3$ is hydrogen, $L^1$ is a bond; each of $R^3$ being optionally substituted with 1-5 $R^7$ wherein:
each $R^7$ independently is —CN, halo, or -$L^3$-$R^8$ wherein:
  $L^3$ is a bond, $C_{1-4}$ aliphatic, —O—, —N($R^c$)—, —S—, —S(O)—, —S(O)$_2$—, —C(O)—, —C(O)O—, —C(O)N($R^c$)—, —N($R^c$)C(O)—, —N($R^c$)C(O)O—, —S(O)$_2$N$R^c$, —N($R^c$)S(O)$_2$—, —OC(O)N($R^c$)—, —N($R^c$)C(O)N($R^d$)—, —N($R^c$)S(O)$_2$N($R^d$)—, or —OC(O)—;
  each occurrence of $R^c$ and $R^d$, independently, is hydrogen or $C_{1-4}$ alkyl, and $R^8$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur;

each occurrence of $R^4$ and $R^5$, independently, is —CN, halo, or -$L^4$-$R^9$ wherein:

$L^4$ is $C_{1-4}$ alkylene, —O—, —N($R^e$)—, —S—, —S(O)—, —S(O)$_2$—, —C(O)—, —CO$_2$—, —C(O)N($R^e$)—, —N($R^e$)C(O)—, —N($R^e$)C(O)O—, —S(O)$_2$N($R^e$)—, —N($R^e$)S(O)$_2$—, —OC(O)N($R^e$)—, —N($R^e$)C(O)N($R^f$)—, —N($R^e$)S(O)$_2$N($R^f$)—, or —OC(O)—;

each occurrence of $R^e$ and $R^f$, independently, is hydrogen or $C_{1-4}$ alkyl; and $R^9$ is hydrogen, —NH$_2$, or $C_{1-6}$ aliphatic;

m is 0-2; and n is 0-3.

For clarity, it is understood that the first listed atom (from left) in the exemplary $L^1$ groups described herein is covalently bonded to the nitrogen of the —NR$^2$— moiety. Accordingly, exemplary —NR$^2$-$L^1$-$R^3$ moieties described herein include —NR$^2$—C(O)—$R^3$, —NR$^2$—C(O)—O—$R^3$, —NR$^2$—S(O)$_2$—$R^3$, —NR$^2$—C(O)N($R^a$)—$R^3$, and —NR$^2$—S(O)$_2$N($R^a$)—$R^3$. Similarly, the first listed atom (from left) in the exemplary $L^2$ groups described herein is covalently bonded to the ring nitrogen.

2. Compounds and Definitions:

Compounds of this invention include those described generally for formula I, above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon which is completely saturated or which contains one or more units of unsaturation. For example, suitable aliphatic groups include optionally substituted linear or branched alkyl, alkenyl, alkynyl groups. Unless otherwise specified, in various embodiments, aliphatic groups have 1-12, 1-10, 1-8, 1-6, 1-4, 1-3, or 1-2 carbon atoms. It is apparent to a skilled person in the art that in some embodiments, the "aliphatic" group described herein can be bivalent.

The term "alkyl", used alone or as part of a larger moiety, refers to a saturated, optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms, and which is not aromatic. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The term "heteroatom" refers to one or more of oxygen, sulfur, nitrogen, phosphorus, and silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. For example, the aryl group is a $C_{6-10}$ aryl group (i.e., phenyl and naphthyl). Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. For example, the aralkyl group is $C_{6-10}$ aryl$C_{1-6}$ alkyl, including, without limitation, benzyl, phenethyl, and naphthylmethyl.

The term "halogen" or "halo" means F, Cl, Br, or I.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, for example, mono-, bi-, or tricyclic, (e.g., mono- or bicyclic). The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR⁺ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, e.g., from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted or replaced by the functional group. Examples of suitable "interrupting functional groups" are described in the specification and claims herein.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl (e.g., phenyl or napathyl) or heteroaryl group (e.g., pyridyl) also include and are generally selected from -halo, —NO$_2$, —CN, —R⁺, —C(R⁺)=C(R⁺)$_2$, —C≡C—R⁺, —OR⁺, —SR°, —S(O)R°, —SO$_2$R°, —SO$_3$R⁺, —SO$_2$N(R⁺)$_2$, —N(R⁺)$_2$, —NR⁺C(O)R⁺, —NR⁺C(S)R⁺, —NR⁺C(O)N(R⁺)$_2$, —NR⁺C(S)N(R⁺)$_2$, —N(R⁺)C(=NR⁺)—N(R⁺)$_2$, —N(R⁺)C(=NR⁺)—R°, —NR⁺CO$_2$R⁺, —NR⁺SO$_2$R°, —NR⁺SO$_2$N(R⁺)$_2$, —O—C(O)R⁺, —O—CO$_2$R⁺, —OC(O)N(R⁺)$_2$, —C(O)R⁺, —C(S)R°, —CO$_2$R⁺, —C(O)—C(O)R⁺, —C(O)N(R⁺)$_2$, —C(S)N(R⁺)$_2$, —C(O)N(R⁺)—OR⁺, —C(O)N(R⁺)C(=NR⁺)—N(R⁺)$_2$, —N(R⁺)C(=NR⁺)—N(R⁺)—C(O)R⁺, —C(=NR⁺)—N(R⁺)$_2$, —C(=NR⁺)—OR⁺, N(R⁺)—N(R⁺)$_2$, —C(=NR⁺)—N(R⁺)—OR⁺, —C(R⁺)=N—OR⁺, —P(O)(R⁺)$_2$, —P(O)(OR⁺)$_2$, —O—P(O)—OR⁺, and —P(O)(NR⁺)—N(R⁺)$_2$, wherein R⁺, independently, is hydrogen or an optionally substituted aliphatic, aryl, heteroaryl, cycloaliphatic, or heterocyclyl group, or two independent occurrences of R⁺ are taken together with their intervening atom(s) to form an optionally substituted 5-7-membered aryl, heteroaryl, cycloaliphatic, or heterocyclyl ring. Each R° is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)₂, =N—N(R*)₂, =N—OR*, =N—NHC(O)R*, =N—NHCO₂R°=N—NHSO₂R° or =N—R* where R° is defined above, and each R* is independently selected from hydrogen or an optionally substituted C₁₋₆ aliphatic group.

In addition to the substituents defined above and herein, optional substituents on the nitrogen of a non-aromatic heterocyclic ring also include and are generally selected from —R⁺, —N(R⁺)₂, —C(O)R⁺, —C(O)OR⁺, —C(O)C(O)R⁺, —C(O)CH₂C(O)R⁺, —S(O)₂R⁺, —S(O)₂N(R⁺)₂, —C(S)N(R⁺)₂, —C(=NH)—N(R⁺)₂, or —N(R⁺)S(O)₂R⁺; wherein each R⁺ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R⁺ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R⁺ (or any other variable similarly defined in the specification and claims herein), are taken together with their intervening atom(s) include, but are not limited to the following: a) two independent occurrences of R⁺ (or any other variable similarly defined in the specification or claims herein) that are bound to the same atom and are taken together with that atom to form a ring, for example, N(R⁺)₂, where both occurrences of R⁺ are taken together with the nitrogen atom to form a piperidin-1-yl, piperazin-1-yl, or morpholin-4-yl group, and b) two independent occurrences of R⁺ (or any other variable similarly defined in the specification or claims herein) that are bound to different atoms and are taken together with both of those atoms to form a ring, for example where a phenyl group is substituted with two occurrences of OR⁺

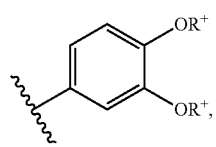

these two occurrences of R⁺ are taken together with the oxygen atoms to which they are bound to form a fused 6-membered oxygen containing ring:

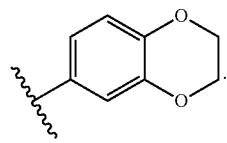

It will be appreciated that a variety of other rings (e.g., spiro and bridged rings) can be formed when two independent occurrences of R⁺ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a ¹³C- or ¹⁴C-enriched carbon are within the scope of this invention. Such compounds are useful, as a nonlimiting example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization, formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diastereomeric pairs, mixtures of diasteromers, mixtures of diasteromeric pairs, mixtures of diasteromers in which one diastereomer is enriched relative to the other diastereomer(s) and mixtures of diasteromeric pairs in which one diasteromeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds:

As described generally above, in some embodiments the present invention provides a compound of formula I:

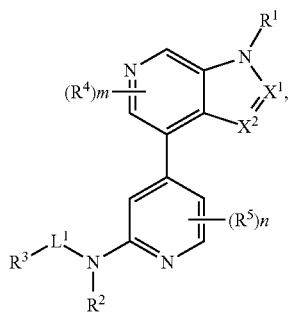

I or a pharmaceutically acceptable salt thereof, wherein:
each of $X^1$ and $X^2$, independently, is N, CH, or $CR^4$;
$L^1$ is a bond, —C(O)—, —C(O)—O—, —S(O)$_2$—, —C(O)N($R^a$)—, or —S(O)$_2$N($R^a$)—; wherein each $R^a$, independently, is hydrogen or $C_{1-4}$ alkyl;
wherein when $L^1$ is a bond and $R^3$ is phenyl, naphthyl, or heteroaryl, $R^2$ optionally joins with $R^7$ to form an optionally substituted 5-7-membered heterocyclyl or an optionally substituted 5-6-membered heteroaryl;
$R^1$ is hydrogen or -$L^2$-$R^6$ wherein:
  $L^2$ is $C_{1-4}$ alkylene, —C(O)—, —C(O)—O—, —S(O)—, —S(O)$_2$—, —C(O)N($R^b$)—, or —S(O)$_2$N($R^b$)—; wherein each $R^b$, independently, is hydrogen or $C_{1-4}$ alkyl; and
  $R^6$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur; each of which being optionally substituted with 1-5 $R^7$; or $R^b$ and $R^6$ combine to form a 3-10-membered heterocyclyl having 1-4 heteroatoms independently selected from nitrogen, oxygen, or sulfur wherein said heterocyclyl is optionally substituted with 1-5 $R^7$;
$R^2$ is hydrogen or $C_{1-4}$ alkyl;
$R^3$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur; provided that if $R^3$ is hydrogen, $L^1$ is a bond; each of $R^3$ being optionally substituted with 1-5 $R^7$ wherein:
each $R^7$ independently is —CN, halo, or -$L^3$-$R^8$ wherein:
  $L^3$ is a bond, $C_{1-4}$ aliphatic, —O—, —N($R^c$)—, —S—, —S(O)—, —S(O)$_2$—, —C(O)—, —C(O)O—, —C(O)N($R^c$)—, —N($R^c$)C(O)—, —N($R^c$)C(O)O—, —S(O)$_2$N$R^c$, —N($R^c$)S(O)$_2$—, —OC(O)N($R^c$)—, —N($R^c$)C(O)N($R^d$)—, —N($R^c$)S(O)$_2$N($R^d$)—, or —OC(O)—;
  each occurrence of $R^c$ and $R^d$, independently, is hydrogen or $C_{1-4}$ alkyl, and
  $R^8$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur;
each occurrence of $R^4$ and $R^5$, independently, is —CN, halo, or -$L^4$-$R^9$ wherein:
  $L^4$ is $C_{1-4}$ alkylene, —O—, —N($R^e$)—, —S—, —S(O)—, —S(O)$_2$—, —C(O)—, —CO$_2$—, —C(O)N($R^e$)—, —N($R^e$)C(O)—, —N($R^e$)C(O)O—, —S(O)$_2$N($R^e$)—, —N($R^e$)S(O)$_2$—, —OC(O)N($R^e$)—, —N($R^e$)C(O)N($R^f$)—, —N($R^e$)S(O)$_2$N($R^f$)—, or —OC(O)—;
  each occurrence of $R^e$ and $R^f$, independently, is hydrogen or $C_{1-4}$ alkyl; and
  $R^9$ is hydrogen, —NH$_2$, or $C_{1-6}$ aliphatic;
m is 0-2; and
n is 0-3.

In some embodiments, when $L^1$ is a bond and $R^3$ is phenyl, naphthyl, or heteroaryl, $R^2$ joins with $R^7$ to form an optionally substituted 5-7-membered heterocyclyl or an optionally substituted 5-6-membered heteroaryl. For example, —N($R^2$)-$L^1$-$R^3$ can be

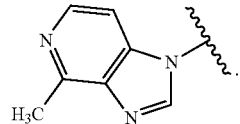

In some embodiments the present invention provides a compound of formula I,

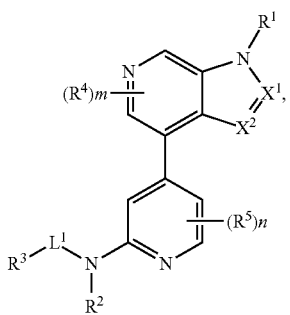

I or a pharmaceutically acceptable salt thereof, wherein:

each of $X^1$ and $X^2$, independently, is N, CH, or $CR^4$;

$L^1$ is a bond, —C(O)—, —C(O)—O—, —S(O)$_2$—, —C(O)N($R^a$)—, or —S(O)$_2$N($R^a$)—; wherein each $R^a$, independently, is hydrogen or $C_{1-4}$ alkyl;

$R^1$ is hydrogen or -$L^2$-$R^6$ wherein:
  $L^2$ is $C_{1-4}$ alkylene, —C(O)—, —C(O)—O—, —S(O)—, —S(O)$_2$—, —C(O)N($R^b$)—, or —S(O)$_2$N($R^b$)—; wherein each $R^b$, independently, is hydrogen or $C_{1-4}$ alkyl; and
  $R^6$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur; each of which being optionally substituted with 1-5 $R^7$; or $R^b$ and $R^6$ combine to form a 3-10-membered heterocyclyl having 1-4 heteroatoms independently selected from nitrogen, oxygen, or sulfur wherein said heterocyclyl is optionally substituted with 1-5 $R^7$;

$R^2$ is hydrogen or $C_{1-4}$ alkyl;

$R^3$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur; provided that if $R^3$ is hydrogen, $L^1$ is a bond; each of $R^3$ being optionally substituted with 1-5 $R^7$ wherein:

each $R^7$ independently is —CN, halo, or -$L^3$-$R^8$ wherein:
  $L^3$ is a bond, $C_{1-4}$ aliphatic, —O—, —N($R^c$)—, —S—, —S(O)—, —S(O)$_2$—, —C(O)—, —C(O)O—, —C(O)N($R^c$)—, —N($R^c$)C(O)—, —N($R^c$)C(O)O—, —S(O)$_2$N$R^c$, —N($R^c$)S(O)$_2$—, —OC(O)N($R^c$)—, —N($R^c$)C(O)N($R^d$)—, —N($R^c$)S(O)$_2$N($R^d$)—, or —OC(O)—;
  each occurrence of $R^c$ and $R^d$, independently, is hydrogen or $C_{1-4}$ alkyl, and
  $R^8$ is hydrogen, $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur;

each occurrence of $R^4$ and $R^5$, independently, is —CN, halo, or -$L^4$-$R^9$ wherein:
  $L^4$ is $C_{1-4}$ alkylene, —O—, —N($R^e$)—, —S—, —S(O)—, —S(O)$_2$—, —C(O)—, —CO$_2$—, —C(O)N($R^e$)—, —N($R^e$)C(O)—, —N($R^e$)C(O)O—, —S(O)$_2$N($R^e$)—, —N($R^e$)S(O)$_2$—, —OC(O)N($R^e$)—, —N($R^e$)C(O)N($R^f$)—, —N($R^e$)S(O)$_2$N($R^f$)—, or —OC(O)—;
  each occurrence of $R^e$ and $R^f$, independently, is hydrogen or $C_{1-4}$ alkyl; and
  $R^9$ is hydrogen, —NH$_2$, or $C_{1-6}$ aliphatic;

m is 0-2; and n is 0-3.

In some embodiments, $X^1$ is CH or $CR^4$ and $X^2$ is N. In some embodiments, $X^1$ is N and $X^2$ is CH or $CR^4$. In other embodiments, $X^1$ and $X^2$ are both CH. In some embodiments, each of $X^1$ and $X^2$ independently is CH or $CR^4$. In still other embodiments, $X^1$ is CH and $X^2$ is $CR^4$, or $X^2$ is CH and $X^1$ is $CR^4$. In some embodiments, each $X^1$ and $X^2$ is independently selected from those depicted in Table 1, below.

In some embodiments, $L^1$ is —C(O)— or —C(O)—O—. In other embodiments, $L^1$ is —C(O)—. In some embodiments, $L^1$ is a bond. In other embodiments, $L^1$ is —C(O)—, —C(O)—O—, —S(O)$_2$—, —C(O)N($R^a$)—, or —S(O)$_2$N($R^a$)—. In some embodiments, $L^1$ is selected from those depicted in Table 1, below.

In some embodiments, $R^a$ is hydrogen. In other embodiments, $R^a$ is unsubstituted $C_{1-4}$ alkyl. In still other embodiments, $R^a$ is substituted $C_{1-4}$ alkyl. In some embodiments, $R^a$ is H or CH$_3$. In some embodiments, $R^a$ is selected from those depicted in Table 1, below.

In some embodiments, the $R^1$ group is hydrogen. In some embodiments, the $R^1$ group described by -$L^2$-$R^6$ is selected from: —SO$_2$($C_{1-6}$ alkyl), —SO$_2$(phenyl), —SO$_2$N($C_{1-3}$ alkyl)$_2$, —SO$_2$($C_{3-6}$ cycloaliphatic), —SO$_2$NH($C_{1-3}$ alkyl), —SO$_2$—($C_{1-2}$ alkylene)-($C_{3-6}$ cycloaliphatic), and —($C_{1-2}$ alkylene)-($C_{3-6}$ cycloaliphatic). In other embodiments, $R^1$ is —SO$_2$CH$_3$, —SO$_2$(phenyl), —SO$_2$N(CH$_3$)$_2$, —SO$_2$(cyclopropyl), —SO$_2$(2,4-difluorophenyl), —SO$_2$(cyclopentyl), —SO$_2$CH$_2$CH(CH$_3$)$_2$, —SO$_2$CH$_2$CH$_3$, —SO$_2$CH$_2$(cyclopropyl), or —SO$_2$(o-tolyl). In other embodiments, $R^1$ is selected from those depicted in Table 1, below.

In some embodiments, $L^2$ is —S(O)$_2$—. In other embodiments, $L^2$ is $C_{1-4}$ alkylene. In certain embodiments, $L^2$ is —C(O)—, —C(O)—O—, —S(O)—, —S(O)$_2$—, —C(O)N($R^b$)—, or —S(O)$_2$N($R^b$)—. In some embodiments, $L^2$ is —C(O)— or —S(O)$_2$—. In some embodiments, $L^2$ is —C(O)—. In some embodiments, $L^1$ is selected from those depicted in Table 1, below.

In some embodiments, $R^b$ is hydrogen. In other embodiments, $R^b$ is unsubstituted $C_{1-4}$ alkyl. In still other embodiments, $R^b$ is substituted $C_{1-4}$ alkyl. In some embodiments, $R^b$ is selected from those depicted in Table 1, below.

In some embodiments, $R^6$ is $C_{1-4}$ alkyl, 3-6-membered cycloaliphatic, phenyl, naphthyl, 3-6-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur. In other embodiments, $R^6$ is methyl, ethyl, or phenyl optionally substituted with 1-3 groups independently selected from halo or $C_{1-3}$ alkyl. In some embodiments, $R^6$ is hydrogen. In other embodiments, $R^6$ is $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur. In some embodiments, $R^1$ is a $C_{1-6}$ aliphatic comprising a substituent that is =NH and/or a substituent that is —NH$_2$. In some embodiments, $R^1$ is methyl substituted with =NH and —NH$_2$.

In some embodiments, each $R^6$ is independently selected from those depicted in Table 1, below.

When $R^6$ is a not hydrogen, $R^6$ can be unsubstituted or substituted. In some embodiments, $R^6$ is optionally substituted with 1-5 $R^7$ independently selected from the exemplary $R^7$ moieties described herein. In some embodiments, each optional $R^7$ substituent for $R^6$ is selected from halo, $C_{1-6}$ aliphatic (e.g., $C_{1-6}$ alkyl), —O—($C_{1-6}$ aliphatic) (e.g., —O—($C_{1-6}$ alkyl), hydroxyl, amino, mono($C_{1-6}$ alkyl)amino, and di($C_{1-6}$ alkyl)amino. In other embodiments, each optional substituent group of $R^6$ (e.g., $R^7$) is independently selected from those depicted in Table 1, below.

In some embodiments, $R^b$ and $R^6$ combine to form a 3-6-membered heterocyclyl having 1-4 heteroatoms independently selected from nitrogen, oxygen, or sulfur. In other embodiments, $R^b$ and $R^6$ combine to form a 3-6-membered nitrogen-containing heterocyclyl. In other embodiments, $R^b$ and $R^6$ combine to form a heterocyclyl as depicted in Table 1, below. The heterocyclyl ring formed by joining $R^b$ and $R^6$ can be optionally substituted with 1-5 $R^7$. (e.g., $C_{1-6}$ aliphatic or halo).

In some embodiments, $R^2$ is hydrogen. In other embodiments, $R^2$ is $C_{1-4}$ alkyl. In still other embodiments, $R^2$ is $C_{1-3}$ alkyl. In still other embodiments, $R^2$ is selected from those depicted in Table 1, below.

In some embodiments, $R^3$ is hydrogen. In other embodiments, $R^3$ is $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur; each of which is optionally substituted with 1-5 $R^7$. In some embodiments, $R^3$ is $C_{1-3}$ alkyl. In other embodiments, $R^3$ is 5-6-membered heteroaryl having 1-4 heteroatoms independently selected from nitrogen, oxygen, or sulfur.

In some embodiments, $L^1$ is a bond and $R^3$ is optionally substituted 5-10-membered heteroaryl. In some embodiments, $L^1$ is a bond and $R^3$ is

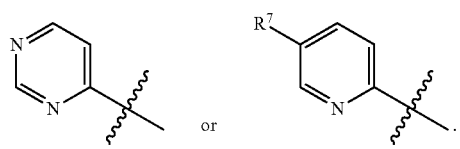

In some embodiments, $L^1$ is a bond and $R^3$ is

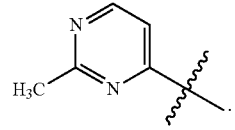

In some embodiments, $R^3$ is optionally substituted with 1, 2, 3, 4, or 5 $R^7$ independently selected from halo and $-L^3 R^8$. When $R^3$ includes one or more $R^7$ groups that is $-L^3-R^8$, in some embodiments, $L^3$ is a bond. In other embodiments, $L^3$ is $C_{1-4}$ aliphatic, —O—, —N($R^c$)—, —S—, —S(O)—, —S(O)$_2$—, —C(O)—, —C(O)O—, —C(O)N($R^c$)—, —N($R^c$)C(O)—, —N($R^+$)C(O)O—, —S(O)$_2$N$R^c$, —N($R^c$)S(O)$_2$—, —OC(O)N($R^c$)—, —N($R^c$)C(O)N($R^d$)—, —N($R^c$)S(O)$_2$N($R^d$)—, or —OC(O)—. In other embodiments, $R^c$ is H. In still other embodiments, $R^c$ is $C_{1-4}$ alkyl. In other embodiments, $R^d$ is H. In still other embodiments, $R^d$ is $C_{1-4}$ alkyl. In some embodiments, $R^8$ is hydrogen. In other embodiments, $R^8$ is $C_{1-6}$ aliphatic, 3-10-membered cycloaliphatic, phenyl, naphthyl, 3-10-membered heterocyclyl having 1-4 heteroatoms independently selected from nitrogen, oxygen, or sulfur, or 5-10-membered heteroaryl having 1-4 heteroatoms independently selected from nitrogen, oxygen, or sulfur. In still other embodiments, $R^3$ is selected from those depicted in Table 1, below.

In some embodiments, the moiety described by —NR$^2$-L$^1$-R$^3$ is selected from: —NH—C(O)OCH$_3$, —NH—C(O)CH$_3$, —NH—C(O)CH$_2$CH$_3$, —NH—C(O)CH$_2$OH, —NH$_2$,

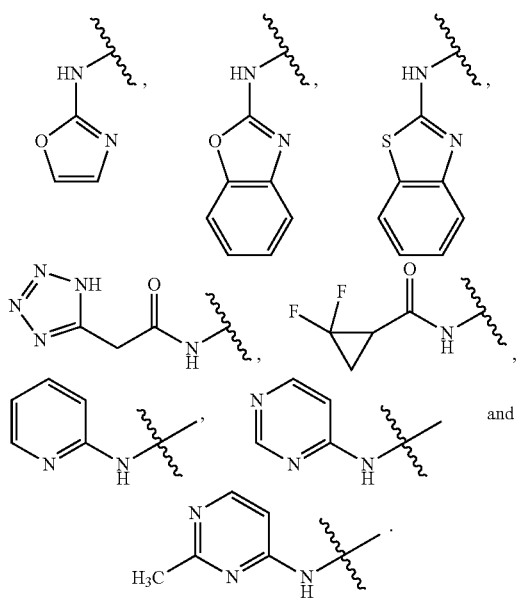

In some embodiments, the moiety described by —NR$^2$-L$^1$-R$^3$ is selected from: —NH—C(O)OCH$_3$, —NH—C(O)CH$_3$, —NH—C(O)CH$_2$CH$_3$, —NH—C(O)CH$_2$OH, —NH$_2$,

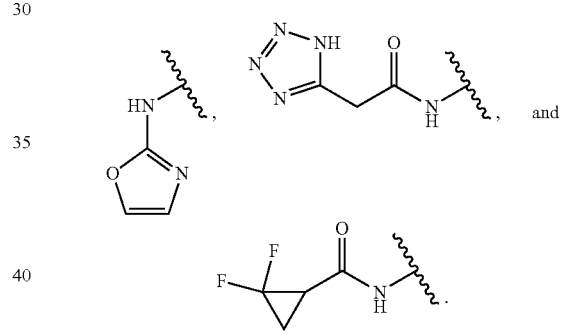

In some embodiments, the moiety described by —NR$^2$-L$^1$-R$^3$ selected from those depicted in Table 1, below.

In some embodiments, each $R^4$ is independently halo or -L$^4$-R$^9$. In some embodiments, $L^4$ is a $C_{1-4}$ alkylene chain, —O—, or —N($R^e$)—. In some embodiments, $R^e$ is hydrogen or methyl. In some embodiments, $R^9$ is hydrogen or $C_{1-3}$ alkyl. In some embodiments, $R^4$ is fluoro, chloro. $C_{1-3}$alkyl (e.g., methyl), trifluoromethyl, hydroxyl, —NH$_2$ or —NH—C$_{1-3}$ alkyl. In some embodiments, $R^4$ is substituted at the ring position between the ring nitrogen and the ring carbon connected to —N($R^1$)—. In some embodiments, each $R^4$ is independently selected from those depicted in Table 1, below.

In some embodiments, each $R^5$ is independently halo or -L$^4$-R$^9$. In some embodiments, $L^4$ is a $C_{1-4}$ alkylene chain, —O—, —N($R^e$)—. In certain embodiments, $R^e$ is hydrogen or methyl. In other embodiments, $R^9$ is hydrogen or $C_{1-3}$ alkyl. In some embodiments, each $R^5$ is independently selected from those depicted in Table 1, below.

In some embodiments, m is 0. In other embodiments, m is 1 or 2.

In some embodiments, n is 0. In other embodiments, n is 1, 2, or 3. In still other embodiments, n is 0, 1, or 2.

In some embodiments, $R^6$ is $C_{1-4}$ alkyl, 3-6-membered cycloaliphatic, phenyl, naphthyl, 3-6-membered heterocyclyl having 1-3 heteroatoms independently selected from nitrogen, oxygen, or sulfur, or 5-6-membered heteroaryl having 1-3 heteroatoms independently selected from nitrogen, oxygen, or sulfur; $R^3$ is $C_{1-3}$ alkyl; and $R^4$ is halo or $-L^4-R^9$ wherein $L^4$ is $C_{1-4}$ alkylene chain, —O—, or —N($R^e$)— where $R^e$ is hydrogen or methyl, and $R^9$ is hydrogen or $C_{1-3}$ alkyl. In other embodiments, $R^6$ is methyl, ethyl, or phenyl optionally substituted with $C_{1-3}$ alkyl, fluoro, or chloro. In still other embodiments, each $R^6$ is independently selected from those depicted in Table 1, below.

In some embodiments, the compound of formula I has a structure according to any of formulas I-A, I-B, I-C, I-D, and I-E,

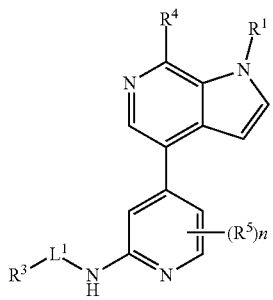

I-A

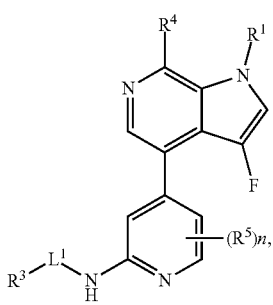

I-B

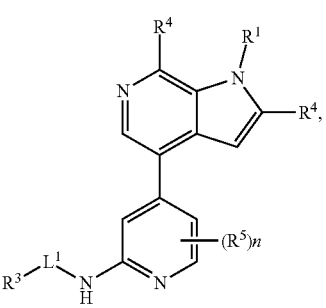

I-C

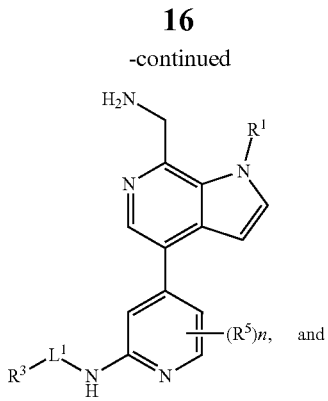

I-D

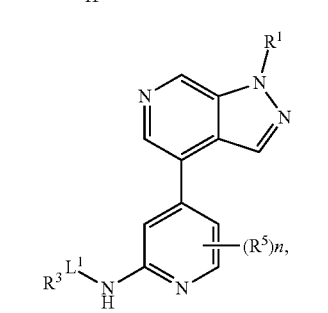

I-E or a pharmaceutically acceptable salt thereof, where $R^1$, $L^1$, $R^3$, $R^4$, $R^5$, and n are as described herein.

In some embodiments, the compound of formula I has a structure according to formula II,

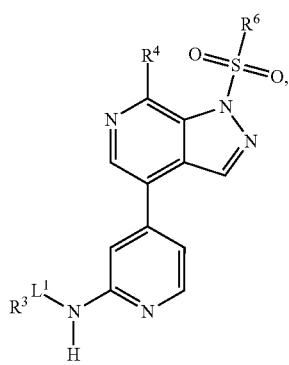

II or a pharmaceutically acceptable salt thereof, where $L^1$, $R^3$, $R^4$, and $R^6$ are as described herein.

In some embodiments, the compound of formula I has a structure according to formula III or to formula IV,

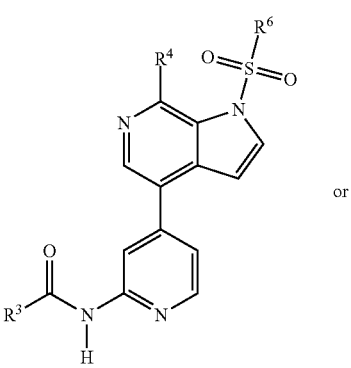

III or

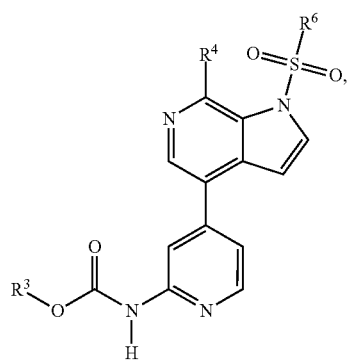

IV or a pharmaceutically acceptable salt thereof, where $R^1$, $R^4$, and $R^6$ are as described herein.

In some embodiments, the compound of formula I has a structure according to formula V or to formula VI,

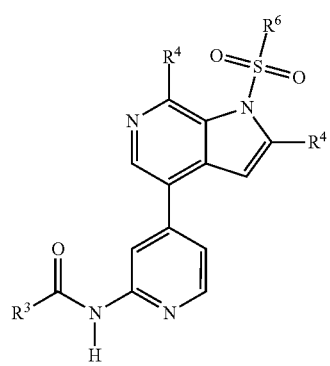

V or

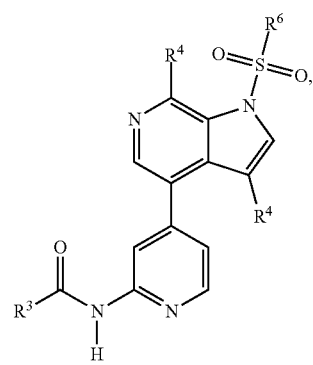

VI or a pharmaceutically acceptable salt thereof, where $R^1$, $R^4$, and $R^6$ are as described herein.

In some embodiments, the compound of formula I has a structure according to formula VII or to formula VIII,

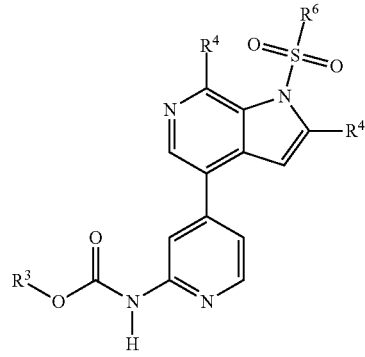

VII or

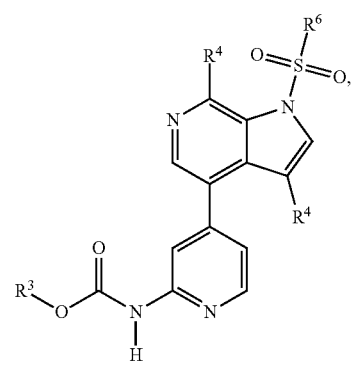

VIII or a pharmaceutically acceptable salt thereof, where $R^3$, $R^4$, and $R^6$ are as described herein.

In some embodiments, the compound of formula I has a structure according to formula IX or formula X,

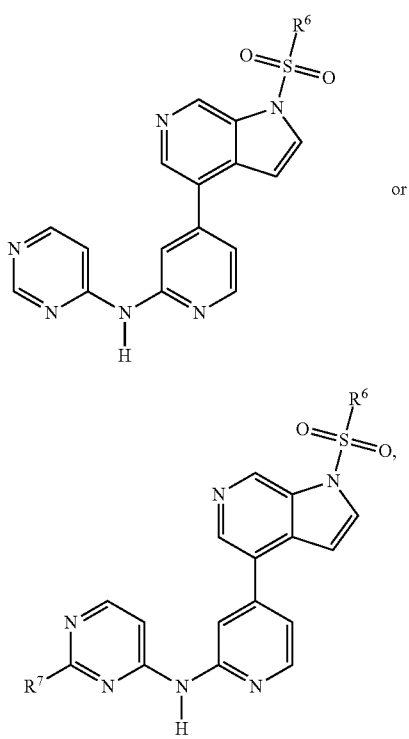

IX or

X or a pharmaceutically acceptable salt thereof, where $R^6$ and $R^7$ are as described herein.

In some embodiments, the compound of formula I has a structure according to formula XI or to formula XII,

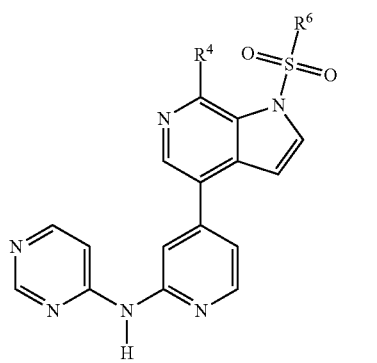

XI or

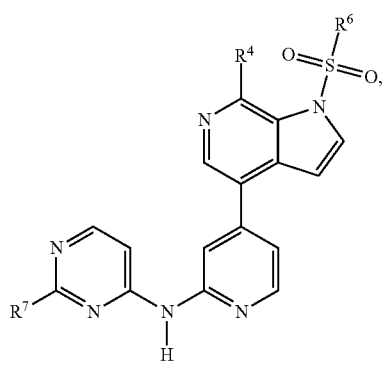

XII or a pharmaceutically acceptable salt thereof, where $R^4$, $R^6$ and $R^7$ are as described herein.

In some embodiments, the present invention provides a pharmaceutically acceptable salt thereof of any of the compounds described herein.

In other embodiments, the present invention provides a composition that includes a compound described herein, or a pharmaceutically acceptable salt, and a pharmaceutically acceptable carrier.

Exemplary compounds of the present invention are set forth in Table 1, below. In certain embodiments, the present invention provides a compound depicted in Table 1, or a pharmaceutically acceptable salt thereof.

TABLE 1

Exemplary Compounds

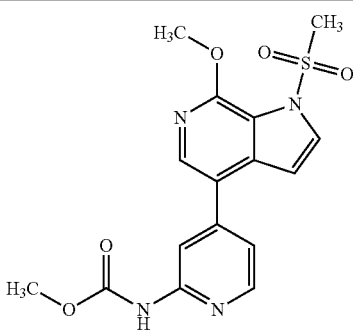

I-1

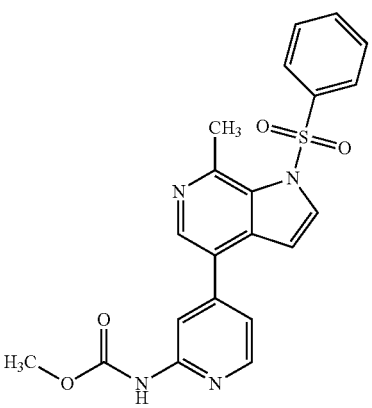

I-2

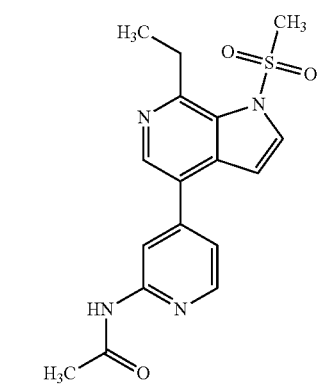

I-3

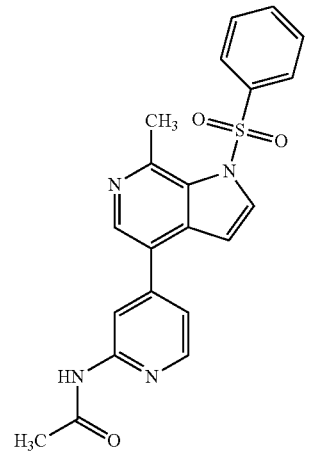

I-4

TABLE 1-continued
Exemplary Compounds
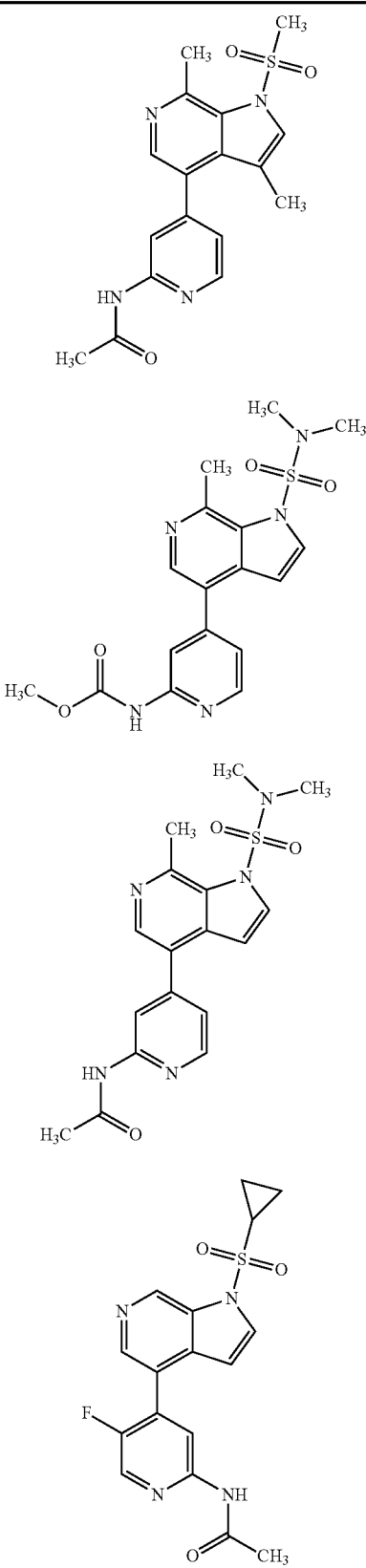
I-5
I-6
I-7
I-8
TABLE 1-continued
Exemplary Compounds
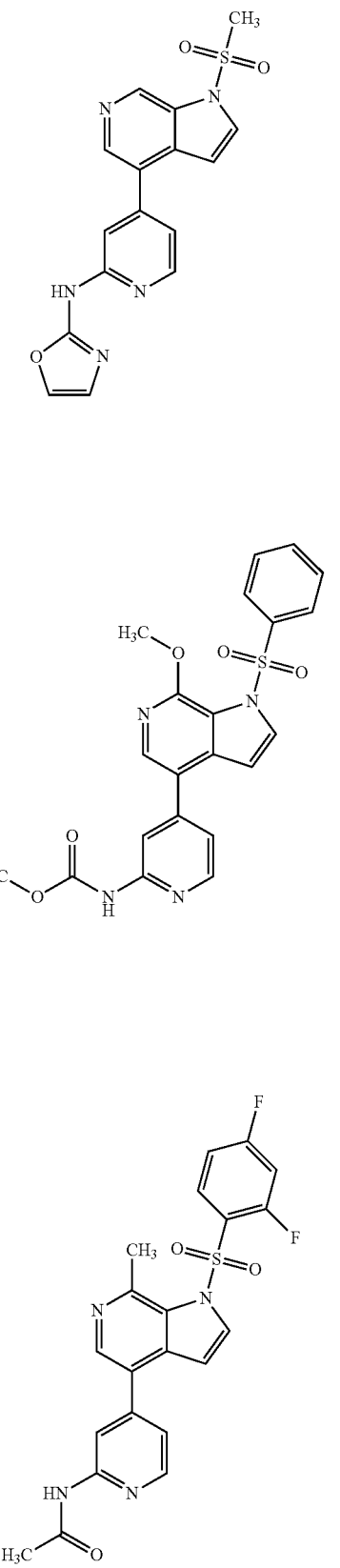
I-9
I-10
I-11

TABLE 1-continued

Exemplary Compounds

I-12, I-13, I-14, I-15, I-16, I-17, I-18

TABLE 1-continued

Exemplary Compounds

I-20

I-21

I-22

I-23

I-24

I-25

I-27

I-28

TABLE 1-continued
Exemplary Compounds
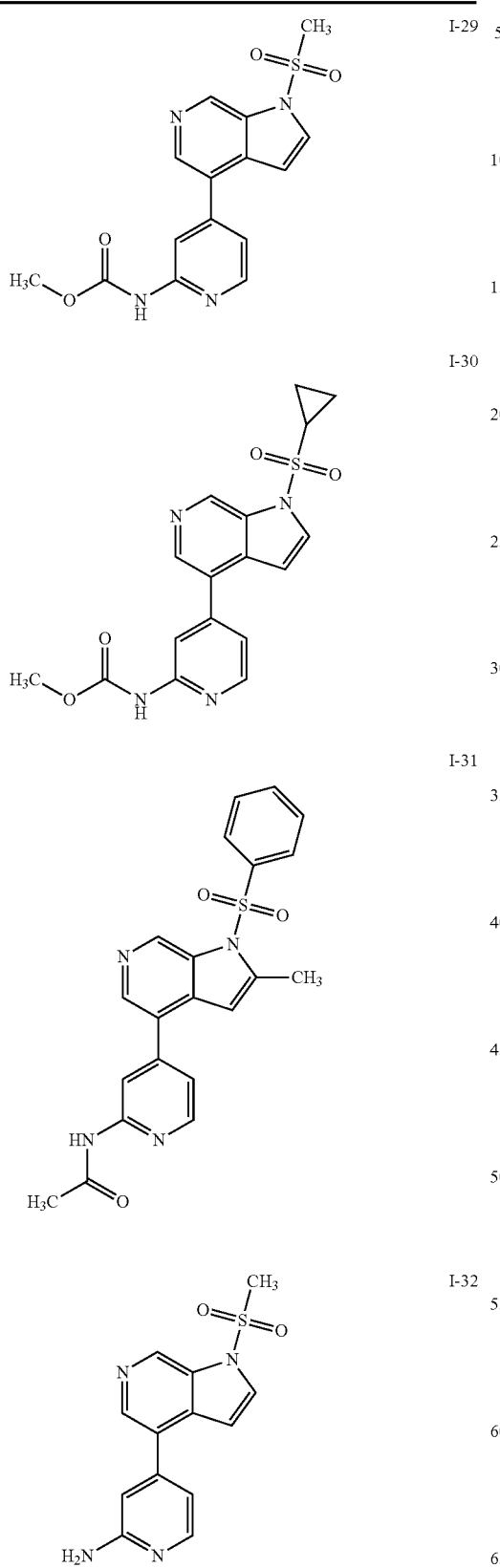
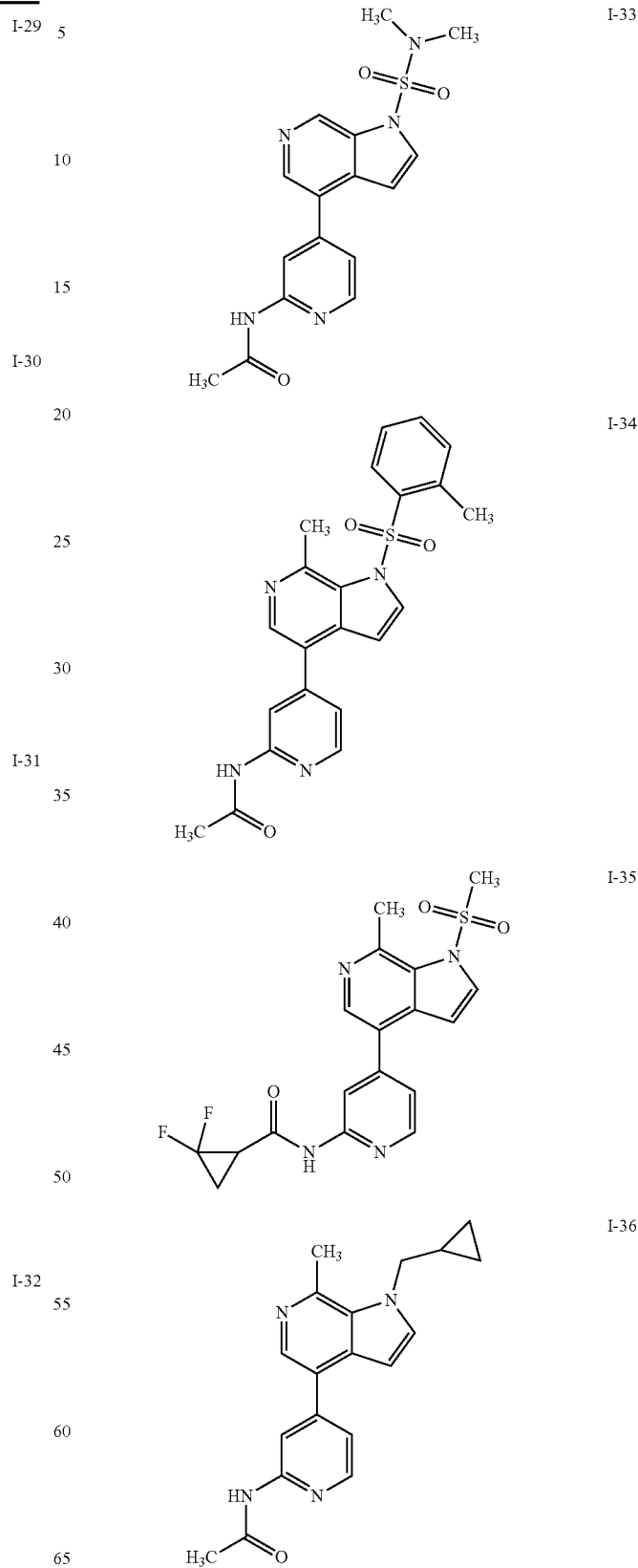

TABLE 1-continued
Exemplary Compounds
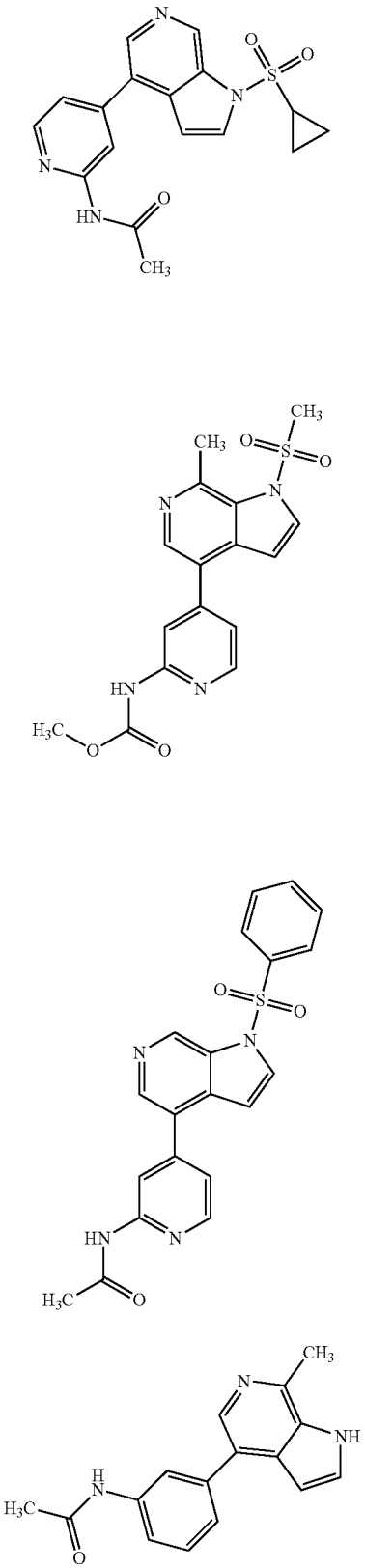
I-37
I-38
I-39
I-40
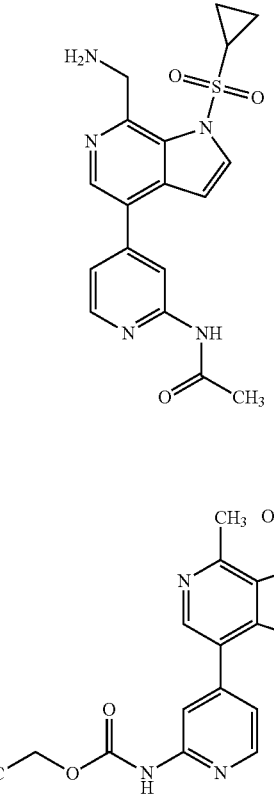
I-41
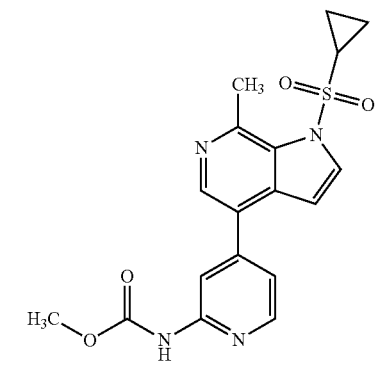
I-42
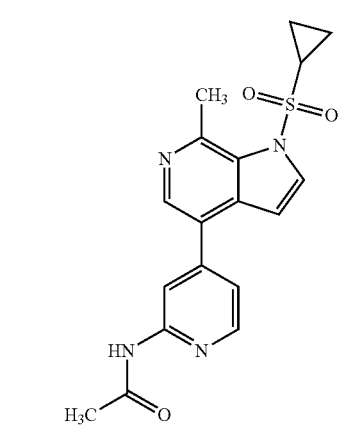
I-43
I-44

TABLE 1-continued

Exemplary Compounds

I-45

I-46

I-47

I-48

TABLE 1-continued

Exemplary Compounds

I-49

I-50

I-51

The compounds of Table 1 above may also be identified by the following chemical names in Table 2, which also shows the correspondence to the representative synthetic protocol described in the present Examples.

TABLE 2

Chemical Names and Corresponding Synthetic Example

| Compound | Example No. | Name |
| --- | --- | --- |
| I-1 | 4D | methyl {4-[7-methoxy-1-(methylsulfonyl)-1H-pyrrolo[2,3-c]pyridin-4-yl]pyridin-2-yl}carbamate |
| I-2 | 4B | methyl {4-[7-methyl-1-(phenylsulfonyl)-1H-pyrrolo[2,3-c]pyridin-4-yl]pyridin-2-yl}carbamate |
| I-3 | 3N | N-{4-[7-ethyl-1-(methylsulfonyl)-1H-pyrrolo[2,3-c]pyridin-4-yl]pyridin-2-yl}acetamide |
| I-4 | 3 | N-{4-[7-methyl-1-(phenylsulfonyl)-1H-pyrrolo[2,3-c]pyridin-4-yl]pyridin-2-yl}acetamide |
| I-5 | 3T | N-{4-[3,7-dimethyl-1-(methylsulfonyl)-1H-pyrrolo[2,3-c]pyridin-4-yl]pyridin-2-yl}acetamide |
| I-6 | 4E | methyl {4-[1-(dimethylsulfamoyl)-7-methyl-1H-pyrrolo[2,3-c]pyridin-4-yl]pyridin-2-yl}carbamate |
| I-7 | 3F | N-{4-[1-(dimethylsulfamoyl)-7-methyl-1H-pyrrolo[2,3-c]pyridin-4-yl]pyridin-2-yl}acetamide |
| I-8 | 9 | N-{4-[1-(cyclopropylsulfonyl)-1H-pyrrolo[2,3-c]pyridin-4-yl]-5-fluoropyridin-2-yl}acetamide |
| I-9 | 3J | 4-[1-(methylsulfonyl)-1H-pyrrolo[2,3-c]pyridin-4-yl]-N-(1,3-oxazol-2-yl)pyridin-2-amine |
| I-10 | 4C | methyl {4-[7-methoxy-1-(phenylsulfonyl)-1H-pyrrolo[2,3-c]pyridin-4-yl]pyridin-2-yl}carbamate |
| I-11 | 3C | N-(4-{1-[(2,4-difluorophenyl)sulfonyl]-7-methyl-1H-pyrrolo[2,3-c]pyridin-4-yl}pyridin-2-yl)acetamide |
| I-12 | 4G | methyl {4-[1-(cyclopentylsulfonyl)-7-methyl-1H-pyrrolo[2,3-c]pyridin-4-yl]pyridin-2-yl}carbamate |
| I-13 | 8 | N-(1,3-oxazol-2-yl)-4-[1-(phenylsulfonyl)-1H-pyrrolo[2,3-c]pyridin-4-yl]pyridin-2-amine |
| I-14 | 3Z | N-{4-[1-(cyclopropylsulfonyl)-3-fluoro-7-methyl-1H-pyrrolo[2,3-c]pyridin-4-yl]pyridin-2-yl}acetamide |
| I-15 | 3X | methyl {4-[1-(isobutylsulfonyl)-7-methyl-1H-pyrrolo[2,3-c]pyridin-4-yl]pyridin-2-yl}carbamate |
| I-16 | 3M | N-{4-[1-(ethylsulfonyl)-7-methyl-1H-pyrrolo[2,3-c]pyridin-4-yl]pyridin-2-yl}acetamide |
| I-17 | 4F | methyl {4-[1-(dimethylsulfamoyl)-1H-pyrrolo[2,3-c]pyridin-4-yl]pyridin-2-yl}carbamate |
| I-18 | 3P | N-{4-[1-(cyclopropylsulfonyl)-7-(dimethylamino)-1H-pyrrolo[2,3-c]pyridin-4-yl]pyridin-2-yl}acetamide |
| I-20 | 3E | N-[4-(1H-pyrrolo[2,3-c]pyridin-4-yl)pyridin-2-yl]acetamide |
| I-21 | 3H | N-{4-[1-(methylsulfonyl)-1H-pyrrolo[2,3-]pyridin-4-yl]pyridin-2-yl}acetamide |
| I-22 | 5 | N-{4-[1-(cyclopropylsulfonyl)-1H-pyrazolo[3,4-c]pyridin-4-yl]pyridin-2-yl}acetamide |
| I-23 | 3K | N-{4-[7-methyl-1-(pyrrolidin-1-ylsulfonyl)-1H-pyrrolo[2,3-c]pyridin-4-yl]pyridin-2-yl}acetamide |
| I-24 | 6 | N-{4-[2-ethyl-1-(phenylsulfonyl)-1H-pyrrolo[2,3-c]pyridin-4-yl]pyridin-2-yl}acetamide |
| I-25 | 10B | ethyl {4-[1-(methylsulfonyl)-1H-pyrrolo[2,3-c]pyridin-4-yl]pyridin-2-yl}carbamate |
| I-27 | 12 | N-{4-[1-(cyclopropylsulfonyl)-1H-pyrrolo[2,3-c]pyridin-4-yl]pyridin-2-yl}-2-(1H-tetrazol-5-yl)acetamide |
| I-28 | 7 | methyl {4-[1-(phenylsulfonyl)-1H-pyrrolo[2,3-c]pyridin-4-yl]pyridin-2-yl}carbamate |
| I-29 | 4A | methyl {4-[1-(methylsulfonyl)-1H-pyrrolo[2,3-c]pyridin-4-yl]pyridin-2-yl}carbamate |
| I-30 | 4H | methyl {4-[1-(cyclopropylsulfonyl)-1H-pyrrolo[2,3-c]pyridin-4-yl]pyridin-2-yl}carbamate |
| I-31 | 6 | N-{4-[2-methyl-1-(phenylsulfonyl)-1H-pyrrolo[2,3-c]pyridin-4-yl]pyridin-2-yl}acetamide |
| I-32 | 3U | 4-[1-(methylsulfonyl)-1H-pyrrolo[2,3-c]pyridin-4-yl]pyridin-2-amine |
| I-33 | 3V | N-{4-[1-(dimethylsulfamoyl)-1H-pyrrolo[2,3-c]pyridin-4-yl]pyridin-2-yl}acetamide |
| I-34 | 3O | N-(4-{7-methyl-1-[(2-methylphenyl)sulfonyl]-1H-pyrrolo[2,3-c]pyridin-4-yl}pyridin-2-yl)acetamide |
| I-35 | 11 | (rac)-2,2-difluoro-N-{4-[7-methyl-1-(methylsulfonyl)-1H-pyrrolo[2,3-c]pyridin-4-yl]pyridin-2-yl}cyclopropanecarboxamide |
| I-36 | 3G | N-{4-[1-(cyclopropylmethyl)-7-methyl-1H-pyrrolo[2,3-c]pyridin-4-yl]pyridin-2-yl}acetamide |
| I-37 | 3L | N-{4-[1-(cyclopropylsulfonyl)-1H-pyrrolo[2,3-c]pyridin-4-yl]pyridin-2-yl}acetamide |
| I-38 | 3W | methyl {4-[7-methyl-1H-pyrrolo[2,3-c]pyridin-4-yl]pyridin-2-yl}carbamate |
| I-39 | 3D | N-{4-[1-(phenylsulfonyl)-1H-pyrrolo[2,3-c]pyridin-4-yl]pyridin-2-yl}acetamide |
| I-40 | 3I | N-[4-(7-methyl-1H-pyrrolo[2,3-c]pyridin-4-yl)pyridin-2-yl]acetamide |
| I-41 | 13 | N-{4-[7-(aminomethyl)-1-(cyclopropylsulfonyl)-1H-pyrrolo[2,3-c]pyridin-4-yl]pyridin-2-yl}acetamide |

TABLE 2-continued

Chemical Names and Corresponding Synthetic Example

| Compound | Example No. | Name |
|---|---|---|
| I-42 | 10A | ethyl {4-[1-(cyclopropylsulfonyl)-7-methyl-1H-pyrrolo[2,3-c]pyridin-4-yl]pyridin-2-yl}carbamate |
| I-43 | 4 | methyl {4-[1-(cyclopropylsulfonyl)-7-methyl-1H-pyrrolo[2,3-c]pyridin-4-yl]pyridin-2-yl}carbamate |
| I-44 | 3B | N-{4-[1-(cyclopropylsulfonyl)-7-methyl-1H-pyrrolo[2,3-c]pyridin-4-yl]pyridin-2-yl}acetamide |
| I-45 | 3A | N-{4-[7-methyl-1-(methylsulfonyl)-1H-pyrrolo[2,3-c]pyridin-4-yl]pyridin-2-yl}acetamide |
| I-46 | 3Y | N-{4-[3-fluoro-7-methyl-1-(methylsulfonyl)-1H-pyrrolo[2,3-c]pyridin-4-yl]pyridin-2-yl}acetamide |
| I-47 | 10 | ethyl {4-[7-methyl-1-(phenylsulfonyl)-1H-pyrrolo[2,3-c]pyridin-4-yl]pyridin-2-yl}carbamate |
| I-48 | 10C | N-{4-[1-(cyclopropylsulfonyl)-7-methyl-1H-pyrrolo[2,3-c]pyridin-4-yl]pyridin-2-yl}-2-hydroxyacetamide |
| I-49 | 14 | N-{4-[1-(cyclopropylsulfonyl)-1H-pyrrolo[2,3-c]pyridin-4-yl]pyridin-2-yl}pyrimidin-4-amine |
| I-50 | 14 | N-[4-(1H-pyrrolo[2,3-c]pyridin-4-yl)pyridin-2-yl]pyrimidin-4-amine |
| I-51 | 15 | 2-methyl-N-[4-(7-methyl-1H-pyrrolo[2,3-c]pyridin-4-yl)pyridin-2-yl]pyrimidin-4-amine |

General Synthetic Methods and Intermediates:

The compounds of the present invention can be prepared by methods known to one of ordinary skill in the art and/or by reference to the schemes shown below and the synthetic examples that follow. Exemplary synthetic routes are set forth in the Schemes below, and in the Examples.

One of ordinary skill in the art will recognize that numerous variations in reaction conditions including variations in solvent, reagents, catalysts, reaction temperatures and times are possible for each of the reactions described. Variation of order of synthetic steps and alternative synthetic routes are also possible.

Scheme 1: General method for the preparation of compounds I-A.

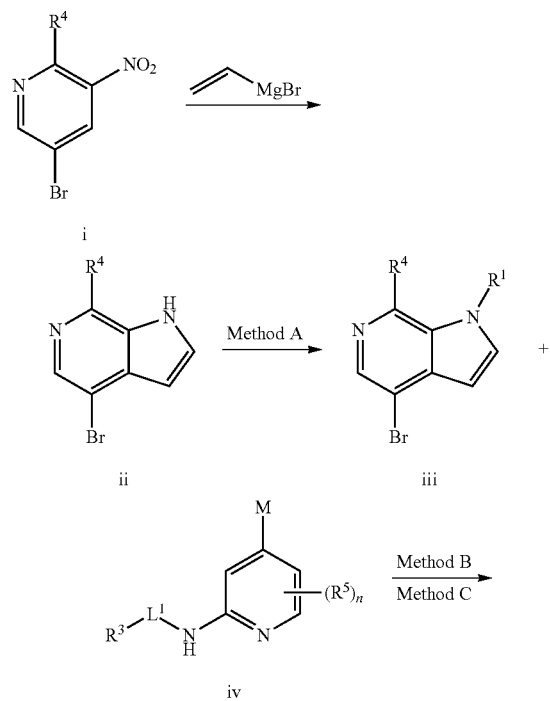

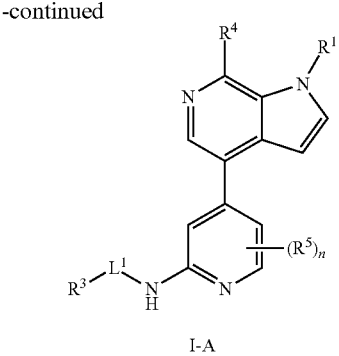

I-A

Scheme 1 describes a method for the preparation of compounds of formula I-A. Starting from a substituted pyridine i, reaction with a reagent such as vinylmagnesium bromide in a solvent such as THF or diethyl ether can be used to provide compound ii. Reaction of compounds ii under Method A leads to compounds iii. Method A can refer to reaction with electrophiles, such as acid halides, sulfonyl halides or alkyl halides in the presence of a suitable base. Compounds iii can then react with compounds iv using Method B or Method C to provide compounds I-A. Method B (for similar procedures, see A. Suzuki, *J. Organometallic Chem.* 1999, 576, 147-168; Pagliaro et al., *Org. Process Res. Dev.* 2012, 16, 117-122) can refer to the coupling reaction of an aryl or heteroaryl halide with an appropriate boronic acid or boronic ester under suitable conditions, for example a catalyst such as $PdCl_2$(amphos), $Pd(PPh_3)_4$, SiliaCat DPP-Pd, $Pd(dppf)_2Cl_2$, and XPhosG3/XPhos, a base such as $Na_2CO_3$, $Cs_2CO_3$, $K_3PO_4$ in an appropriate solvent, such as DME or dioxane, at elevated temperature or under microwave irradiation. Method C (for a review of the Stille coupling, see W. J. Scott et al., "The Stille Reaction" Organic Reations, 2004, Wiley: Online) can refer to the coupling reaction of an aryl or heteroaryl bromide with an appropriate aryl or heteroaryl stannane under suitable conditions, for example $Pd(PPh_3)_4$, CuI, LiCl in an appropriate solvent, such as dioxane at elevated temperature. In addition, compounds of formula I-A where -$L^1$-$R^3$ is H, treatment with an acid or alkyl halide under basic conditions can provide other compounds I-A, where -$L^1$-$R^3$ is an acyl, carbamate or alkyl group.

Scheme 2: Alternate method for the preparation of compounds I-A.

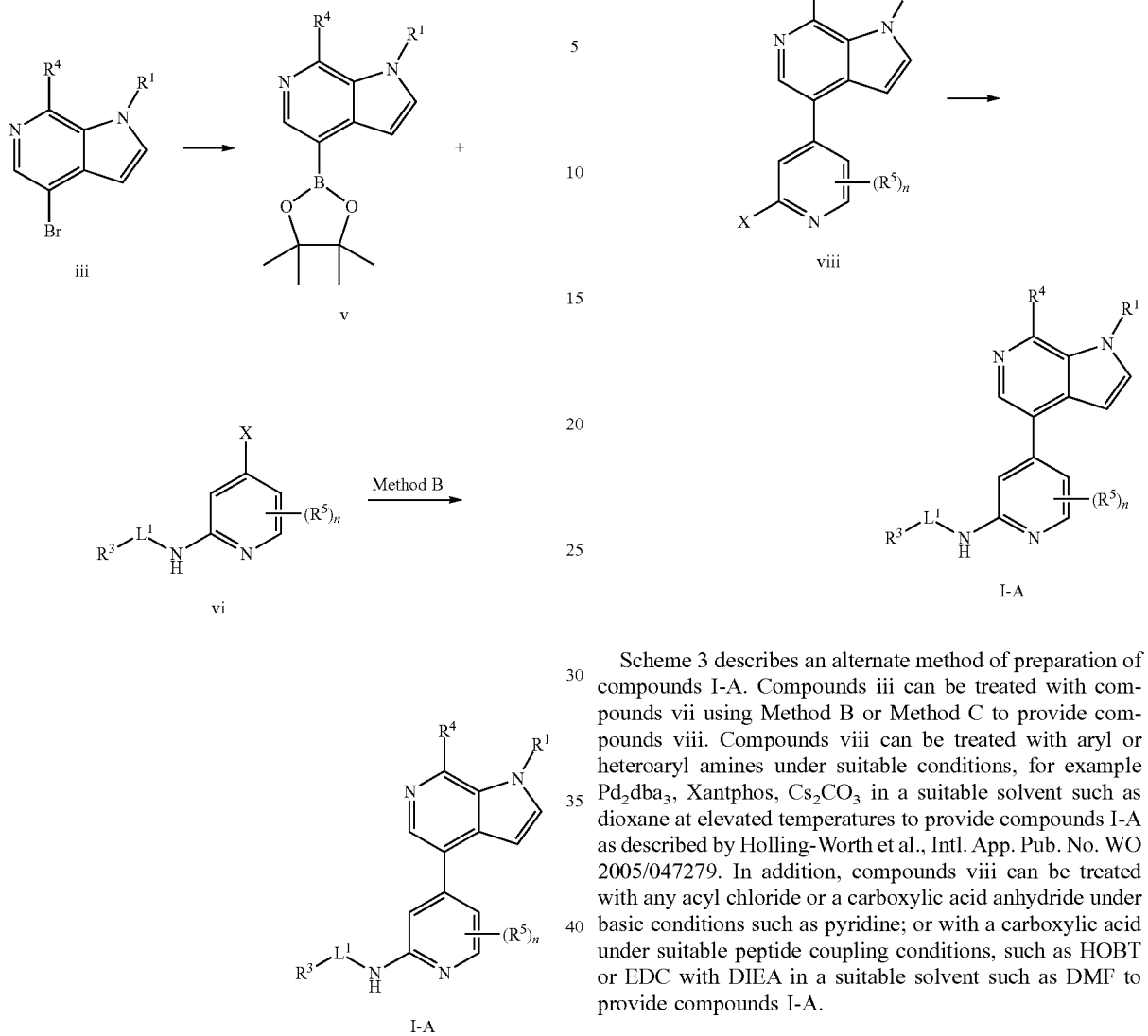

Scheme 2 describes an alternate method for preparation of compounds I-A. Compound iii can be treated with bispinacolato diboron under suitable conditions, for example Pd(dppf)Cl$_2$, KOAc in an appropriate solvent such as dioxane at elevated temperatures to provide compounds v. Compounds v can be transformed to compounds I-A through reaction with compounds vi using Method B.

Scheme 3: Alternate method for the preparation of compounds I-A.

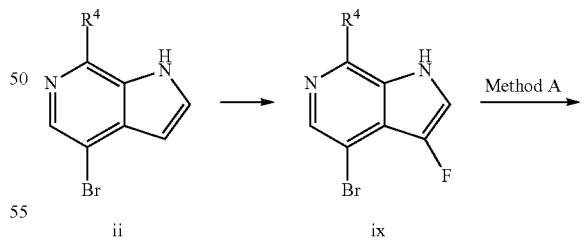

Scheme 3 describes an alternate method of preparation of compounds I-A. Compounds iii can be treated with compounds vii using Method B or Method C to provide compounds viii. Compounds viii can be treated with aryl or heteroaryl amines under suitable conditions, for example Pd$_2$dba$_3$, Xantphos, Cs$_2$CO$_3$ in a suitable solvent such as dioxane at elevated temperatures to provide compounds I-A as described by Holling-Worth et al., Intl. App. Pub. No. WO 2005/047279. In addition, compounds viii can be treated with any acyl chloride or a carboxylic acid anhydride under basic conditions such as pyridine; or with a carboxylic acid under suitable peptide coupling conditions, such as HOBT or EDC with DIEA in a suitable solvent such as DMF to provide compounds I-A.

Scheme 4: General method for the preparation of compounds I-B.

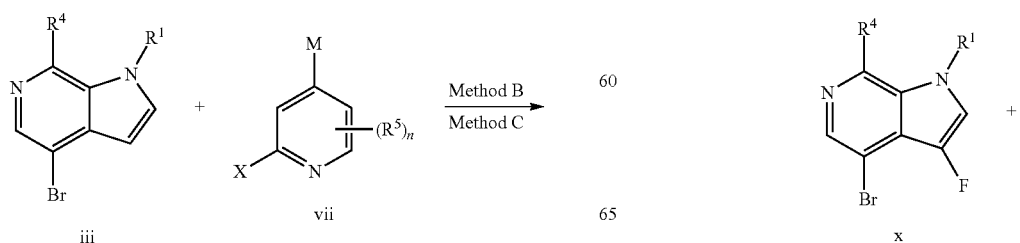

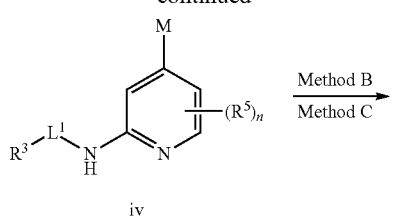

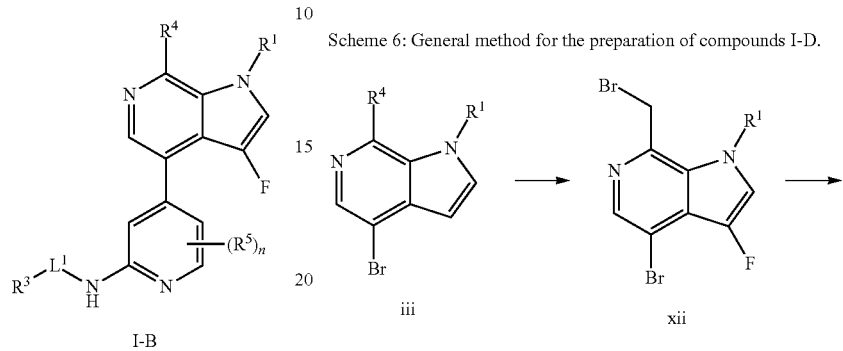

Scheme 4 describes the preparation of fluoro substituted compounds I-B. Compounds ii can be treated with Selectfluor in an appropriate solvent, such as acetonitrile, to provide compounds ix. Compounds ix can be converted to compounds x using Method A. Compounds x can be further transformed to compounds I-B using Method B or Method C.

Scheme 5: General method for the preparation of compounds I-C.

Scheme 5 describes a method of preparing compounds I-C. Compounds iii can be treated with an appropriate electrophile, such as an alkyl halide, under suitable conditions, such as LDA in a suitable solvent such as THF to prepare compounds xi. Treatment of compounds xi using Method B or Method C effects the transformation to compounds I-C.

Scheme 6: General method for the preparation of compounds I-D.

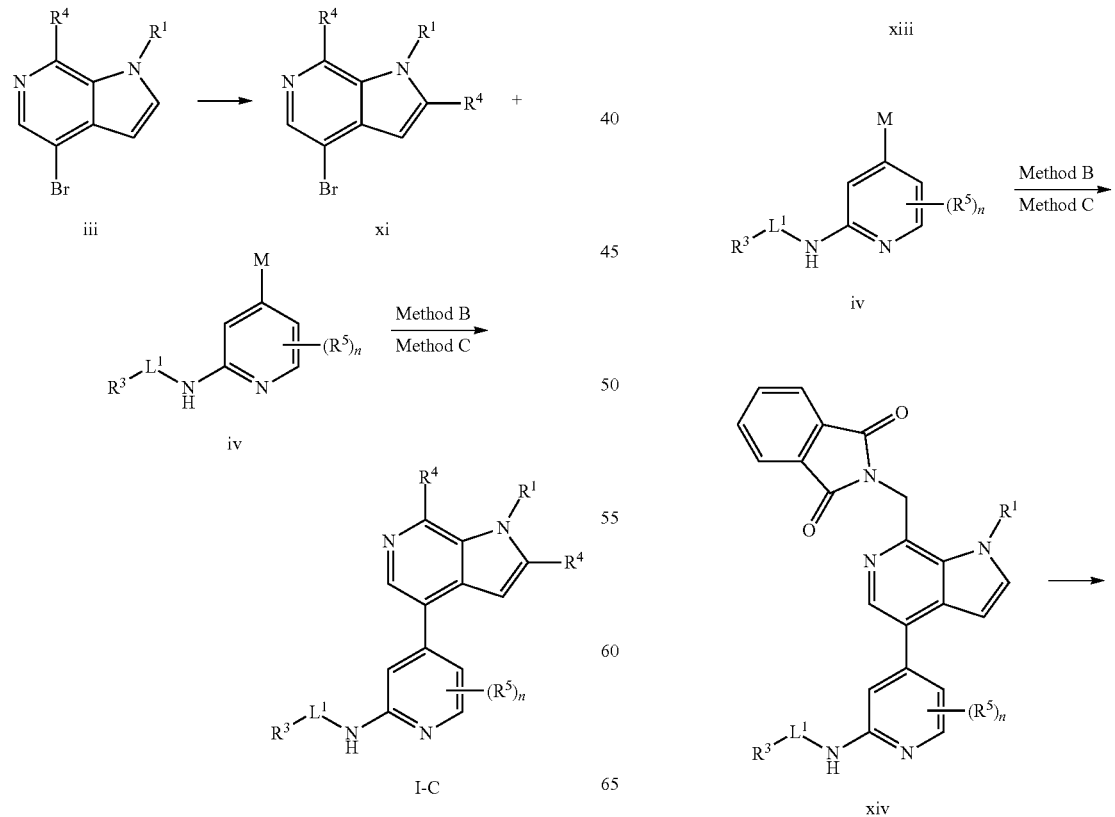

-continued

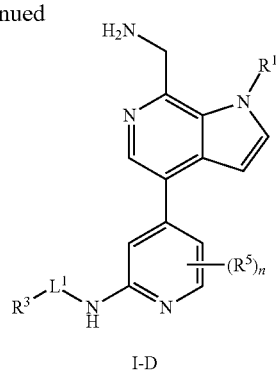

I-D

Scheme 6 describes a method of preparing compounds I-D. In the case of compounds iii where $R^4$ is Me, treatment under suitable conditions such as NBS, benzoyl peroxide in a suitable solvent such as carbon tetrachloride can provide compounds xii. Compounds xiii can be prepared by reaction of compounds xii under suitable conditions, such as potassium phthalimide in a suitable solvent such as DMF. Compounds xiii can be treated with iv using Method B or Method C to provide compounds xiv. Compounds I-D can be prepared by treatment of compounds xiv under suitable conditions, such as hydrazine in a suitable solvent, such as methanol.

Scheme 7: General method for the preparation of compounds I-E.

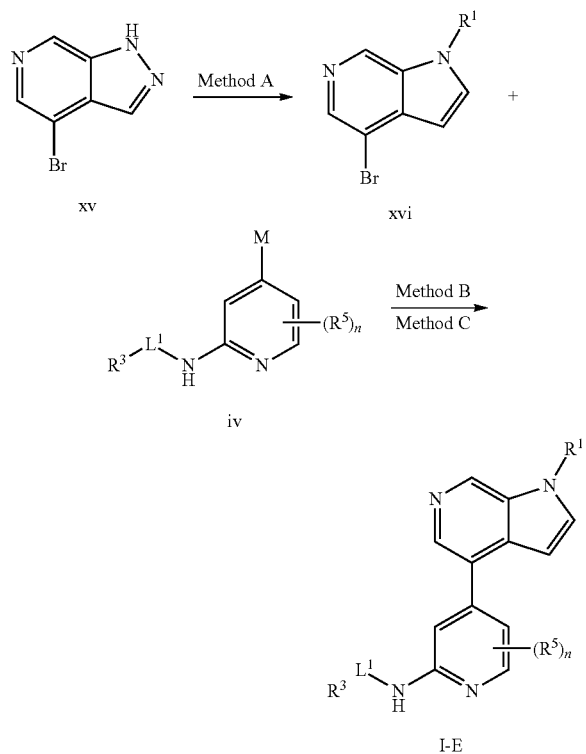

Scheme 7 describes a method of preparing compounds I-E. Pyrazolopyridines xv can be treated using Method A to provide compounds xvi. Compounds xvi can be treated with compounds iv using Method B or Method C to provide compounds I-E.

4. Uses. Formulation and Administration

As discussed above, the present invention provides compounds that are useful as inhibitors of VPS34, and thus the present compounds are useful for treating inflammatory, cardiovascular, proliferative disorders (such as tumor and/or cancerous cell growth) mediated by VPS34. In particular, the compounds can be useful in the treatment of cancers in a subject, including, but not limited to, lung and bronchus, including non-small cell lung cancer (NSCLC), squamous lung cancer, brochioloalveolar carcinoma (BAC), adenocarcinoma of the lung, and small cell lung cancer (SCLC); prostate, including androgen-dependent and androgen-independent prostate cancer; breast, including metastatic breast cancer; pancreas; colon and rectum; thyroid; liver and intrahepatic bile duct; hepatocellular; gastric; endometrial; melanoma; kidney; and renal pelvis, urinary bladder; uterine corpus; uterine cervix; ovary, including progressive epithelial or primary peritoneal cancer; multiple myeloma; esophagus; acute myelogenous leukemia (AML); chronic myelogenous leukemia (CML), including accelerated CML and CML blast phase (CML-BP); lymphocytic leukemia; myeloid leukemia; acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma, including diffuse large B-cell lymphoma (DLBCL); T-cell lymphoma; multiple myeloma (MM); amyloidosis; Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes; brain, including glioma/glioblastoma, anaplastic oligodendroglioma, and adult anaplastic astrocytoma; neuroendocrine, including metastatic neuroendocrine tumors; head and neck, including, e.g., squamous cell carcinoma of the head and neck, and nasopharyngeal cancer; oral cavity; and pharynx; small intestine; bone; soft tissue sarcoma; and villous colon adenoma.

In some embodiments, compounds of the invention can be suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention can be suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. To clarify, the present invention also includes the corresponding N-oxide of the compounds of formula I.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of VPS34.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound of formula I, or a pharmaceutical composition containing the same to a subject in need thereof. In certain embodiments of the present invention an "effective amount" of the compound of formula I or pharmaceutical composition containing the same is that amount effective for treating a proliferative, inflammatory, or cardiovascular disorder, or is that amount effective for treating cancer. In other embodiments, an "effective amount" of a compound of formula I is an amount which inhibits activity of VPS34 and thereby blocks the resulting signaling cascades that lead to the abnormal activity of members of such cascades (e.g., growth factors, receptor tyrosine kinases, protein serine/threonine kinases, G protein coupled receptors and phospholipid kinases and phosphatases). Still in other embodiments, an "effective amount" of a compound of formula I is an amount which inhibits activity of VPS34 and thereby leads to abnormal activity of degradation pathways mediated by the proteasome or lysosome.

The compounds and compositions, according to the method of the present invention, may be administered using any amount and any route of administration effective for treating the disease. The exact amount required will vary from subject to subject, depending on the species, age, and general condition of the subject, the severity of the disorder, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease being treated. In certain embodiments, the compounds of the invention may be administered orally or parenterally at dosage levels of about 0.01 mg/kg to about 200 mg/kg (e.g., from about 0.1 mg/kg to about 50 mg/kg or from about 1 mg/kg to about 25 mg/kg), of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Compounds of this invention can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the compounds of this invention may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents. In some embodiments, the additional therapeutic agent is selected from other inhibitors of VPS34. In other embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Those additional agents may be administered separately from a provided combination therapy, as part of a multiple dosage regimen. Alternatively, those agents may be part of a single dosage form, mixed together with a compound of this invention in a single composition. If administered as part of a combination therapy, the two therapeutic agents may be submitted simultaneously, sequentially, or intermittently.

Combination therapy can be used for any of the therapeutic indications described herein. In some embodiments, the combination therapy is for the treatment of a proliferative disorder (e.g., cancer) in a patient. In some embodiments, the proliferative disorder is breast cancer, bladder cancer, colon cancer, glioma, glioblastoma, lung cancer, hepatocellular cancer, gastric cancer, melanoma, squamous cell carcinoma, head and neck cancer, thyroid cancer, endometrial cancer, renal cancer, cervical cancer, pancreatic cancer, esophageal cancer, prostate cancer, brain cancer, or ovarian cancer. In some embodiments, the proliferative disorder is breast cancer, pancreatic cancer, head and neck cancer, non-small-cell lung carcinoma (NSCLC), colon cancer, renal cell carcinoma, squamous cell carcinoma, or thyroid cancer. In other embodiments, the proliferative disorder is breast cancer, pancreatic cancer, head and neck cancer, non-small-cell lung carcinoma (NSCLC), or colon cancer.

As used herein, the term "combination," "combined." and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form.

Another aspect of the invention relates to inhibiting VPS34, activity in a biological sample or a patient, which method comprises administering to the patient, or contacting said biological sample with a compound described herein, or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where VPS34 kinase plays a role.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.
Definitions
AA LCMS method using ammonium acetate
Ac acetyl
ACN acetonitrile
AcOH acetic acid
BOC tert-butoxycarbonyl
t-Bu tert-butyl
C Celsius
dba dibenzylideneacetone
DCE dichloroethane
DCM dichloromethane
DIEA diisopropylethylamine
DMAP 4-dimethylaminopyridine
DME 1,2-dimethoxyethane
DMF dimethylformamide
DMF-DMA dimethylformamide dimethylacetal
dppf 1,1'-bis(diphenylphosphino)ferrocene
DMSO dimethylsulfoxide
EDC N-(3-dimethylaminopropyl)-M-ethylcarbodiimide
Et ethyl
EtOAc ethyl acetate FA LCMS method using formic acid
h hours
HPLC high pressure liquid chromatography
HATU O-(7-azabenzotriazol-1-yl)-N,N,N',N'-tetramethyluronium hexafluorophosphate
HMPT N-[bis(dimethylamino)phosphoryl]-N-methyl-methanamine
HOBt 1-hydroxybenzotriazole
$IC_{50}$ inhibitory concentration 50%
KOH potassium hydroxide
LCMS liquid chromatography mass spectrometry
LDA lithium bis(trimethylsilyl)azanide
m/z mass to charge
Me methyl
MeOH methanol
MHz mega hertz
min minutes
mpk mg/kg
MS mass spectrum
MTBE methyl tert-butyl ether
NBS N-bromosuccinimide
NCS N-chlorosuccinimide
PCC pyridinium chlorochromate
psi pounds per square inch
rac racemic mixture
rt room temperature
SEM silylethoxymethyl
SiliaCat DPP-Pd diphenylphosphine palladium (II) heterogeneous silica-based catalyst
STAB sodium triacetoxyborohydride
TEA triethylamine
TFA trifluoroacetic acid
THF tetrahydrofuran
TBAF tetrabutylammoniumfluoride
TBTU O-(benzotriazol-1-yl)-N,N,N',N'-tetramethyluronium tetrafluoroborate
TMS trimethylsilyl
UPLC ultra performance liquid chromatography
Xantphos 4,5-bis(diphenylphosphino)-9,9-dimethylxanthene
Xphos 2-dicyclohexylphosphino-2',4',6'-triisopropylbiphenyl
XPhosG3 (2-dicyclohexylphosphino-2',4',6'-triisopropyl-1,1'-biphenyl)[2-(2'-amino-1,1'-biphenyl)]palladium(II) methanesulfonate Analytical LCMS Methods
NMR Conditions:

$^1$H NMR spectra are run on a 400 MHz Bruker or Varian spectrometer unless otherwise stated.

LCMS spectra were recorded on a Hewlett-Packard HP1100 or Agilent 1100 Series LC system connected to a Micromass mass spectrometer using reverse phase C18 columns. Various gradients and run times were selected in order to best characterize the compounds. Mobile phases were based on ACN/water gradients and contained either 0.1% formic acid (methods indicated FA) or 10 mM ammonium acetate (methods indicated AA). One example of a solvent gradient that was used was 100% mobile phase A (mobile phase A=99% water+1% ACN+0.1% formic acid) to 100% mobile phase B (mobile phase B=95% ACN+5% water+0.1% formic acid) at a flow rate of 1 mL/min for a 16.5 min run.

In some cases, LCMS spectra were recorded on an Agilent 1290 Infinity UPLC system connected to an Agilent 6130 mass spectrometer, a Waters Acquity UPLC system connected to a Waters Acquity SQ mass spectrometer, or an Agilent 1100 Series HPLC system connected to a Waters Micromass ZQ mass spectrometer using reverse phase C18 columns. Various gradients and run times were selected in order to best characterize the compounds. Mobile phases were based on ACN/water gradients and contained either 0.1% formic acid (methods indicated FA) or 10 mM ammonium acetate (methods indicated AA). One example of a solvent gradient that was used was 95% mobile phase A (mobile phase A=99% water+1% ACN+0.1% formic acid) to 100% mobile phase B (mobile phase B=95% ACN+5% water+0.1% formic acid) at a flow rate of 0.5 mL/min for a 5 min run.

One of ordinary skill in the art will recognize that modifications of the gradient, column length, and flow rate are possible and that some conditions may be more suitable for compound characterization than others, depending on the chemical species being analyzed.

Example 1: Synthesis of Intermediate Stannanes and Boronic Esters

N-[4-(4,4,5,5-tetramethyl-1,3,2-dioxaborolan-2-yl)pyridin-2-yl]acetamide

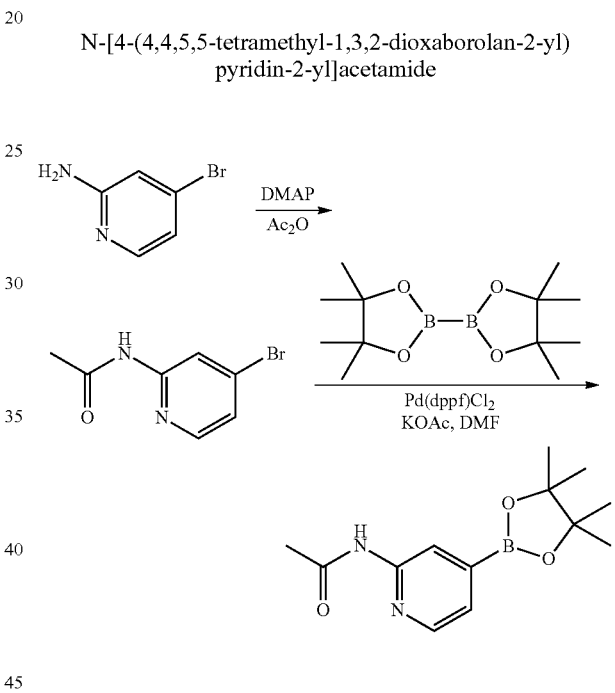

Step 1: N-(4-bromopyridin-2-yl)acetamide

To a solution of 4-bromopyridin-2-amine (12.0 g, 69.4 mmol) in acetic anhydride (240 mL) was added DMAP (0.0847 g, 0.694 mmol). The reaction mixture was allowed to stir at 140° C. for 3 h and then allowed to cool to rt. Ice water was added and the pH of the mixture was adjusted to 8.5 by the addition of concentrated $NH_4OH$. The solid which precipitated was filtered, washed with cold water and hexanes, and dried to give N-(4-bromopyridin-2-yl)acetamide (13.3 g, 89%) as a white solid.

Step 2: N-[4-(4,4,5,5-tetramethyl-1,3,2-dioxaborolan-2-yl)pyridin-2-yl]acetamide To a mixture of N-(4-bromopyridin-2-yl)acetamide (17.2 g, 80 mmol), 4,4,4',4',5,5,5',5'-octamethyl-2,2'-bi-1,3,2-dioxaborolane (26.4 g, 104 mmol), Pd(dppf)$Cl_2$ (11.7 g, 16 mmol) and KOAc (23.6 g, 240 mmol) under an atmosphere of nitrogen was added anhydrous DMF (1500 mL). The mixture was allowed to stir at 80° C. for 3.5 h. The solvent was removed and the residue was diluted with EtOAc (1000 mL). Activated carbon (100 g) was added. The slurry was heated at reflux for 5 min and then filtered. The organic solution was concentrated and the residue was recrystallized from EtOAc to give N-[4-(4,4,5,5-tetramethyl-1,3,2-dioxaborolan-2-yl)pyridin-2-yl]acetamide (6.1 g, 29%) as a white solid. $^1$H NMR (400 MHz, DMSO-$d_6$): δ 1.29 (s, 12H), 2.09 (s, 3H), 7.24 (dd, J=6.0, 1.2 Hz, 1H), 8.30-8.33 (m, 2H), 10.47 (br s, 1H).

(rac)-2,2-difluoro-N-(4-(4,4,5,5-tetramethyl-1,3,2-dioxaborolan-2-yl)pyridin-2-yl) cyclopropanecarboxamide

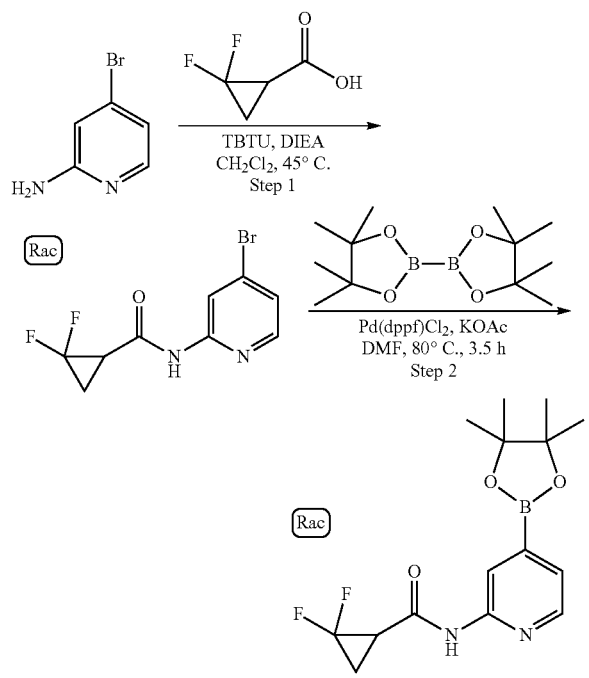

Step 1: (rac)-N-(4-bromopyridin-2-yl)-2,2-difluorocyclopropanecarboxamide

To a solution of (rac)-2,2-difluorocyclopropanecarboxylic acid (10.0 g, 82 mmol) in DCM (250 mL) was added N,N-diisopropylethylamine (53 g, 409 mmol), TBTU (60 g, 185 mmol) and 4-bromopyridin-2-amine (18.4 g, 106 mmol). The reaction mixture was heated at 45° C. for 17 h. To the reaction mixture was added water (500 mL) and the aqueous layer was extracted with EtOAc (3×300 mL). The organic layers were combined and washed with brine, dried, and concentrated in vacuo. The residue was purified by column chromatography to give a white solid determined to be the desired (rac)-N-(4-bromopyridin-2-yl)-2,2-difluorocyclopropanecarboxamide (10 g, 44%) as a racemic mixture. $^1$H NMR (400 MHz, CDCl$_3$): δ 1.33 (s, 12H), 1.76 (m, 1H), 2.25 (m, 1H), 2.47 (m, 1H), 7.42 (d, 1H, J=4.8 Hz), 8.31 (d, 1H, J=4.8 Hz), 8.54 (s, 1H), 8.99 (s, 1H).

Step 2: (rac)-2,2-difluoro-N-(4-(4,4,5,5-tetramethyl-1,3,2-dioxaborolan-2-yl)pyridin-2-yl) cyclopropanecarboxamide To a solution of (rac)-N-(4-bromopyridin-2-yl)-2,2-difluorocyclopropanecarboxamide (8.0 g, 28.9 mmol) in 1,4-dioxane (85 mL) under an atmosphere of nitrogen was added bis(pinacolato)diboron (9.5 g, 37.5 mmol), KOAc (8.4 g, 87.0 mmol) and Pd(dppf)Cl$_2$. The reaction mixture was heated at 75° C. for 12 hours. The reaction mixture was filtered and washed with EtOAc (2×100 mL). To the filtrate was added water (500 mL) and the aqueous layer was extracted with EtOAc (2×200 mL). The combined organic layers were dried over Na$_2$SO$_4$ and concentrated by rotary evaporation. To the residue was added EtOAc (200 mL) and activated carbon (25.5 g). The mixture was stirred at 90° C. for 1 h and then filtered, rinsing with hot EtOAc (2×50 mL). The filtrated was concentrated by rotary evaporation, then taken up in EtOAc (10 mL) and petroleum ether (50 mL). The mixture was stirred for 5 min, filtered and concentrated. The residue was again taken up in EtOAc (5 mL) and petroleum ether (25 mL), stirred for 5 min, filtered and concentrated to provide (rac)-2,2-difluoro-N-(4-(4,4,5,5-tetramethyl-1,3,2-dioxaborolan-2-yl)pyridin-2-yl) cyclopropanecarboxamide as a white solid (5.4 g, 57%). $^1$H NMR (400 MHz, CDCl$_3$): δ 1.34 (s, 12H), 1.77 (m, 1H), 2.25 (m, 1H), 2.46 (m, 1H), 7.42 (d, J=4.8 Hz, 1H), 8.31 (d, J=4.8 Hz, 1H), 8.54 (s, 1H), 8.99 (s, 1H).

2-methyl-N-(4-(4,4,5,5-tetramethyl-1,3,2-dioxaborolan-2-yl)pyridin-2-yl)pyrimidin-4-amine

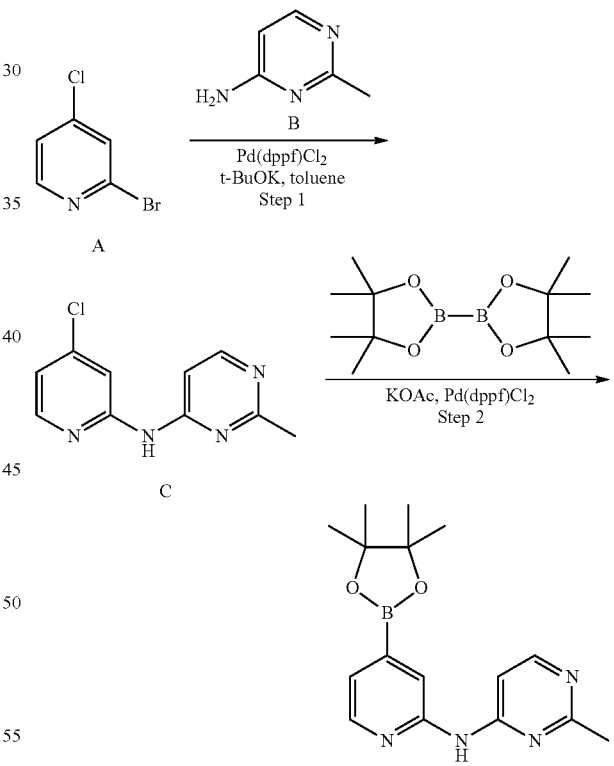

Step 1:
N-(4-chloropyridin-2-yl)-2-methylpyrimidin-4-amine t-BuOK (1.00 M in THF, 84 mL, 84 mmol) was added to a stirring mixture of 2-bromo-4-chloropyridine (14.0 g, 72.7 mmol), 2-methylpyrimidin-4-amine (6.1 g, 55.9 mmol), Pd(dppf)Cl$_2$ (0.82 g, 1.12 mmol), and dppf (2.48 g, 4.47 mmol) in toluene (204 mL). The reaction mixture was allowed to stir at 110° C. for 16 h under a nitrogen atmosphere, then was allowed to cool to rt and concentrated. The crude compound was purified by column chromatography to provide N-(4-chloropyridin-2-yl)-2-methylpyrimidin-4-amine (10 g, 81%). LCMS (FA): m/z=221.0 (M+H).

Step 2: 2-methyl-N-(4-(4,4,5,5-tetramethyl-1,3,2-dioxaborolan-2-yl)pyridin-2-yl)pyrimidin-4-amine A solution of N-(4-chloropyridin-2-yl)-2-methylpyrimidin-4-amine (50.0 g, 226.6 mmol), 4,4,4',4',5,5,5',5'-octamethyl-2,2'-bi-1,3,2-dioxaborolane (63.3 g, 249 mmol), and KOAc (66.7 g, 680 mmol) in anhydrous dioxane (1340 mL) was evacuated/purged with nitrogen three times. Pd(dppf)Cl$_2$ (24.9 g, 34.0 mmol) was added, and the resulting mixture was allowed to stir under an atmosphere of nitrogen at 110° C. for 16 h. The reaction mixture was allowed to cool to rt then filtered through celite. The filtrate was concentrated, and the resulting residue was washed with MTBE (300 mL) and filtered. The solid residue was added to a mixture of MTBE (2500 mL) and EtOAc (500 mL), stirred for 1 h, then filtered through celite. The filtrate was concentrated to give a residue which was washed with MTBE (300 mL) and then azeotropically coevaporated from EtOAc (1000 mL) twice to afford 2-methyl-N-(4-(4,4,5,5-tetramethyl-1,3,2-dioxaborolan-2-yl)pyridin-2-yl)pyrimidin-4-amine (49.5 g, 35% yield) as a grey solid. $^1$H NMR (400 MHz, DMSO-d): δ 10.47 (br s, 1H), 8.34 (br t, J=6.34 Hz, 2H), 7.80 (m, 2H), 7.15 (br d, J=4.52 Hz, 1H), 2.49 (s, 3H), 1.33 (s, 12H).

The intermediates listed in the table below (Table A) were prepared in an analogous fashion to Step 1 described immediately above from the appropriate starting materials:

| Intermediate | Reagent | Starting Material Chemical Structure | LCMS Data |
|---|---|---|---|
| 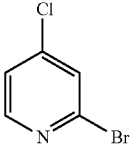 | A | 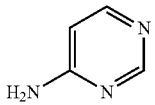 | LCMS (FA): m/z = 207.1 (M + H) |
| | B | 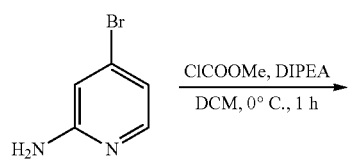 | |

Methyl [4-trimethylstannyl)pyridin-2-yl]carbamate

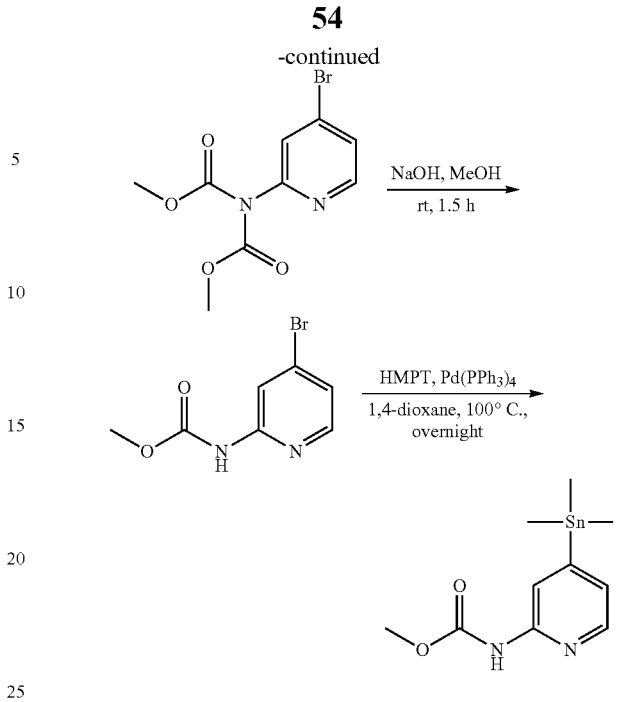

Step 1: dimethyl (4-bromopyridin-2-yl)imidodicarbonate

To a solution of 2-amino-4-bromopyridine (14.0 g, 81.0 mmol) in DCM (800 mL) was added DIEA (35.0 mL, 202 mmol) and methyl chloroformate (15.0 g, 162 mmol) at 0° C. The reaction mixture was stirred at 0° C. for 1 h. Saturated aqueous NH$_4$Cl was added and the aqueous layer was extracted with DCM. The combined organic layers were washed with brine, and concentrated by rotary evaporation to give a brown solid which was taken on without further purification.

Step 2: methyl (4-bromopyridin-2-yl)carbamate

To a solution of (4-bromopyridin-2-yl)imidodicarbonate (8.0 g, 27.7 mmol) in MeOH (150 mL) was added NaOH (2.21 g, 55.4 mmol). The reaction mixture was stirred at room temperature for 15 h. The reaction mixture was concentrated and then EtOAc and water were added. The aqueous layer was extracted with EtOAc. The combined organic layers were washed with brine, dried with Na$_2$SO$_4$ and concentrated by rotary evaporation to give methyl (4-bromopyridin-2-yl)carbamate (5.15 g, 81%) which was used without purification.

Step 3: methyl [4-(trimethylstannyl)pyridin-2-yl]carbamate

Under an atmosphere of nitrogen, a solution of methyl (4-bromopyridin-2-yl)carbamate (22 g, 95.2 mmol), HMPT (37.5 g, 115 mmol), Pd(PPh$_3$)$_4$ (3.3 g, 2.86 mmol) and NH$_4$Cl (225 mg, 4.77 mmol) in 1,4-dioxane (500 mL) was heated at 100° C. for 10 h. The mixture was filtered and concentrated. The crude compound was purified by column chromatography to give methyl [4-(trimethylstannyl)pyridin-2-yl]carbamate (13.5 g, 40%). $^1$H NMR (400 MHz, CDCl$_3$): δ 0.34 (s, 9H) 3.09 (s, 3H), 7.10 (d, J=4.6 Hz, 2H), 7.66 (br s, 1H), 8.116 (s, 1H), 8.16 (d, J=4.6 Hz, 2H).

Example 2: Synthesis of Intermediate 4-bromo-1H-pyrrolo[2,3-c]pyridines 4-bromo-7-ethyl-1H-pyrrolo[2,3-c]pyridine

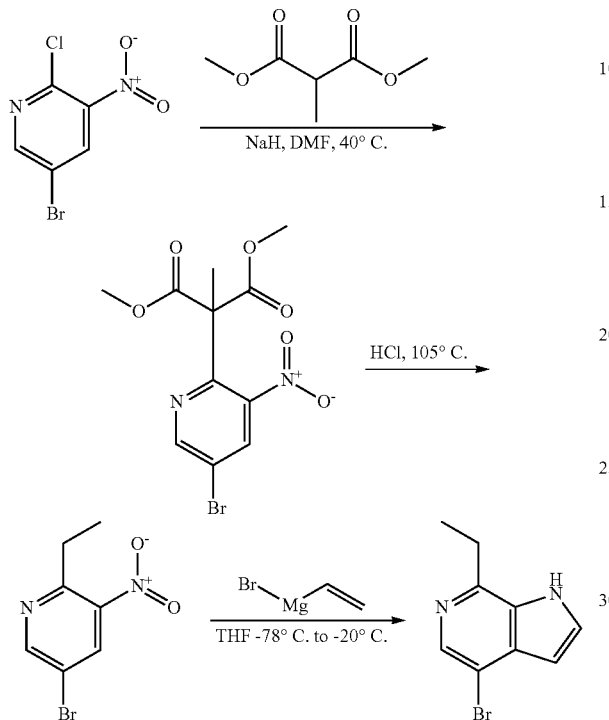

Step 1: dimethyl (5-bromo-3-nitropyridin-2-yl)methyl)malonate

To a suspension of NaH (60%0 in mineral oil, 0.54 g, 8.40 mmol) in DMF (12.0 mL) was slowly added dimethyl malonate (1.96 mL, 14.7 mmol). The mixture was stirred for 10 minutes at room temperature, then a solution of 5-bromo-2-chloro-3-nitropyridine (2.0 g, 8.40 mmol) in DMF (4.0 mL) was added. The mixture was stirred at room temperature for 30 minutes, then the heat was increased to 40° C. for 1 hour. The reaction was quenched by adding 0.5 M NaHCO$_3$ (120 mL). Extracted with Et$_2$O (2×75 mL). The combined organic layers were washed with brine, dried with Na$_2$SO$_4$ and concentrated to yield dimethyl (5-bromo-3-nitropyridin-2-yl)(methyl)malonate (3.21 g, 110%) which was used in the next step without purification.

Step 2: 5-bromo-2-ethyl-3-nitropyridine

Dimethyl (5-bromo-3-nitropyridin-2-yl)(methyl)malonate (3.00 g, 8.60 mmol) was dissolved in water (12 mL) and 12.0 M HCl (17 mL). The mixture was heated at 105° C. for 5 hours, then conc. HCl (17 mL) was added and the reaction mixture was heated to reflux for 2 hours. The mixture was diluted with 100 mL brine and extracted with Et$_2$O. The combined organic layers were washed with brine (2×50 mL), dried with Na$_2$OS$_4$ and concentrated. The crude compound was purified by column chromatography to yield 5-bromo-2-ethyl-3-nitropyridine (1.04 g, 52%). LCMS (FA): m/z=233.1 (M+H).

Step 3: 4-bromo-7-ethyl-1H-pyrrolo[2,3-c]pyridine

The procedure in step 1 of Example 3 was followed to yield 4-bromo-7-ethyl-1H-pyrrolo[2,3-c]pyridine (256 mg, 26%). LCMS (FA): m/z=227.3 (M+H).

4-bromo-N,N-dimethyl-1H-pyrrolo[2,3-c]pyridin-7-amine

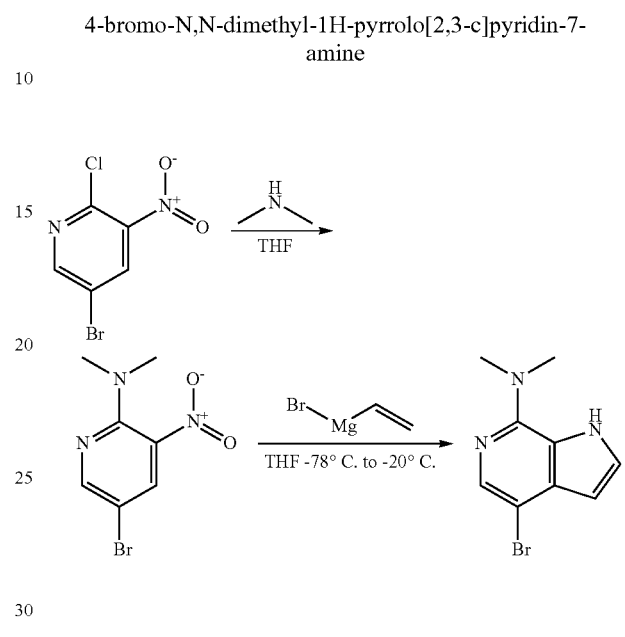

Step 1: 5-Bromo-N,N-dimethyl-3-nitropyridin-2-amine

To 5-bromo-2-chloro-3-nitropyridine (1.84 g, 7.75 mmol) was added dimethylamine (2.0 M in THF, 4.26 mL, 8.52 mmol). The reaction mixture was stirred at room temperature. Upon completion, Et$_2$O was added and a solid crashed out. Filtered to obtain 5-bromo-N,N-dimethyl-3-nitropyridin-2-amine (700 mg, 36%) and used in the next step without purification.

Step 2: 4-bromo-N,N-dimethyl-1H-pyrrolo[2,3-c]pyridin-7-amine

The procedure in step 1 of Example 3 was followed to yield 4-bromo-N,N-dimethyl-1H-pyrrolo[2,3-c]pyridin-7-amine (67 mg, 10%). LCMS (FA): m/z=242.1 (M+H).

Example 3: N-{4-[7-methyl-1-(phenylsulfonyl)-1H-pyrrolo[2,3-c]pyridin-4-yl]pyridin-2-yl}acetamide (I-4)

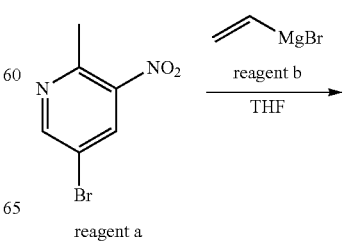

57
-continued

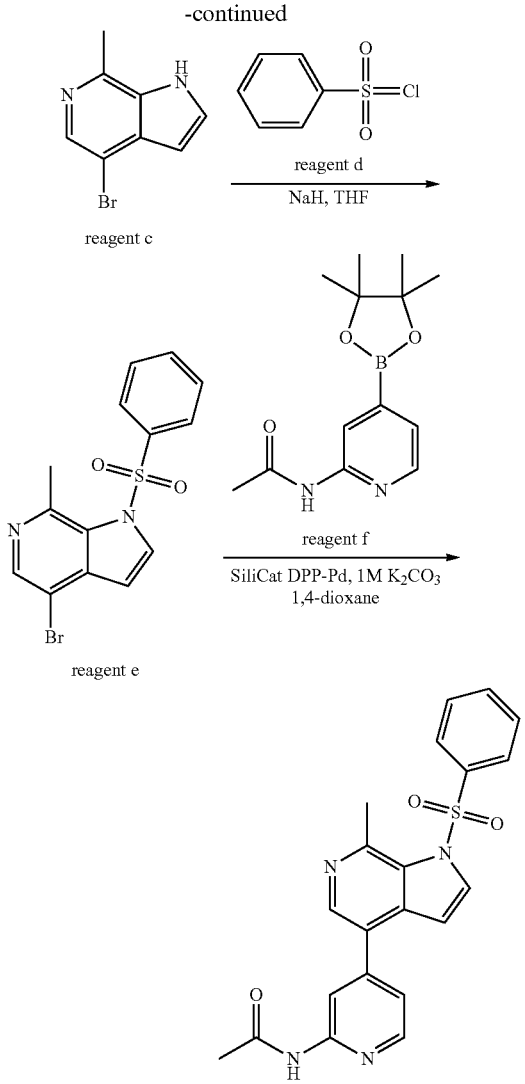

Step 1: 4-bromo-7-methyl-1H-pyrrolo[2,3-c]pyridine

5-Bromo-2-methyl-3-nitropyridine (2.00 g, 9.22 mmol) was dissolved in THF (92 mL) and the solution was cooled to −50° C. under an atmosphere of argon. Vinylmagnesium bromide (1 M in THF, 27.6 mL, 27.6 mmol) was added in one portion and the reaction mixture turned orange. The reaction was allowed to stir at −40° C. for 30 min and then quenched the reaction with saturated ammonium chloride solution. The mixture was extracted with EtOAc, the combined organic layers dried with MgSO$_4$ and concentrated by rotary evaporation. The crude material was purified by column chromatography to yield 4-bromo-7-methyl-1H-pyrrolo[2,3-c]pyridine (0.711 g, 36.6%). LCMS (FA): m/z=211.0, 213.0 (M+H).

Step 2: 4-bromo-7-methyl-1-(phenylsulfonyl)-1H-pyrrolo[2,3-c]pyridine

In a 1-neck round-bottom flask sodium hydride (60% in mineral oil, 171 mg, 4.26 mmol) was suspended in THF (21 mL) and cooled to 0° C. 4-bromo-7-methyl-1H-pyrrolo[2, 3-c]pyridine was added and the mixture was stirred for 30 min at 0° C. Benzenesulfonyl chloride (408 uL, 3.20 mmol) was added and the reaction was warmed to rt and stirred overnight. The reaction was quenched with ethyl acetate and water. The aqueous layer was extracted with ethyl acetate and the combined organic layers were washed with brine, dried over sodium sulfate and filtered. The solvent was removed by rotary evaporation and the crude material was purified by column chromatography to yield 4-bromo-7-methyl-1-(phenylsulfonyl)-1H-pyrrolo[2,3-c]pyridine (303 mg, 40.5%). $^1$H NMR (400 MHz, CDCl$_3$): δ 2.65 (s, 3H), 6.94 (d, J=3.8 Hz, 1H), 7.67 (m, 2H), 7.78 (m, 1H), 7.86 (m, 3H), 8.27 (d, J=3.8 Hz, 1H), 8.39 (s, 1H).

Step 3: N-{4-[7-methyl-1-(phenylsulfonyl)-1H-pyrrolo[2,3-c]pyridin-4-yl]pyridin-2-yl}acetamide A microwave vial was charged with N-[4-(4,4,5,5-tetramethyl-1,3,2-dioxaborolan-2-yl)pyridin-2-yl]acetamide (140 mg, 0.550 mmol) and SiliaCat DPP-Pd (68 mg, 0.017 mmol). The reaction mixture was purged with nitrogen and a solution of 4-bromo-7-methyl-1-(phenylsulfonyl)-1H-pyrrolo[2,3-c]pyridine (102 mg, 0.290 mmol) in 1,4-dioxane (2 mL) was added follow by 1.00 M potassium carbonate in water (0.293 mL, 0.293 mmol). The reaction mixture was heated at 180° C. in the microwave for 60 min. The mixture was filtered through a bed of celite and which was further washed with ethyl acetate. The filtrate was concentrated by rotary evaporation and purified by prep HPLC to yield N-{4-[7-methyl-1-phenylsulfonyl)-1H-pyrrolo[2,3-c]pyridin-4-yl]pyridin-2-yl}acetamide (63 mg, 53.0%). LCMS (FA): m/z=407.1 (M+H).

The compounds listed in the table below (Table 3) were prepared in an analogous fashion to that described above for Example 3, where the indicated starting materials were replaced as set forth in the table:

| Example | Starting material (step 3) Reagent | Starting material (step 3) Chemical Structure | Compound No. | LCMS Data |
|---|---|---|---|---|
| 3A | e | (structure) | I-45 | LCMS (FA): m/z = 345.0 (M + H) |
| 3B | e | (structure) | I-44 | LCMS (FA): m/z = 371.2 (M + H) |

-continued

| Example | Reagent | Starting material (step 3) Chemical Structure | Compound No. | LCMS Data |
|---|---|---|---|---|
| 3C | e | 2,4-difluorophenylsulfonyl-7-methyl-4-bromo-pyrrolo[2,3-c]pyridine | I-11 | LCMS (FA): m/z = 443.0 (M + H) |
| 3D | e | phenylsulfonyl-4-bromo-pyrrolo[2,3-c]pyridine | I-39 | LCMS (FA): m/z = 393.0 (M + H) |
| 3F | e | N,N-dimethylsulfamoyl-7-methyl-4-bromo-pyrrolo[2,3-c]pyridine | I-7 | LCMS (FA): m/z = 37.0 (M + H) |
| 3G*** | e | cyclopropylmethyl-7-methyl-4-bromo-pyrrolo[2,3-c]pyridine | I-36 | LCMS (FA): m/z = 321.1 (M + H) |
| 3H‡ | e | methylsulfonyl-4-bromo-pyrrolo[2,3-c]pyridine | I-21 | LCMS (AA): m/z = 331.2 (M + H) |

| Example | Reagent | Starting material (step 3) Chemical Structure | Compound No. | LCMS Data |
|---|---|---|---|---|
| 3J | e | methylsulfonyl-4-bromo-pyrrolo[2,3-c]pyridine | I-9 | LCMS (FA): m/z = 356.2 (M + H) |
| | f | pinacol boronate pyridinyl oxazolylamine | | |
| 3K | e | pyrrolidinylsulfonyl-7-methyl-4-bromo-pyrrolo[2,3-c]pyridine | I-23 | LCMS (FA): m/z = 400.3 (M + H) |
| 3L** | e | cyclopropylsulfonyl-4-bromo-pyrrolo[2,3-c]pyridine | I-37 | LCMS (AA): m/z = 357.3 (M + H) |
| 3M | e | ethylsulfonyl-7-methyl-4-bromo-pyrrolo[2,3-c]pyridine | I-16 | LCMS (FA): m/z = 359.3 (M + H) |

-continued

| Example | Reagent | Starting material (step 3) Chemical Structure | Compound No. | LCMS Data |
|---|---|---|---|---|
| 3N | e | 7-ethyl-4-bromo-1-(methylsulfonyl)-1H-pyrrolo[2,3-c]pyridine | I-3 | LCMS (FA): m/z = 359.3 (M + H) |
| 3O | e | 7-methyl-4-bromo-1-(o-tolylsulfonyl)-1H-pyrrolo[2,3-c]pyridine | I-34 | LCMS (FA): m/z = 421.3 (M + H) |
| 3P | e | 7-(dimethylamino)-4-bromo-1-(cyclopropylsulfonyl)-1H-pyrrolo[2,3-c]pyridine | I-18 | LCMS (FA): m/z = 400.3 (M + H) |
| 3T* | e | 3,7-dimethyl-4-bromo-1-(methylsulfonyl)-1H-pyrrolo[2,3-c]pyridine | I-5 | LCMS (FA): m/z = 359.2 (M + H) |
| 3U‡ | e | 4-bromo-1-(methylsulfonyl)-1H-pyrrolo[2,3-c]pyridine | I-32 | LCMS (AA): m/z = 289.2 (M + H) |
| | f | 2-amino-4-(4,4,5,5-tetramethyl-1,3,2-dioxaborolan-2-yl)pyridine | | |

-continued

| Example | Reagent | Starting material (step 3) Chemical Structure | Compound No. | LCMS Data |
|---|---|---|---|---|
| 3V | e | 4-bromo-N,N-dimethyl-1H-pyrrolo[2,3-c]pyridine-1-sulfonamide | I-33 | LCMS (FA): m/z = 360.5 (M + H) |
| 3W | e | 7-methyl-4-bromo-1-(methylsulfonyl)-1H-pyrrolo[2,3-c]pyridine | I-38 | LCMS (FA): m/z = 361.2 (M + H) |
| | f | methyl (4-(4,4,5,5-tetramethyl-1,3,2-dioxaborolan-2-yl)pyridin-2-yl)carbamate | | |
| 3X | e | 7-methyl-4-bromo-1-(isobutylsulfonyl)-1H-pyrrolo[2,3-c]pyridine | I-15 | LCMS (FA): m/z = 403.5 (M + H) |
| | f | methyl (4-(4,4,5,5-tetramethyl-1,3,2-dioxaborolan-2-yl)pyridin-2-yl)carbamate | | |

-continued

| Example | Reagent | Chemical Structure | Compound No. | LCMS Data |
|---|---|---|---|---|
| 3Y**,† | e | | I-46 | LCMS (SA): m/z = 363.3 (M + H) |
| 3Z† | e | | I-14 | LCMS (FA): m/z = 389.4 (M + H) |

*0.5M propenylmagnesium bromide in THF was used in step 1.
**Pd(dppf)Cl₂ was used in step 3.
***Cyclopropylmethyl bromide was used in step 2.
†KOtBu was used in step 1 in place of NaH.
‡PdCl₂(amphos), K₃PO₄ and DME used in step 3.

Example 3AA

4-bromo-3-fluoro-7-methyl-1H-pyrrolo[2,3-c]pyridine intermediate

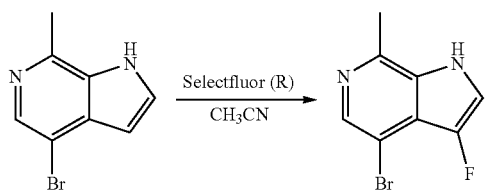

To a solution of 4-bromo-7-methyl-1H-pyrrolo[2,3-c]pyridine (1.1 g, 5.2 mmol) in acetonitrile (10.0 mL, 191 mmol) was added saturated sodium bicarbonate (9.3 mL, 240 mmol) and the reaction mixture cooled to 0° C. Then 1-chloromethyl-4-fluoro-1,4-diazoniabicyclo[2.2.2]octane bis(tetrafluoroborate) (Selectfluor®) (3.44 g, 9.71 mmol) was added and the reaction mixture was stirred at room temperature for 5 h. The reaction mixture was partitioned between ethyl acetate and water. The combined organic layers were washed with brine, dried over magnesium sulfate, filtered and concentrated by rotary evaporation. The residue was purified by column chromatography to provide 4-bromo-3-fluoro-7-methyl-1H-pyrrolo[2,3-c]pyridine (300 mg, 25%). LCMS (FA): m/z=231.1 (M+H).

Example 4: Methyl {4-[1-(cyclopropylsulfonyl)-7-methyl-1H-pyrrolo[2,3-c]pyridin-4-yl]pyridin-2-yl}carbamate (I-43)

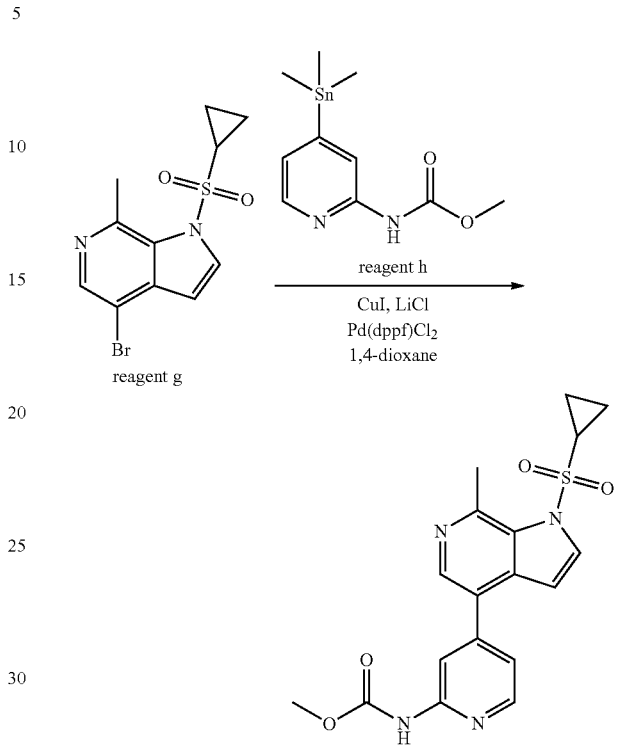

To a microwave vial was added 4-bromo-1-(cyclopropylsulfonyl)-7-methyl-1H-pyrrolo[2,3-c]pyridine (0.12 g, 0.38 mmol), methyl [4-(trimethylstannyl)pyridin-2-yl]carbamate (0.180 g, 0.57 mmol), lithium chloride (56.8 mg, 1.34 mmol), CuI (36.3 mg, 0.19 mmol) and 1,4-dioxane (4.21 mL, 54.0 mmol). The reaction mixture was flushed with argon and heated in the microwave at 110° C. for 30 min and then filtered through a short plug of celite. The celite was washed with methanol followed by EtOAc and the supernatant was concentrated by rotary evaporation. MeOH was added to the residue and the resulting precipitate was collected in a buchner funnel. The material was purified by prep HPLC to yield methyl {4-[1-(cyclopropylsulfonyl)-7-methyl-1H-pyrrolo[2,3-c]pyridin-4-yl]pyridin-2-yl}carbamate (24 mg, 16.0%). LCMS (FA): m/z=387.4 (M+H).

The compounds listed in the table below (Table 4) were prepared in an analogous fashion to that described above for Example 4, where the indicated starting materials were replaced as set forth in the table:

| Example | Reagent | Chemical Structure | Compound No. | LCMS Data |
|---|---|---|---|---|
| 4A | g | | I-29 | LCMS (FA): m/z = 347.2 (M + H) |

-continued

| Example | Starting material Reagent | Starting material Chemical Structure | Compound No. | LCMS Data |
|---|---|---|---|---|
| 4B | g | 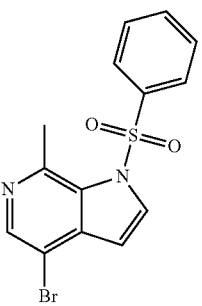 | I-2 | LCMS (FA): m/z = 423.8 (M + H) |
| 4C | g | 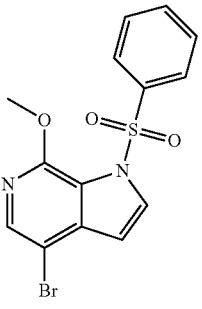 | I-10 | LCMS (FA): m/z = 439.4 (M + H) |
| 4D | g | 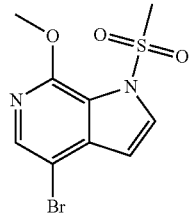 | I-1 | LCMS (FA): m/z = 377.4 (M + H) |
| 4E | g | 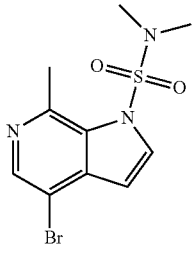 | I-6 | LCMS (FA): m/z = 390.5 (M + H) |
| 4F | g | 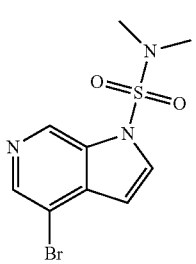 | I-17 | LCMS (FA): m/z = 376.5 (M + H) |

-continued

| Example | Starting material Reagent | Starting material Chemical Structure | Compound No. | LCMS Data |
|---|---|---|---|---|
| 4G | g | 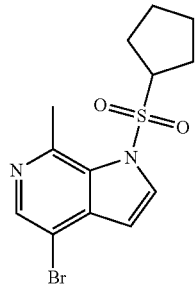 | I-12 | LCMS (FA): m/z = 415.4 (M + H) |
| 4H | g | 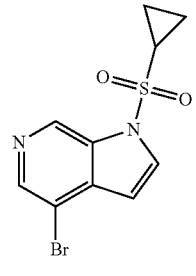 | I-30 | LCMS (FA): m/z = 373.4 (M + H) |

Example 5: N-{4-[1-(cyclopropylsulfonyl)-1H-pyrazolo[4,3-b]pyridin-6-yl]pyridin-2-yl}acetamide and N-{4-[2-(cyclopropylsulfonyl)-2H-pyrazolo[4,3-b]pyridin-6-yl]pyridin-2-yl}acetamide (I-22)

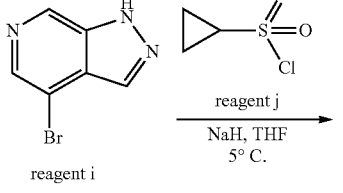

reagent i

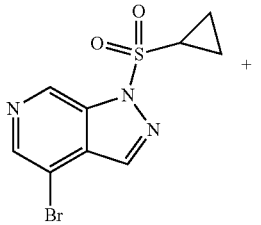

reagent k'

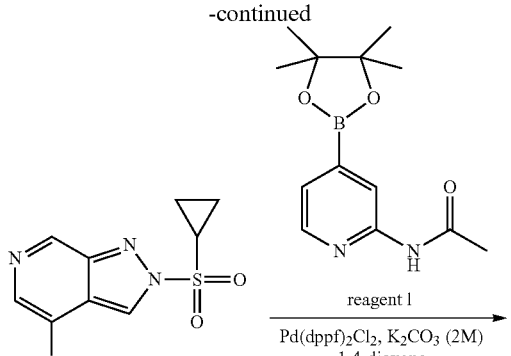

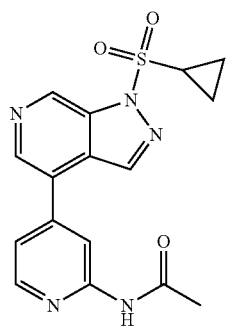

Step 1: 4-bromo-1-(cyclopropylsulfonyl)-1H-pyrazolo[3,4-c]pyridine

To a solution of 4-bromo-1H-pyrazolo[3,4-c]pyridine (215 mg, 1.08 mmol) in THF (6.08 mL) at 5° C. was added NaH (60:40 sodium hydride:mineral oil, 54.9 mg, 1.37 mmol). The mixture was stirred for 5 minutes at rt and then cooled again in ice bath to 5° C. Cyclopropanesulfonylchloride (141.0 uL, 1.36 mmol) was added dropwise and the mixture was allowed to stir for 15 min. The reaction mixture was quenched with ammonium chloride (2 M aq. solution, 5 mL) and was partitioned between ethyl acetate and water. The aqueous layer was further extracted with ethyl acetate and the combined organic layers were washed with brine, dried over sodium sulfate, filtered and concentrated by rotary evaporation. The residue was purified by column chromatography to provide 4-bromo-2-(cyclopropylsulfonyl)-2H-pyrazolo[3,4-c]pyridine (36 mg, 11%) LCMS (AA): m/z=358.4 (M+H) and 4-bromo-1-(cyclopropylsulfonyl)-1H-pyrazolo[3,4-c]pyridine (237 mg, 72%). LCMS (AA): m/z=358.4 (M+H).

Step 2: N-{4-[1-(cyclopropylsulfonyl)-1H-pyrazolo[3,4-c]pyridin-4-yl]pyridin-2-yl}acetamide A microwave vial was charged with N-[4-(4,4,5,5-tetramethyl-1,3,2-dioxaborolan-2-yl)pyridin-2-yl]acetamide (202 mg, 0.77 mmol), [1,1'-bis(diphenylphosphino)ferrocene]dichloropalladium(II), complex with dichloromethane (1:1) (32 mg, 0.04 mmol) and purged with nitrogen, 4-bromo-1-(cyclopropylsulfonyl)-1H-pyrazolo[3,4-c]pyridine (188 mg, 0.62 mmol) in 1,4-dioxane (5.0 mL) was added followed by 2.00 M of potassium carbonate in water (0.62 mL, 1.24 mmol). The reaction mixture was heated in an oil bath at 90° C. for 15 min. The reaction mixture was partitioned between ethyl acetate and water. The aqueous layer was further extracted with ethyl acetate and the combined organic layers were washed with brine, dried over sodium sulfate, filtered and concentrated by rotary evaporation. The residue was purified by column chromatography. The resulting off white solid was triturated with MeOH, filtered, and dried under vacuum to yield N-{4-[1-(cyclopropylsulfonyl)-1H-pyrazolo[3,4-c]pyridin-4-yl]pyridin-2-yl}acetamide (191 mg, 86%) as a white solid. LCMS (AA): m/z=358.4 (M+H).

Example 6: N-{4-[2-methyl-1-(phenylsulfonyl)-1H-pyrrolo[2,3-c]pyridin-4-yl]pyridin-2-yl}acetamide and N-{4-[2-ethyl-1-(phenylsulfonyl)-1H-pyrrolo[2,3-c]pyridin-4-yl]pyridin-2-yl}acetamide (I-31 and I-24)

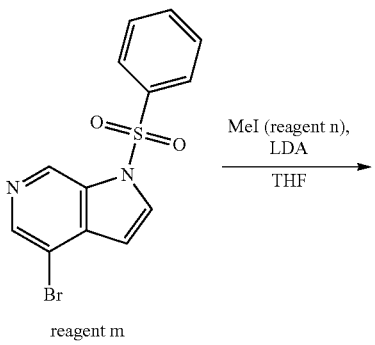

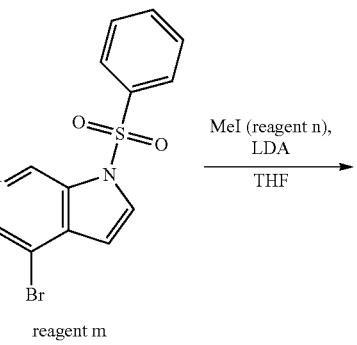

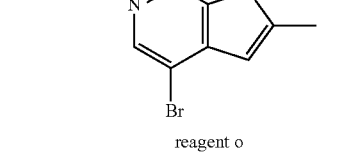

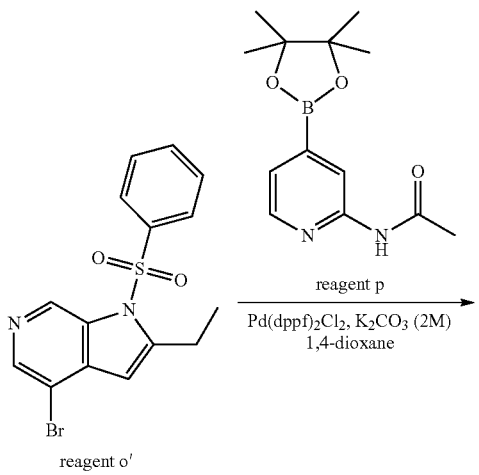

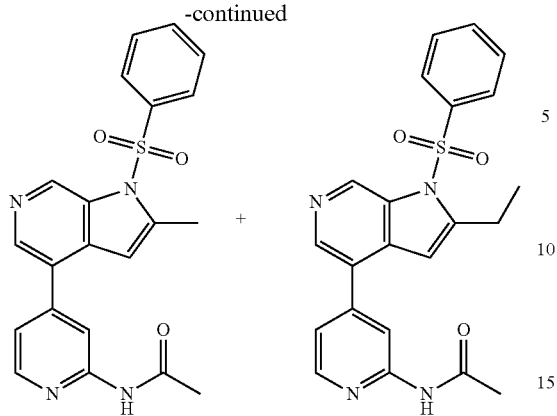

Step 1: 4-bromo-2-methyl-1-(phenylsulfonyl)-1H-pyrrolo[2,3-c]pyridine and 4-bromo-2-ethyl-1-(phenylsulfonyl)-1H-pyrrolo[2,3-c]pyridine To a solution of 4-bromo-1-(phenylsulfonyl)-1H-pyrrolo[2,3-c]pyridine (603 mg, 1.79 mmol) in THF (6.30 mL, 77.6 mmol) cooled to −38° C. (bath temperature) was added LDA (2.0 M in THF, 1.79 mL, 3.58 mmol) dropwise over ca. 20 min. The reaction was allowed to stir for 45 min followed by the dropwise addition of methyl iodide (0.667 mL, 10.7 mmol). After stirring for 10 min at −38° C. (bath temperature) the reaction was allowed to warm to rt and stirred for 20 min. The reaction was quenched with 1 M HCl (~3.5 ml) to adjust the pH to ~3.5-4 and then partitioned between water and ethyl acetate. The aqueous layer was further extracted with ethyl acetate and the combined organics were washed with brine, dried over sodium sulfate and concentrated by rotary evaporation. Purification by column chromatography provided a ~7:1 mixture of 4-bromo-2-methyl-1-phenylsulfonyl)-1H-pyrrolo[2,3-c]pyridine and 4-bromo-2-ethyl-1-(phenylsulfonyl)-1H-pyrrolo[2,3-c]pyridine (513 mg, 81.7%). LCMS: (AA): m/z=407.1 and 421.1 (M+H).

Step 2: N-{4-[2-methyl-1-(phenylsulfonyl)-1H-pyrrolo[2,3-c]pyridin-4-yl]pyridin-2-yl}acetamide and N-{4-[2-ethyl-1-(phenylsulfonyl)-1H-pyrrolo[2,3-c]pyridin-4-yl]pyridin-2-yl}acetamide Using the appropriate starting materials, followed the procedure in Step 2 of Example 5 with the following modification: Heated at 90° C. for 10 min and 100° C. for 5 min. Prep HPLC yielded both N-{4-[2-methyl-1-(phenylsulfonyl)-1H-pyrrolo[2,3-c]pyridin-4-yl]pyridin-2-yl}acetamide (125 mg, 70%) LC-MS: (AA) ES+ 407.1, RT=10.06 min; and N-{4-[2-ethyl-1-(phenylsulfonyl)-H-pyrrolo[2,3-c]pyridin-4-yl]pyridin-2-yl}acetamide (15 mg, 8.1%). LCMS (AA): m/z=421.1 (M+H), RT=8.77 min.

Example 7: Methyl {4-[1-(phenylsulfonyl)-1H-pyrrolo[2,3-c]pyridin-4-yl]pyridin-2-yl}carbamate (I-28)

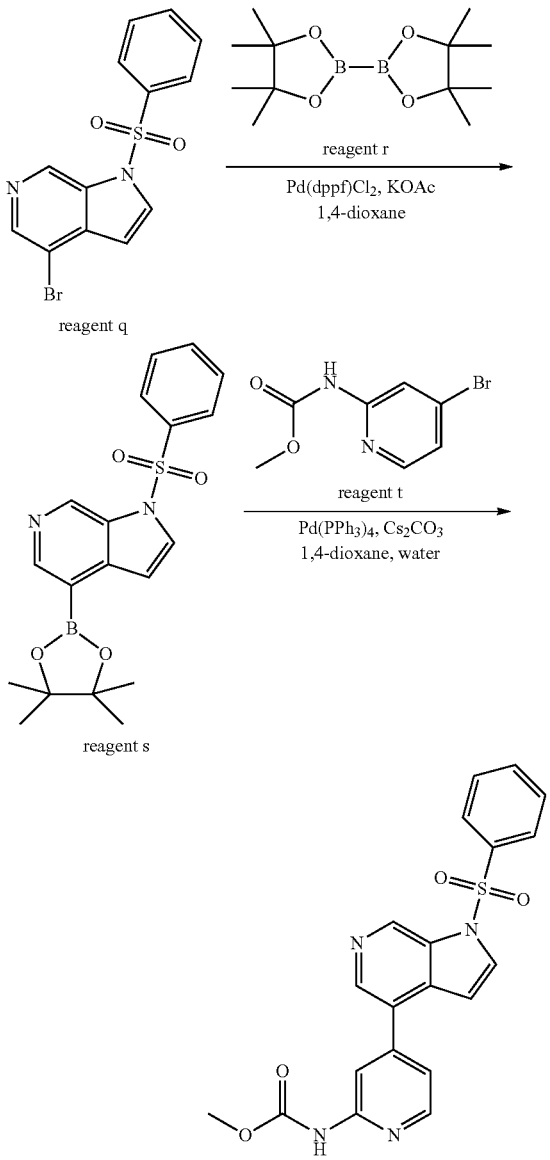

Step 1: 1-(Phenylsulfonyl)-4-(4,4,5,5-tetramethyl-1,3,2-dioxaborolan-2-yl)-1H-pyrrolo[2,3-c]pyridine A suspension of 4-bromo-1-(phenylsulfonyl)-1H-pyrrolo[2,3-c]pyridine (100 mg, 0.297 mmol), bis(pinacolato)diboron (98 mg, 0.39 mmol), potassium acetate (87 mg, 0.89 mmol) and [1,1'-bis(diphenylphosphino)ferrocene]palladium(II)dichloride (49 mg, 0.059 mmol) was stirred in 1,4-dioxane (0.58 mL) in a microwave vial and purged with argon. The reaction mixture was sealed and heated at 100° C. in an oil bath overnight. The mixture was then filtered through a plug of silica gel and washed with ethyl acetate. The filtrate was concentrated by rotary evaporation to yield 1-(phenylsulfonyl)-4-(4,4,5,5-tetramethyl-1,3,2-dioxaborolan-2-yl)-1H-pyrrolo[2,3-c]pyridine (114 mg, 100%) and used in the next step without purification.

Step 2: Methyl {4-[1-(phenylsulfonyl)-1H-pyrrolo[2,3-c]pyridin-4-yl]pyridin-2-yl}carbamate A mixture of methyl (4-bromopyridin-2-yl)carbamate (56 mg, 0.24 mmol), [1-(phenylsulfonyl)-1H-pyrrolo[2,3-c]pyridin-4-yl]boronic acid (117 mg, 0.39 mmol), tetrakis(triphenylphosphine)palladium(0) (28 mg, 0.024 mmol) and cesium carbonate (154 mg, 0.47 mmol) was stirred in 1,4-dioxane (1.9 mL) and water (0.3 mL) in a microwave vial and purged with nitrogen. The reaction mixture was heated in the microwave at 135° C. for 25 min., then concentrated under reduced pressure. The crude material was purified by prep HPLC to yield methyl (4-[1-(phenylsulfonyl)-1H-pyrrolo[2,3-c]pyridin-4-yl]pyridin-2-yl)carbamate (22 mg, 22.1%). LCMS (FA): m/z=409.4 (M+H).

Example 8: N-(1,3-oxazol-2-yl)-4-[1-(phenylsulfonyl)-1H-pyrrolo[2,3-c]pyridin-4-yl]pyridin-2-amine (I-13)

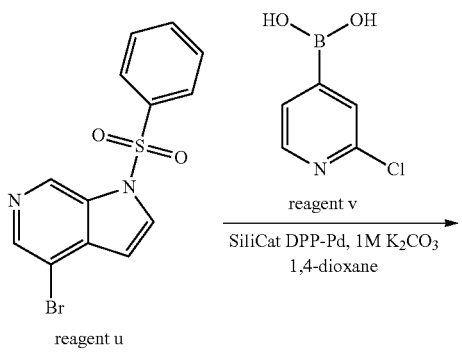

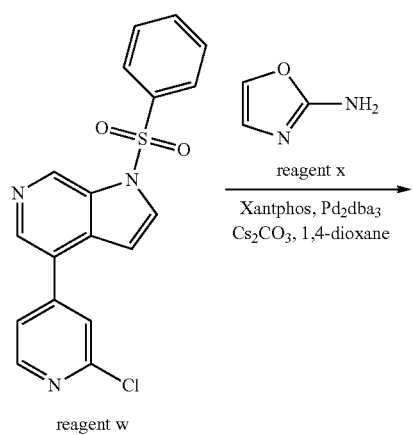

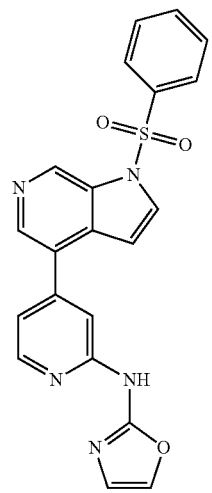

Step 1: 4-(2-Chloropyridin-4-yl)-1-(phenylsulfonyl)-1H-pyrrolo[2,3-c]pyridine

Using the appropriate starting materials, the procedure described in Step 3 of Example 3 was followed to yield 4-(2-chloropyridin-4-yl)-1-(phenylsulfonyl)-1H-pyrrolo[2,3-c]pyridine (46%). LCMS (FA): m/z=369.9 (M+H).

Step 2: N-(1,3-oxazol-2-yl)-4-[1-(phenylsulfonyl)-1H-pyrrolo[2,3-c]pyridin-4-yl]pyridin-2-amine A mixture of oxazole-2-amine (82 mg, 0.97 mmol), 4-(2-chloropyridin-4-yl)-1-(phenylsulfonyl)-1H-pyrrolo[2,3-c]pyridine (100 mg, 0.270 mmol) and cesium carbonate (220 mg, 0.676 mmol) in 1,4-dioxane (2.3 mL, 30.0 mmol) was purged with nitrogen followed by the addition of tris(dibenzylideneacetone)dipalladium(0) (24.8 mg, 0.027 mmol) and bis(diphenylphosphino)-9,9-dimethylxanthene (15.6 mg, 0.027 mmol). The reaction mixture was heated in the microwave at 130° C. for 90 min and then diluted with ethyl acetate. Insoluble material was removed by filtration and the filtrate was concentrated by rotary evaporation. The crude material was purified by column chromatography followed by further purification by prep HPLC to yield N-(1,3-oxazol-2-yl)-4-[1-(phenylsulfonyl)-1H-pyrrolo[2,3-c]pyridin-4-yl]pyridin-2-amine (15 mg, 13.3%). LCMS (FA): m/z=418.8 (M+H).

Example 9: 4-(2-chloro-5-fluoropyridin-4-yl)-1-(cyclopropylsulfonyl)-1H-pyrrolo[2,3-c]pyridine (I-8)

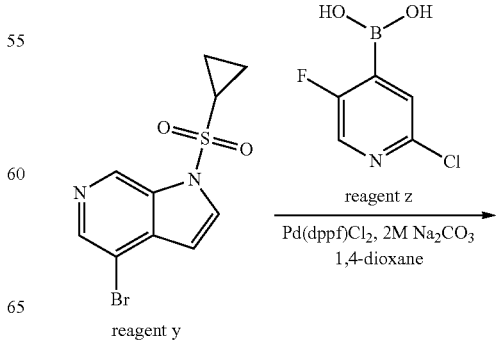

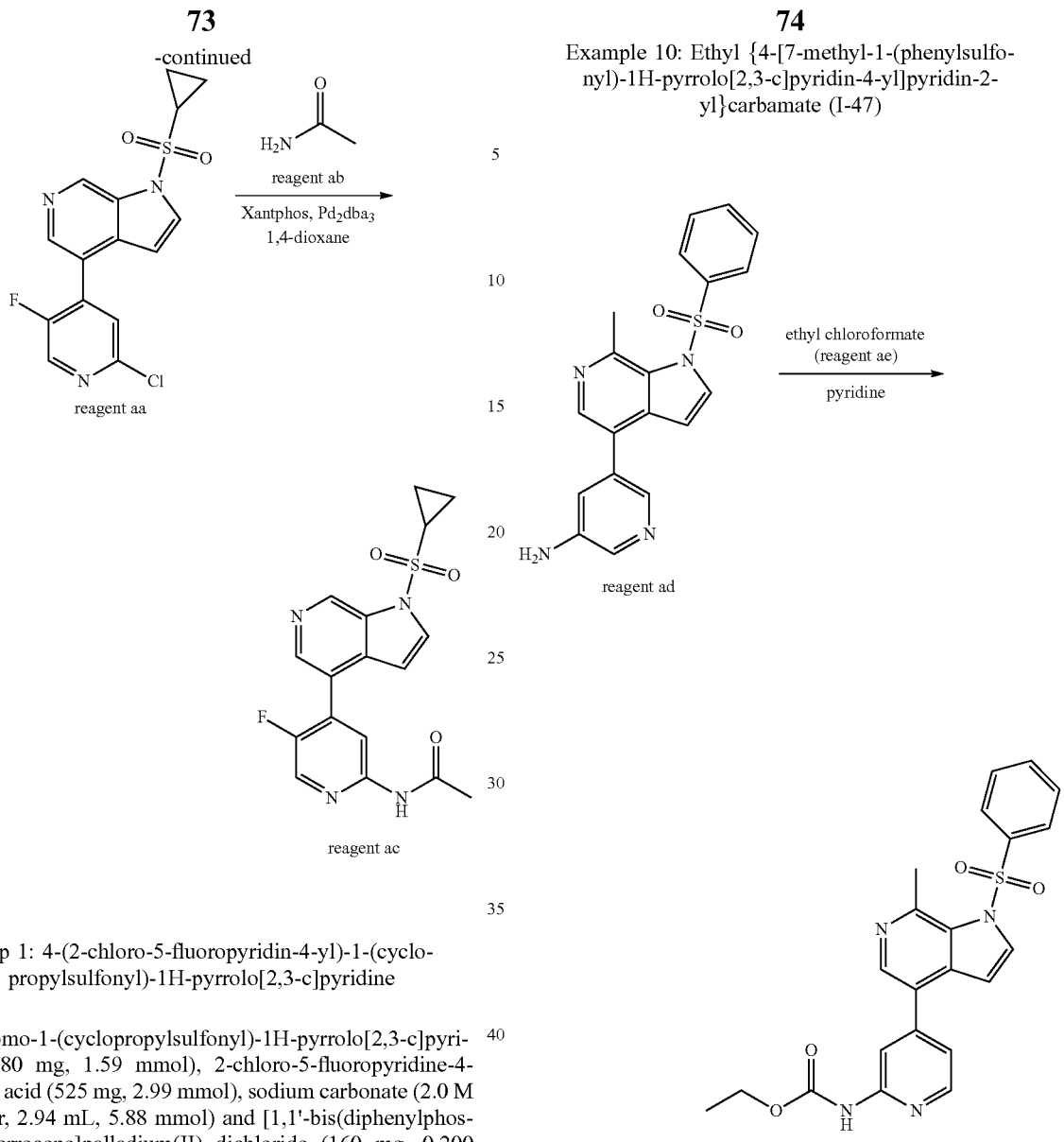

Example 10: Ethyl {4-[7-methyl-1-(phenylsulfonyl)-1H-pyrrolo[2,3-c]pyridin-4-yl]pyridin-2-yl}carbamate (I-47)

Step 1: 4-(2-chloro-5-fluoropyridin-4-yl)-1-(cyclopropylsulfonyl)-1H-pyrrolo[2,3-c]pyridine 4-bromo-1-(cyclopropylsulfonyl)-1H-pyrrolo[2,3-c]pyridine (480 mg, 1.59 mmol), 2-chloro-5-fluoropyridine-4-boronic acid (525 mg, 2.99 mmol), sodium carbonate (2.0 M in water, 2.94 mL, 5.88 mmol) and [1,1'-bis(diphenylphosphino)ferrocene]palladium(II) dichloride (160 mg, 0.200 mmol) were suspended in 1,2-dimethoxyethane (8.82 mL) and heated in the microwave at 110° C. for 25 min. Added an additional 0.5 equivalents of 2-chloro-5-fluoropyridine-4-boronic acid and [1,1'-bis(diphenylphosphino)ferrocene]palladium(II)dichloride and heated in the microwave at 110° C. for an additional 25 min. Water was added and the reaction mixture was extracted with ethyl acetate. The organic layer was dried over sodium sulfate and concentrated by rotary evaporation. The crude material was purified by column chromatography to yield 4-(2-chloro-5-fluoropyridin-4-yl)-1-(cyclopropylsulfonyl)-1H-pyrrolo[2,3-c]pyridine (188 mg, 33.7%). LCMS (FA): m/z=352.3 (M+H).

Step 2: N-{4-[1-(cyclopropylsulfonyl)-1H-pyrrolo[2,3-c]pyridin-4-yl]-5-fluoropyridin-2-yl}acetamide Using the appropriate starting materials, the procedure described in Step 3 of Example 3 was followed to yield N-{4-[1-(cyclopropylsulfonyl)-1H-pyrrolo[2,3-c]pyridin-4-yl]-5-fluoropyridin-2-yl}acetamide (49.6%). LCMS (FA): m/z=375.3 (M+H).

Step 1: Ethyl {4-[7-methyl-1-(phenylsulfonyl)-1H-pyrrolo[2,3-c]pyridin-4-yl]pyridin-2-yl}carbamate To a solution of 4-[7-methyl-1-(phenylsulfonyl)-1H-pyrrolo[2,3-c]pyridin-4-yl]pyridin-2-amine (35 mg, 0.096 mmol) in pyridine (0.43 mL, 5.3 mmol) at 5° C. was added ethyl chloroformate (11.5 uL, 0.120 mmol). The mixture was stirred for 1.5 h at 5° C. and then quenched with 0.20 mL of MeOH and stirred at room temperature. The mixture was partitioned between ethyl acetate and water. The organic layer was washed with brine, dried over sodium sulfate and concentrated by rotary evaporation. The crude material was purified by column chromatography to yield ethyl {4-[7-methyl-1-(phenylsulfonyl)-1H-pyrrolo[2,3-c]pyridin-4-yl]pyridin-2-yl}carbamate (35 mg, 83%). LCMS (AA): m/z=437.2 (M+H).

The compounds listed in the table below (Table 5) were prepared in an analogous fashion to that described above starting from the list class of starting materials:

| Example | Starting material Reagent | Chemical Structure | Compound No. | LCMS Data |
|---|---|---|---|---|
| 10A | ad | (structure) | I-42 | LCMS (AA): m/z = 401.5 (M + H) |
| 10B* | ad | (structure) | I-25 | LCMS (AA): m/z = 361.5 (M + H) |
| 10C** | ad, ae | (structure) | I-48 | LCMS (AA): m/z = 387.2 (M + H) |

*DIEA and DCM were used instead of pyridine.
**After workup of the reaction, the crude mixture was treated with 0.01M K$_2$CO$_3$ in MeOH for 10 min at rt to deprotect the methyl ester, providing the free alcohol.

Example 11: (rac)-2,2-difluoro-N-{4-[7-methyl-1-(methylsulfonyl)-1H-pyrrolo[2,3-c]pyridin-4-yl]pyridin-2-yl}cyclopropanecarboxamide (I-35)

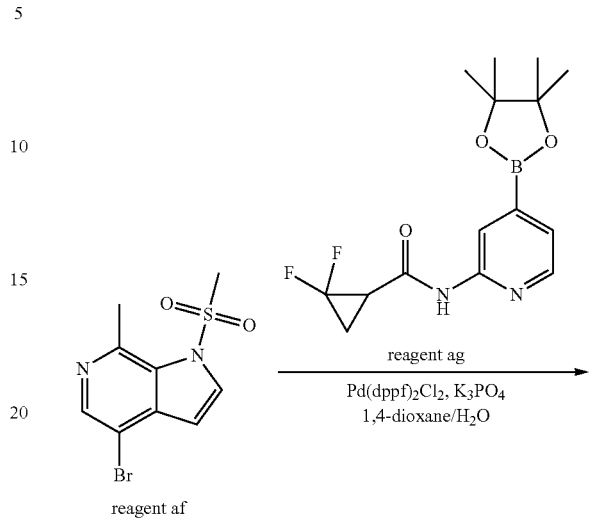

reagent af

Step 1: (rac)-2,2-difluoro-N-{4-[7-methyl-1-(methylsulfonyl)-1H-pyrrolo[2,3-c]pyridin-4-yl]pyridin-2-yl}cyclopropanecarboxamide A microwave vial was charged with (rac)-2,2-difluoro-N-(4-(4,4,5,5-tetramethyl-1,3,2-dioxaborolan-2-yl)pyridin-2-yl)cyclopropanecarboxamide (150 mg, 0.46 mmol), 4-bromo-7-methyl-1-(methylsulfonyl)-1H-pyrrolo[2,3-c]pyridine (100 mg, 0.35 mmol), [1,1'-bis(diphenylphosphino)ferrocene]dichloropalladium(II), complex with dichloromethane (1:1) (33 mg, 0.04 mmol) and potassium phosphate (194 g, 0.91 mmol), 1,4-dioxane (2.0 mL) and water (0.2 mL) were added and the mixture was purged with argon. The reaction mixture was heated in an oil bath at 90° C. for 2 h. The reaction mixture was partitioned between ethyl acetate and brine. The aqueous layer was further extracted with ethyl acetate and the combined organic layers were washed with brine, dried over sodium sulfate, filtered and concentrated by rotary evaporation. The residue was purified by column chromatography to yield (rac)-2,2-difluoro-N-{4-[7-methyl-1-(methylsulfonyl)-1H-pyrrolo[2,3-c]pyridin-4-yl]pyridin-2-yl}cyclopropanecarboxamide as a racemic mixture (92 mg, 65%) as a white solid. LCMS (FA): m/z=407.3 (M+H).

Example 12: N-{4-[1-(cyclopropylsulfonyl)-1H-pyrrolo[2,3-c]pyridin-4-yl]pyridin-2-yl}-2-(1H-tetrazol-5-yl)acetamide (I-27)

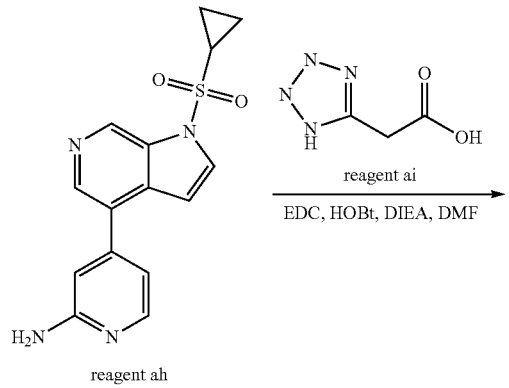

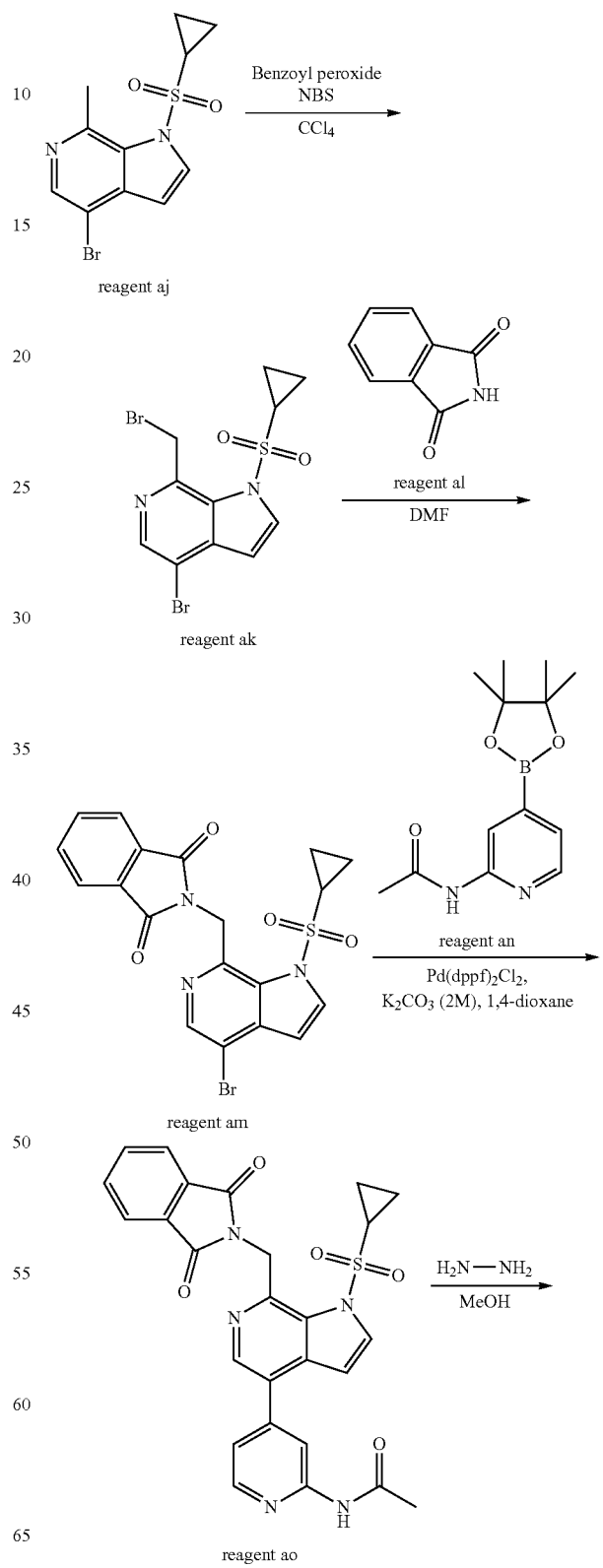

Example 13: N-{4-[7-(aminomethyl)-1-(cyclopropylsulfonyl)-1H-pyrrolo[2,3-c]pyridin-4-yl]pyridin-2-yl}acetamide.CH$_2$O$_2$ ([I-41].CH$_2$O$_2$)

A flask was charged with 4-[1-(cyclopropylsulfonyl)-1H-pyrrolo[2,3-c]pyridin-4-yl]pyridin-2-amine (95.0 mg, 0.302 mmol) and 1H-tetrazole-5-acetic acid (46 mg, 0.36 mmol) in acetonitrile (1.5 mL, 29 mmol). N,N-dimethylformamide (1.5 mL, 19 mmol), N-(3-dimethylaminopropyl)-N-ethylcarbodiimide hydrochloride (59 mg, 0.31 mmol) and 1-hydroxybenzotriazole (42 mg, 0.31 mmol) were added. The mixture was stirred at room temperature overnight, concentrated to remove CH$_3$CN. The mixture was added to 10 mL of water and the resulting dark slurry was acidified to pH 3 with 0.5 M aqueous citric acid. After stirring for 20 min the mixture was filtered and the collected solid was dried under vacuum. The crude product was purified by prep HPLC to yield N-{4-[1-(cyclopropylsulfonyl)-1H-pyrrolo[2,3-c]pyridin-4-yl]pyridin-2-yl}-2-(1H-tetrazol-5-yl)acetamide (21 mg, 16%) LCMS (AA): m/z=425.4 (M+H).

-continued

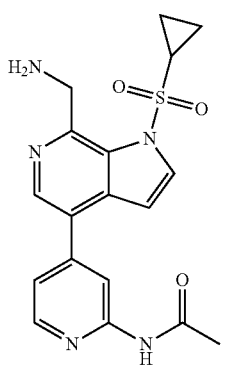

Step 1: 4-bromo-7-(bromomethyl)-1-(cyclopropylsulfonyl)-1H-pyrrolo[2,3-c]pyridine Into a 1-neck round-bottom flask, 4-bromo-1-(cyclopropylsulfonyl)-7-methyl-1H-pyrrolo[2,3-c]pyridine (250 mg, 0.793 mmol). N-bromosuccinimide (169 mg, 0.951 mmol) and benzoyl peroxide (19 mg, 0.080 mmol) were added into carbon tetrachloride (25 mL, 260 mmol). The mixture was refluxed overnight. To the mixture was added water and extracted with DCM. The organic layer was washed with water and dried with sodium sulfate. After removal of the salt, the solvent was removed to give the crude product. The crude product was purified by column chromatography to yield 4-bromo-7-(bromomethyl)-1-(cyclopropylsulfonyl)-1H-pyrrolo[2,3-c]pyridine (200 mg, 60%) LCMS (AA): m/z=395.0 (M+H).

Step 2: 2-{[4-bromo-1-(cyclopropylsulfonyl)-1H-pyrrolo[2,3-c]pyridin-7-yl]methyl}-1H-isoindole-1,3(2H)-dione Into a 1-neck round-bottom flask, 4-bromo-7-(bromomethyl)-1-(cyclopropylsulfonyl)-1H-pyrrolo[2,3-c]pyridine (190 mg, 0.48 mmol) and potassium phthalimide (120 mg, 0.63 mmol) was added into N,N-dimethylformamide (10 mL, 100 mmol). The mixture was stirred at room temperature overnight. Removed solvent by rotary evaporation, then dissolved the residue in EtOAc. The organic layer was washed with brine, and the solvent was removed to give the crude product 2-{[4-bromo-1-(cyclopropylsulfonyl)-1H-pyrrolo[2,3-c]pyridin-7-yl]methyl}-1H-isoindole-1,3(2H)-dione (110 mg, 50%) LCMS (AA): m/z=462.1 (M+H).

Step 3: N-(4-{1-(cyclopropylsulfonyl)-7-[(1,3-dioxo-1,3-dihydro-2H-isoindol-2-yl)methyl]-1H-pyrrolo[2,3-c]pyridin-4-yl}pyridin-2-yl)acetamide Followed the procedure described in Step 2 of Example 5 with the following modification: Heated at 130° C. for 30 min. under microwave irradiation to yield N-(4-{1-(cyclopropylsulfonyl)-7-[(1,3-dioxo-1,3-dihydro-2H-isoindol-2-yl)methyl]-1H-pyrrolo[2,3-c]pyridin-4-yl}pyridin-2-yl)acetamide (70 mg, 57%) LCMS (FA): m/z=516.4 (M+H).

Step 4: N-{4-[7-(aminomethyl)-1-(cyclopropylsulfonyl)-1H-pyrrolo[2,3-c]pyridin-4-yl]pyridin-2-yl}acetamide·CH₂O₂

Into a 1-neck round-bottom flask, N-(4-{1-(cyclopropylsulfonyl)-7-[(1,3-dioxo-1, 3-dihydro-2H-isoindol-2-yl) methyl]-1H-pyrrolo[2,3-c]pyridin-4-yl}pyridin-2-yl)acetamide (71 mg, 0.14 mmol) and hydrazine hydrate (70 uL, 1 mmol) was added into methanol (7.10 mL, 175 mmol). The mixture was stirred at room temperature for 4 h. Removed solvent by rotary evaporation, then dissolved the residue in EtOAc. The organic layer was washed with water, and the solvent was removed to give the crude product. The crude product was purified by prep HPLC to provide N-{4-[7-(aminomethyl)-1-(cyclopropylsulfonyl)-1H-pyrrolo[2,3-c]pyridin-4-yl]pyridin-2-yl}acetamide·CH2O2 (50 mg, 80%) LCMS (FA): m/z=386.3 (M+H).

Example 14: N-{4-[1-(cyclopropylsulfonyl)-1H-pyrrolo[2,3-c]pyridin-4-yl]pyridin-2-yl}pyrimidin-4-amine (I-49) and N-[4-(1H-pyrrolo[2,3-c]pyridin-4-yl)pyridin-2-yl]pyrimidin-4-amine (I-50)

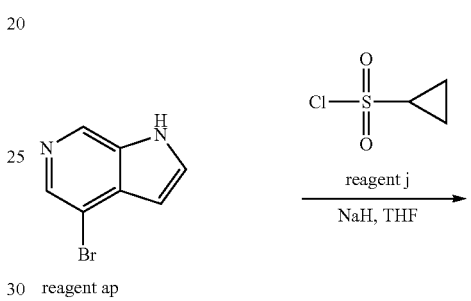

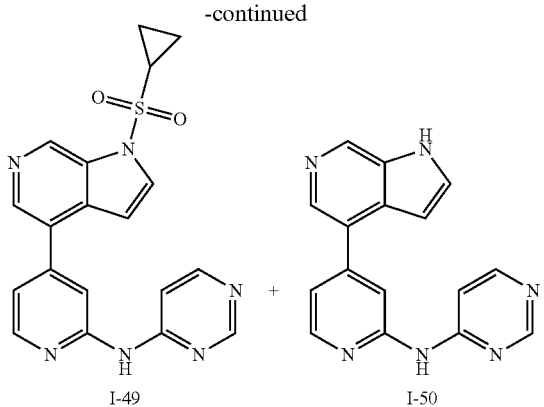

I-49 + I-50

Step 1: 4-bromo-1-(cyclopropylsulfonyl)-1H-pyrrolo[2,3-c]pyridine

To a stirring solution of 4-bromo-1H-pyrrolo[2,3-c]pyridine (26 g, 130 mmol) in THF (260 mL) was added NaH (60% in oil dispersion, 8 g, 200 mmol) portionwise at 0° C. The reaction was allowed to stir at 0° C. for 30 min, then a solution of cyclopropanesulfonyl chloride (28 g, 200 mmol) in THF (50 mL) was added dropwise. The resulting solution was allowed to stir at 0° C. for 4 h then the reaction mixture was diluted with saturated NH$_4$Cl solution (50 mL) and extracted with EtOAc. The combined organic solutions were dried over Na$_2$SO$_4$, filtered and concentrated to provide the crude product, which was recrystallized from EtOAc to provide 4-bromo-1-(cyclopropylsulfonyl)-1H-pyrrolo[2,3-c]pyridine as a white solid (26.0 g, 65.5%). LCMS (FA): m/z=301.0 (M+H).

Step 2: 1-(cyclopropylsulfonyl)-4-(4,4,5,5-tetramethyl-1,3,2-dioxaborolan-2-yl)-1H-pyrrolo[2,3-c]pyridine A mixture of 4-bromo-1-(cyclopropylsulfonyl)-1H-pyrrolo[2,3-c]pyridine (16 g, 53 mmol), 4,4,4',4',5,5,5',5'-octamethyl-2,2'-bi-1,3,2-dioxaborolane (14.8 g, 58 mmol), KOAc (15.8 g, 161 mmol) and Pd(dppf)Cl$_2$ (5.3 g, 7.2 mmol) in 1,4-dioxane (600 mL) was allowed to stir at reflux for 18 h under a nitrogen atmosphere. The reaction mixture was allowed to cool to rt and then filtered and concentrated. The residue was diluted with EtOAc (100 mL). Active carbon (70 g) was added and the mixture was allowed to stir at reflux for 2 h. The mixture was allowed to cool to 40° C. and then was filtered through celite. The filtrate was concentrated to give the crude product, which was recrystallized from EtOAc and pentane to give 1-(cyclopropylsulfonyl)-4-(4,4,5,5-tetramethyl-1,3,2-dioxaborolan-2-yl)-1H-pyrrolo[2,3-c]pyridine (5.1 g, 27.5%).

Step 3: N-{4-[1-(cyclopropylsulfonyl)-1H-pyrrolo[2,3-c]pyridin-4-yl]pyridin-2-yl}pyrimidin-4-amine and N-[4-(1H-pyrrolo[2,3-c]pyridin-4-yl)pyridin-2-yl]pyrimidin-4-amine To a mixture of 1-(cyclopropylsulfonyl)-4-(4,4,5,5-tetramethyl-1,3,2-dioxaborolan-2-yl)-1H-pyrrolo[2,3-c]pyridine (219.5 mg, 0.630 mmol), N-(4-chloropyridin-2-yl)pyrimidin-4-amine (104.2 mg, 0.504 mmol), degassed 1,4-dioxane (1.8 mL) and degassed K$_3$PO$_4$ solution (0.50 M in water, 2.02 mL, 1.01 mmol) were added XPhos (7.21 mg, 0.015 mmol) and XPhosG3 (12.8 mg, 0.015 mmol). The reaction vial was sealed with a septum and then evacuated/refilled with argon 3 times. An argon-filled balloon was attached via a needle and the reaction was allowed to stir at 105° C. for 1 h. The reaction mixture was allowed to cool to rt and then poured into stirring saline (~30 mL). The reaction vial was rinsed with water and this was added to the stirring mixture. The precipitate which formed was isolated by filtration through a fritted funnel, washed with water, and then dried under vacuum overnight to provide the crude product as a grey solid. LCMS analysis of the crude product showed products I-49 and I-50. The crude compounds were separated and purified by column chromatography to provide N-{4-[1-(cyclopropylsulfonyl)-1H-pyrrolo[2,3-c]pyridin-4-yl]pyridin-2-yl}pyrimidin-4-amine I-49 (75 mg, 38% yield) LCMS (FA): m/z=393.1 (M+H) and N-[4-(1H-pyrrolo[2,3-c]pyridin-4-yl)pyridin-2-yl]pyrimidin-4-amine I-50 (40 mg, 30% yield) LCMS (FA): m/z=289.1 (M+H).

Example 15: 2-methyl-N-[4-(7-methyl-1H-pyrrolo[2,3-c]pyridin-4-yl)pyridin-2-yl]pyrimidin-4-amine (I-51)

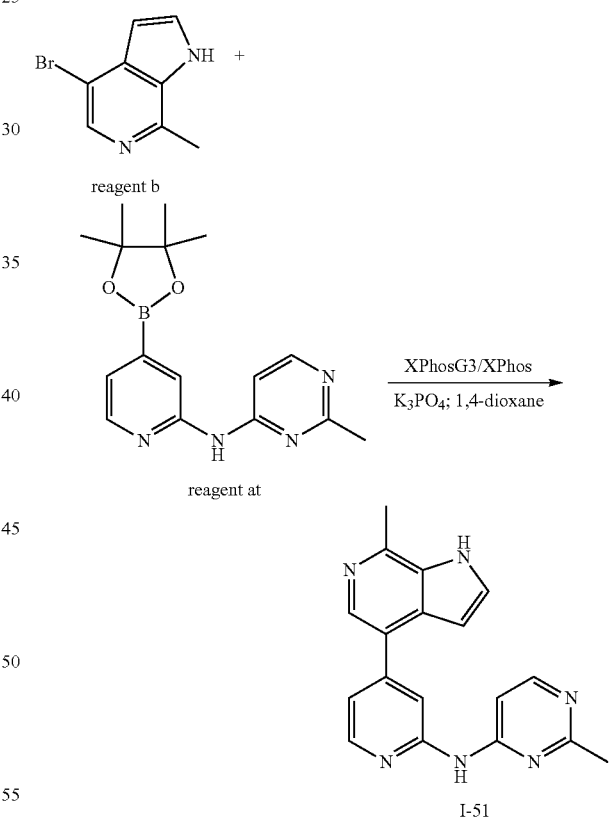

A mixture of 4-bromo-7-methyl-1H-pyrrolo[2,3-c]pyridine (0.13 g, 0.62 mmol), 2-methyl-N-[4-(4,4,5,5-tetramethyl-1,3,2-dioxaborolan-2-yl)pyridin-2-yl]pyrimidin-4-amine (0.23 g, 0.74 mmol), XPhos (0.08 g, 0.02 mmol), XPhosG3 (0.012 g, 0.02 mmol), degassed K$_3$PO$_4$ solution (0.50 M in water, 2.43 mL, 1.21 mmol) and degassed 1,4-dioxane (2.13 mL) was allowed to stir at 105° C. for 2 h, then was allowed to cool to rt and filtered through celite. The filtrate was diluted with EtOAc and then washed with water. The organic solution was dried over Na$_2$SO$_4$, filtered, and concentrated. The crude compound was purified by column chromatography to provide 2-methyl-N-[4-(7-methyl-1H-pyrrolo[2,3-c]pyridin-4-yl)pyridin-2-yl]pyrimidin-4-amine (0.115 g, 59% yield). LCMS (FA): m/z=317.2 (M+H). $^1$H NMR (400 MHz. DMSO-$d_6$) δ 11.92 (s, 1H), 10.26 (s, 1H), 8.38 (d, J=5.2 Hz, 1H), 8.34 (d, J=5.9 Hz, 1H), 8.28 (s, 1H), 8.24 (s, 1H), 7.75 (t, J=2.8 Hz, 1H), 7.58 (d, J=5.7 Hz, 1H), 7.35 (dd, J=5.2, 1.4 Hz, 1H), 6.90 (s, 1H), 2.73 (s, 3H), 2.45 (s, 3H).

Biological Protocols and Data:

Example 14: VPS34 Enzyme Assays

Cloning, Expression, and Purification of VPS34

VPS34 (accession number GB:BC033004) was cloned into pDEST20-Thombin as N-terminal GST tagged fusion proteins using the Gateway system (Invitrogen, catalog#11804-013). The sequences were verified before recombinant protein expression using the Baculovirus Expression System with Gateway® Technology.

For expression VPS34 was infected at 1 MOI in SF9 cells and harvested 72 hours post infection.

For purification, VPS34 is purified by Glutathione Sepharose 4 Fast Flow (GE Healthcare #17-5132-03) followed by HiTrap Q (GE Healthcare #17-1153-01).

VPS34 Assay Conditions

Human VPS34 Enzyme Assay Method 100 nL compounds in DMSO are added to wells of a 384 well microtitre plate (Greiner 780076). At room temperature: 5 ul VPS34 reaction buffer (Invitrogen Assay Buffer Q (diluted 1 in 5 with nanopure water) plus 2 mM DTT and 2 mM $MnCl_2$) containing ATP (20 uM, Promega) and 200 uM PI-PS substrate (Invitrogen PV5122) is added followed immediately by 5 ul VPS34 reaction buffer (as above) containing VPS34 (5 nM, Millennium Protein Sciences Group) and the mixture is incubated with shaking at room temperature for 1 hour. Then 5 ul VPS34 stop-detect mix (as per Invitrogen Adapta Assay kit (PV5009) instructions (contains kinase quench buffer, TR-FRET buffer, Adapta Eu anti-ADP antibody and Alexa Fluor 647 ADP tracer)) is added to quench the reaction. The plates are then incubated for 30 minutes at room temperature with shaking and then read on a BMG PheraStar Plus reader.

For the assay methods described above, test compound percent inhibition, at various concentrations, is calculated relative to control (DMSO and EDTA) treated samples. Compound concentration versus percent inhibition curves are fitted to generate $IC_{50}$ values. One skilled in the art will appreciate that the values generated either as percentage inhibition at a single concentration or $IC_{50}$ values are subject to experimental variation.

Inhibition of VPS34

In some embodiments, compounds of the invention were assayed using the human VPS34 enzyme assay method described above and inhibited VPS34 at a 1.11 µM concentration with the % inhibition values as shown in the table below (Table 6). Additionally, compounds of the invention that inhibit VPS34 are described with the following $IC_{50}$ ranges: (A) <10 nM; (B) 10 nM-<50 nM; (C) 50 nM-<100 nM; or (D) greater than 100 nM.

| Compound | Percent Inhibition | $IC_{50}$ |
|---|---|---|
| I-1 | >99 | A |
| I-2 | >99 | A |
| I-3 | >99 | A |

-continued

| Compound | Percent Inhibition | $IC_{50}$ |
|---|---|---|
| I-4 | >99 | A |
| I-5 | >99 | C |
| I-6 | >99 | B |
| I-7 | >99 | A |
| I-8 | >99 | B |
| I-9 | >99 | B |
| I-10 | >99 | A |
| I-11 | >99 | B |
| I-12 | >99 | B |
| I-13 | >99 | B |
| I-14 | >99 | B |
| I-15 | >99 | A |
| I-16 | >99 | A |
| I-17 | >99 | A |
| I-18 | >99 | B |
| I-20 | >99 | C |
| I-21 | >99 | B |
| I-22 | >99 | C |
| I-23 | >99 | A |
| I-24 | >99 | B |
| I-25 | >99 | A |
| I-27 | >99 | B |
| I-28 | >99 | B |
| I-29 | >99 | B |
| I-30 | 99 | B |
| I-31 | >99 | B |
| I-32 | 30 | D |
| I-33 | >99 | A |
| I-34 | >99 | B |
| I-35 | >99 | A |
| I-36 | 79 | D |
| I-37 | >99 | A |
| I-38 | 99 | B |
| I-39 | >99 | A |
| I-40 | >99 | C |
| I-41 | >99 | B |
| I-42 | >99 | A |
| I-43 | >99 | A |
| I-44 | >99 | B |
| I-45 | >99 | B |
| I-46 | >99 | B |
| I-47 | >99 | B |
| I-48 | >99 | B |
| I-49 | 88 | B |
| I-50 | 82 | B |
| I-51 | 91 | B |

Example 15: Tumor Xenograft Model

The in vivo efficacy of the compounds described herein as, e.g., single agents or in combination therapy, can be studied using tumor xenograft models. Female nude mice can be inoculated subcutaneously in flank with 2.0×10$^6$ human colorectal adenocarcinoma cells SW48. A similar experiment can be conducted in human non-small cell lung cancer cells PC9 and H1650. Female nude mice can be inoculated subcutaneously in flank with 2.0×10$^6$ cells+matrigel.

Tumor growth can be monitored with vernier calipers. The mean tumor volume can be calculated using the formula $V=W^2 \times L/2$. When the mean tumor volume reaches approximately 150-200 mm$^3$, the animals can be randomized into treatment groups. A compound described herein, as well as reference compounds or other therapeutic agents and vehicle control can be administered by various methods, including oral gavage. Administration can occur, for example, once per day for fourteen or twenty-one days. Administration of the compound, reference compound, or other therapeutic agent can be administered as single agents or in combination. Tumor growth and body weight can be measured twice per week.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:
1. A compound of formula I:

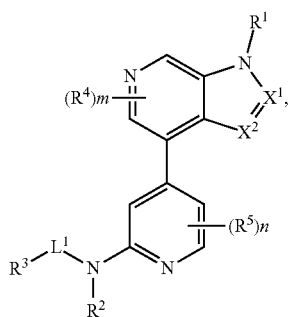

I or a pharmaceutically acceptable salt thereof, wherein:
each of $X^1$ and $X^2$, independently, is CH or $CR^4$;
$L^1$ is a bond, —C(O)—, —C(O)—O—, —S(O)$_2$—, —C(O)N($R^a$)—, or —S(O)$_2$N($R^a$)—; wherein each $R^a$, independently, is hydrogen or $C_{1-4}$ alkyl;
$R^1$ is hydrogen or -$L^2$-$R^6$ wherein:
  $L^2$ is $C_{1-4}$ alkylene, —C(O)—, —C(O)—O—, —S(O)—, —S(O)$_2$—, —C(O)N($R^b$)—, or —S(O)$_2$N($R^b$)—; wherein each $R^b$, independently, is hydrogen or $C_{1-4}$ alkyl; and
  $R^6$ is hydrogen, $C_{1-6}$ aliphatic, 3-10-membered cycloaliphatic, phenyl, or naphthyl; each of which being optionally substituted with 1-5 $R^7$;
$R^2$ is hydrogen or $C_{1-4}$ alkyl;
$R^3$ is hydrogen, $C_{1-6}$ aliphatic, 3-10-membered cycloaliphatic, phenyl, or naphthyl; provided that if $R^3$ is hydrogen, then $L^1$ is a bond; each of $R^3$ being optionally substituted with 1-5 $R^7$ wherein:
each $R^7$ independently is CN, halo, or $L^3$-$R^8$ wherein:
  $L^3$ is a bond, $C_{1-4}$ aliphatic, —O—, —N($R^c$)—, —S—, —S(O)—, —S(O)$_2$—, —C(O)—, —C(O)O—, —C(O)N($R^c$)—, —N($R^c$)C(O)—, —N($R^c$)C(O)O—, —S(O)$_2$N$R^c$—, —N($R^c$)S(O)$_2$—, —OC(O)N($R^c$)—, —N($R^c$)C(O)N($R^d$)—, —N($R^c$)S(O)$_2$N($R^d$)—, or —OC(O)—;
  each occurrence of $R^c$ and $R^d$, independently, is hydrogen or $C_{1-4}$ alkyl, and
  $R^8$ is hydrogen, $C_{1-6}$ aliphatic, 3-10-membered cycloaliphatic, phenyl, or naphthyl;
each occurrence of $R^4$ and $R^5$, independently, is —CN, halo, or -$L^4$-$R^9$ wherein:
  $L^4$ is $C_{1-4}$ alkylene, —O—, —N($R^e$)—, —S—, —S(O)—, —S(O)$_2$—, —C(O)—, —CO$_2$—, —C(O)N($R^e$)—, —N($R^e$)C(O)—, —N($R^e$)C(O)O—, —S(O)$_2$N($R^e$)—, —N($R^e$)S(O)$_2$—, —OC(O)N($R^e$)—, —N($R^e$)C(O)N($R^f$)—, —N($R^e$)S(O)$_2$N($R^f$)—, or —OC(O)—;
  each occurrence of $R^e$ and $R^f$, independently, is hydrogen or $C_{1-4}$ alkyl; and
  $R^9$ is hydrogen, —NH$_2$, or $C_{1-6}$ aliphatic;
m is 0-2; and
n is 0-3.
2. The compound or a pharmaceutically acceptable salt of claim 1, wherein $R^1$ is -$L^2$-$R^6$.

3. The compound or a pharmaceutically acceptable salt of claim 2, wherein $L^1$ is —C(O)— or —C(O)O—.
4. The compound or a pharmaceutically acceptable salt of claim 2, wherein $X^1$ and $X^2$ are both CH.
5. The compound or a pharmaceutically acceptable salt of claim 2, wherein $L^2$ is —C(O)— or —S(O)$_2$—.
6. The compound or a pharmaceutically acceptable salt of claim 2, wherein $R^6$ is methyl, ethyl, or phenyl optionally substituted with 1-3 groups selected from halo or $C_{1-3}$ alkyl.
7. The compound or a pharmaceutically acceptable salt of claim 2, wherein $R^2$ is hydrogen.
8. The compound or a pharmaceutically acceptable salt of claim 2, wherein $R^3$ is $C_{1-3}$ alkyl.
9. The compound or a pharmaceutically acceptable salt of claim 2, wherein $L^1$ is a bond.
10. The compound or a pharmaceutically acceptable salt of claim 2, wherein $R^4$ is substituted at the ring position between the ring nitrogen and the ring carbon connected to —N($R^1$)—.
11. The compound or a pharmaceutically acceptable salt of claim 1 with formula (II) below:

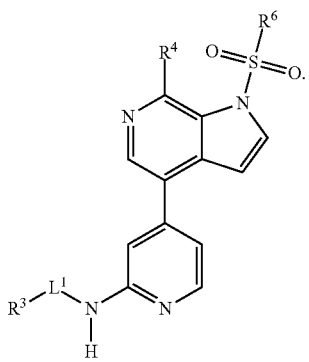

II

12. The compound or a pharmaceutically acceptable salt of claim 11, wherein $R^6$ is $C_{1-4}$ alkyl, 3-6-membered cycloaliphatic, phenyl, or naphthyl; $R^3$ is $C_{1-3}$ alkyl; and $R^4$ is halo or -$L^4$-$R^9$, wherein $L^4$ is $C_{1-4}$ alkylene chain, —O—, or —N($R^e$)—, and wherein $R^e$ is hydrogen or methyl, and $R^9$ is hydrogen or $C_{1-3}$ alkyl.
13. The compound or a pharmaceutically acceptable salt of claim 11, wherein $R^6$ is methyl, ethyl, cyclopropyl, or phenyl optionally substituted with $C_{1-3}$ alkyl, fluoro, or chloro.
14. A compound or a pharmaceutically acceptable salt thereof, wherein the compound is one of:

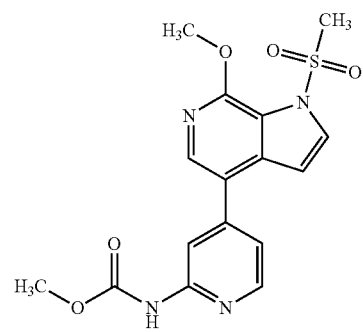 [SMILES: COC(=O)Nc1cc(-c2cnc(OC)c3c2ccn3S(C)(=O)=O)ccn1]

I-1

-continued
I-2
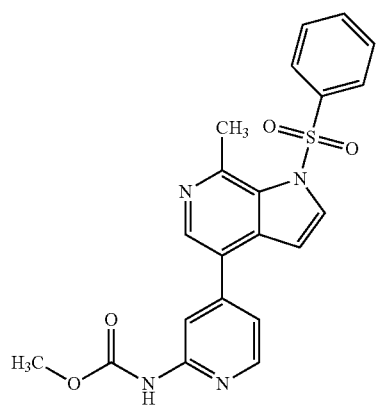 [SMILES: COC(=O)Nc1cc(-c2cnc(C)c3c2ccn3S(=O)(=O)c2ccccc2)ccn1]
I-3
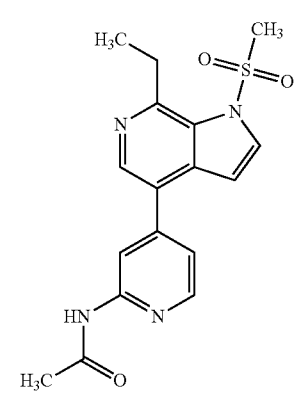 [SMILES: CCc1ncc(-c2ccnc(NC(C)=O)c2)c2ccn(S(C)(=O)=O)c12]
I-4
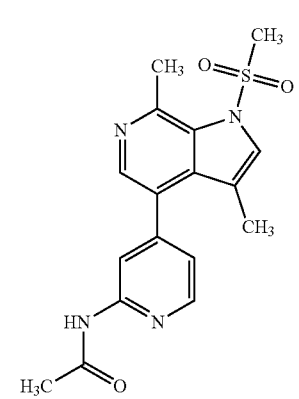
I-5
-continued
I-6
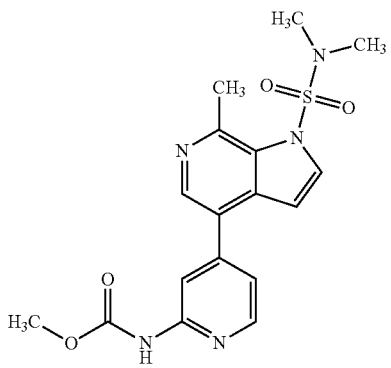
I-7
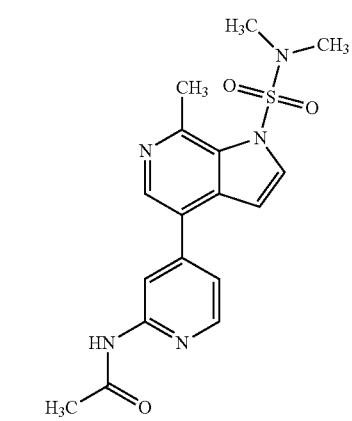 [SMILES: CC(=O)Nc1cc(-c2cnc(C)c3c2ccn3S(=O)(=O)N(C)C)ccn1]
I-8
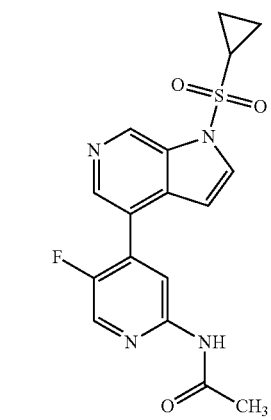 [SMILES: CC(=O)Nc1cc(-c2cncc3c2ccn3S(=O)(=O)C2CC2)c(F)cn1]
I-10
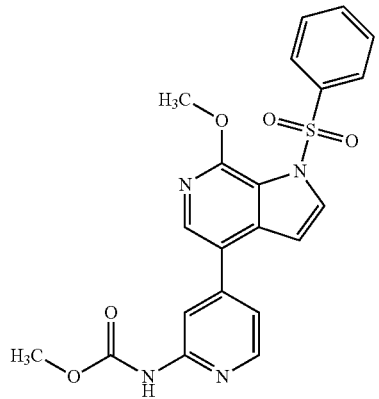 [SMILES: COC(=O)Nc1cc(-c2cnc(OC)c3c2ccn3S(=O)(=O)c2ccccc2)ccn1]

-continued
I-11
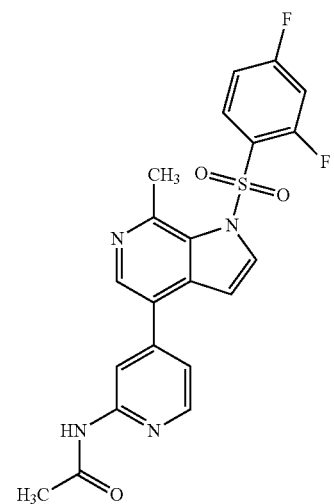 [SMILES: CC(=O)Nc1cc(-c2cnc(C)c3c2ccn3S(=O)(=O)c2ccc(F)cc2F)ccn1]
I-12
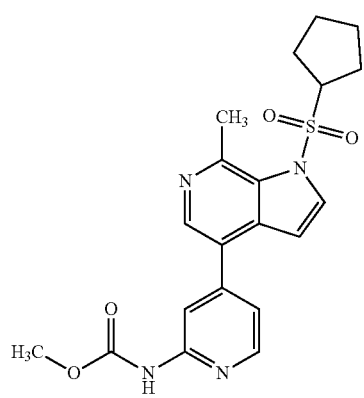 [SMILES: COC(=O)Nc1cc(-c2cnc(C)c3c2ccn3S(=O)(=O)C2CCCC2)ccn1]
I-14
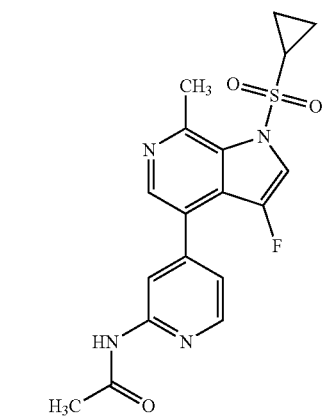
-continued
I-15
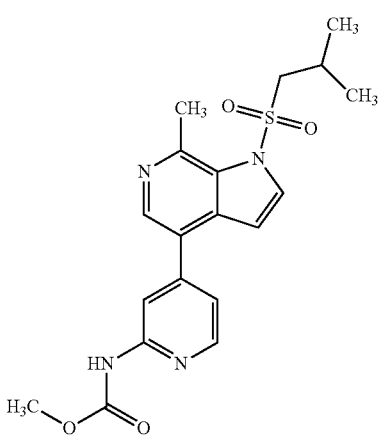 [SMILES: COC(=O)Nc1cc(-c2cnc(C)c3c2ccn3S(=O)(=O)CC(C)C)ccn1]
I-16
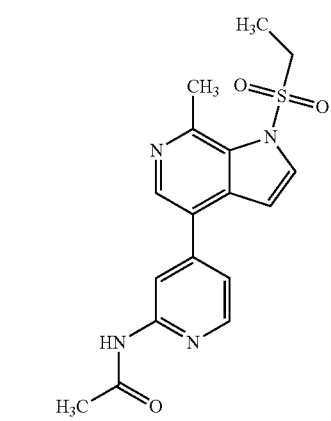 [SMILES: CCS(=O)(=O)n1ccc2c(-c3ccnc(NC(C)=O)c3)cnc(C)c21]
I-17
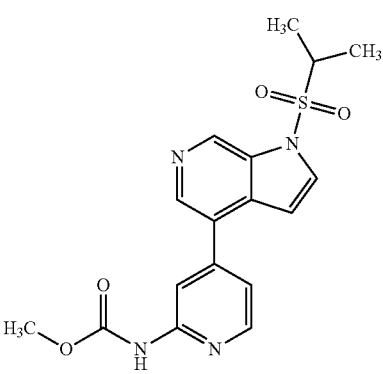
I-18
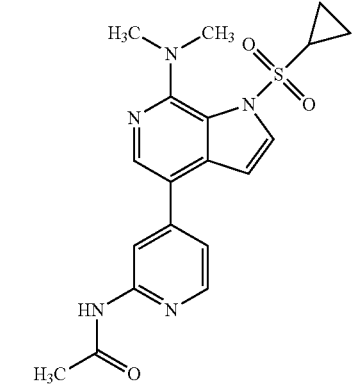 [SMILES: CC(=O)Nc1cc(-c2cnc(N(C)C)c3c2ccn3S(=O)(=O)C2CC2)ccn1]

-continued
I-20
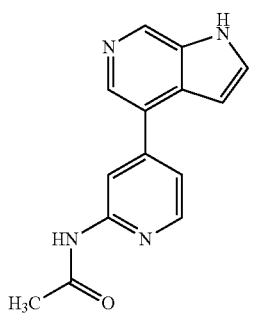 [SMILES: CC(=O)Nc1cc(-c2cncc3[nH]ccc23)ccn1]
I-21
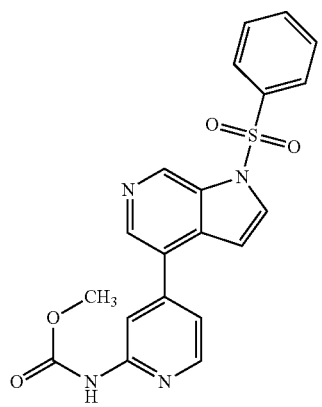 [SMILES: COC(=O)Nc1cc(-c2cncc3c2ccn3S(=O)(=O)c2ccccc2)ccn1]
I-22
I-24
I-25
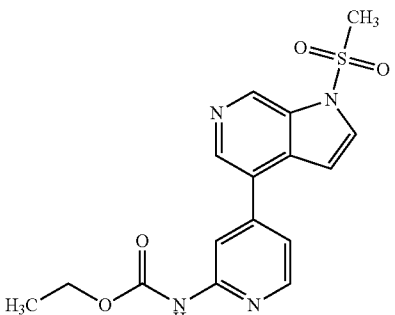
I-28
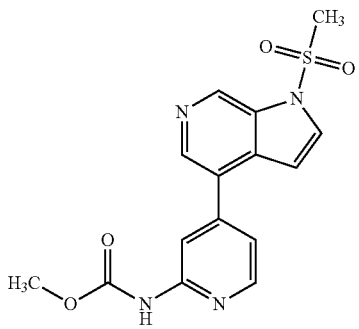 [SMILES: COC(=O)Nc1cc(-c2cncc3c2ccn3S(C)(=O)=O)ccn1]
I-29
I-30
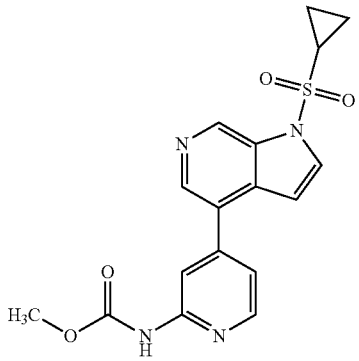 [SMILES: COC(=O)Nc1cc(-c2cncc3c2ccn3S(=O)(=O)C2CC2)ccn1]

| I-31 | I-35 |
| I-32 | |
| I-33 | I-36 |
| I-34 | I-37 |

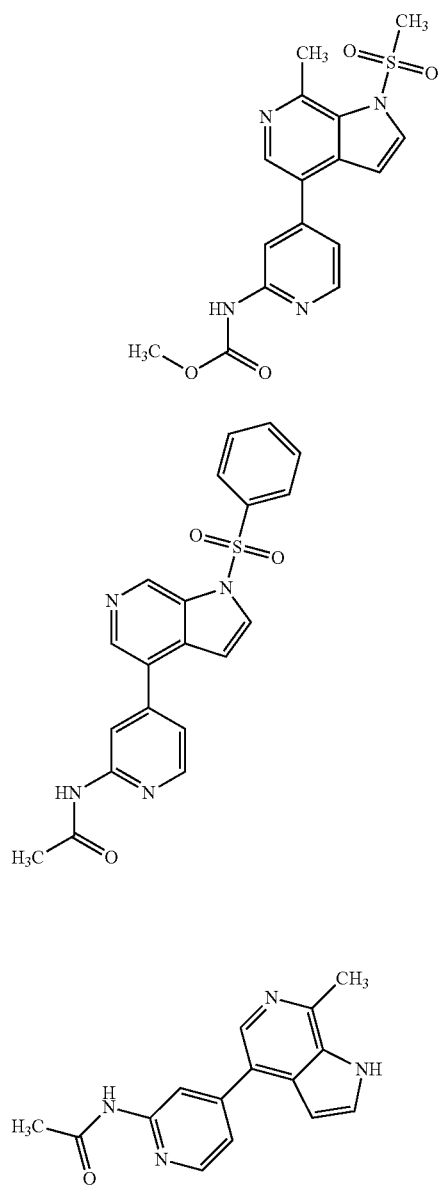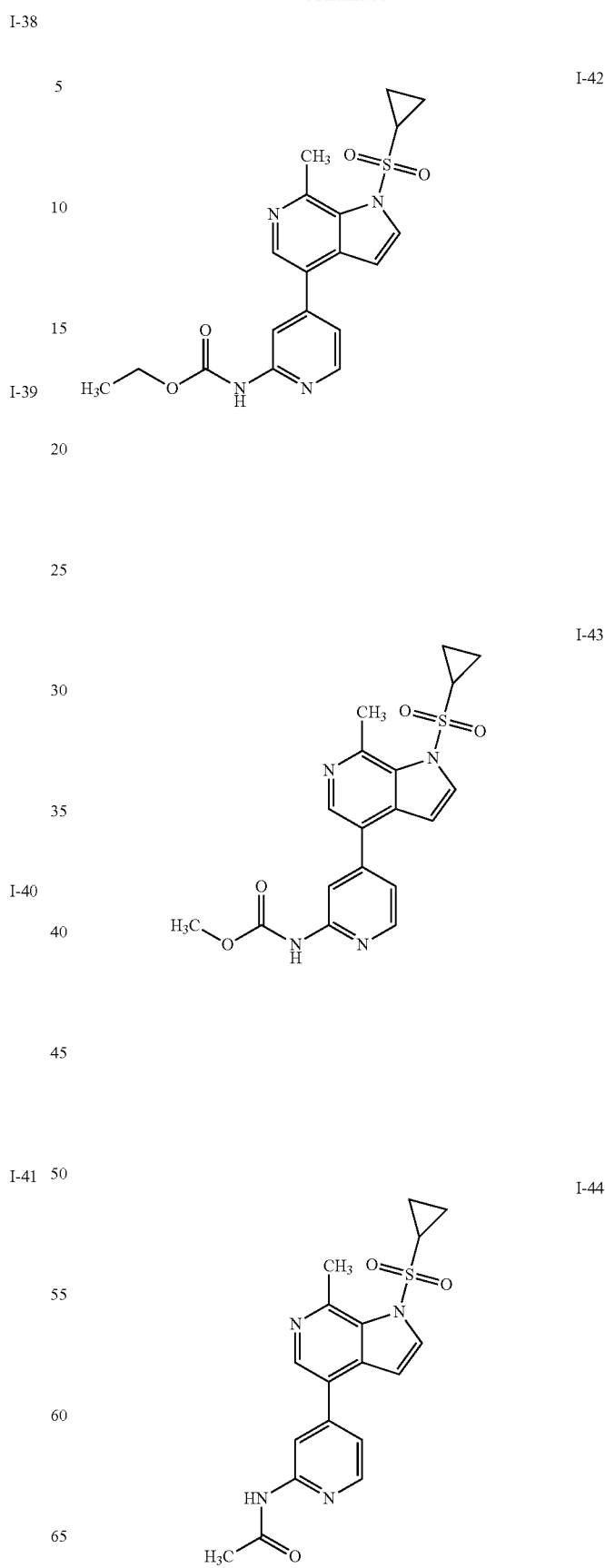

I-45
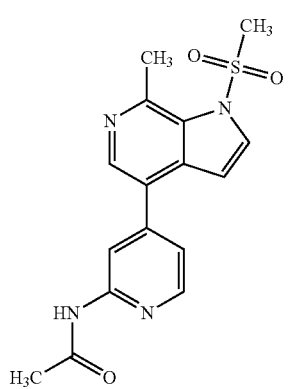 [SMILES: CC(=O)Nc1cc(-c2cnc(C)c3c2ccn3S(C)(=O)=O)ccn1]
I-46
I-47
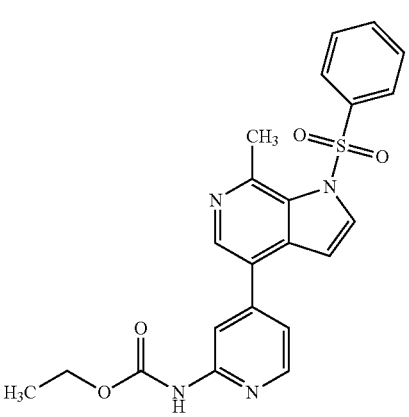 [SMILES: CCOC(=O)Nc1cc(-c2cnc(C)c3c2ccn3S(=O)(=O)c2ccccc2)ccn1]
or
I-48
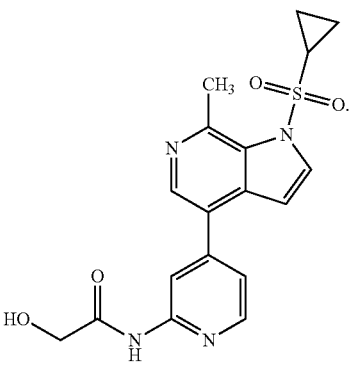
15. A pharmaceutical composition comprising a compound or a pharmaceutically acceptable salt of claim 1, and a pharmaceutically acceptable carrier.
* * * * *